US011400145B2

(12) United States Patent
Boyd et al.

(10) Patent No.: US 11,400,145 B2
(45) Date of Patent: Aug. 2, 2022

(54) GENETICALLY MODIFIED CELLS AND USES THEREOF

(71) Applicant: CARTHERICS PTY. LTD., Carlton (AU)

(72) Inventors: Richard Boyd, Carlton (AU); Alan Trounson, Carlton (AU); Hiroshi Kawamoto, Carlton (AU); Peter John Hudson, Inverloch (AU); Runzhe Shu, Carlton (AU)

(73) Assignee: CARTHERICS PTY. LTD., Carlton (AU)

( * ) Notice: Subject to any disclaimer, the term of this patent is extended or adjusted under 35 U.S.C. 154(b) by 0 days.

(21) Appl. No.: 15/778,836

(22) PCT Filed: Nov. 23, 2016

(86) PCT No.: PCT/AU2016/051141
§ 371 (c)(1),
(2) Date: May 24, 2018

(87) PCT Pub. No.: WO2017/088012
PCT Pub. Date: Jun. 1, 2017

(65) Prior Publication Data
US 2018/0353588 A1 Dec. 13, 2018

(30) Foreign Application Priority Data
Apr. 11, 2016 (AU) .............................. 2016901328

(51) Int. Cl.
| A61K 39/00 | (2006.01) |
| C07K 14/725 | (2006.01) |
| C07K 16/28 | (2006.01) |
| A61K 35/17 | (2015.01) |
| A61K 38/17 | (2006.01) |
| C07K 14/47 | (2006.01) |
| A61P 35/00 | (2006.01) |
| C12N 5/0783 | (2010.01) |
| C07K 16/30 | (2006.01) |
| A61K 35/545 | (2015.01) |
| C07K 14/705 | (2006.01) |

(52) U.S. Cl.
CPC ...... *A61K 39/001153* (2018.08); *A61K 35/17* (2013.01); *A61K 35/545* (2013.01); *A61K 38/1774* (2013.01); *A61K 39/001102* (2018.08); *A61P 35/00* (2018.01); *C07K 14/4748* (2013.01); *C07K 14/7051* (2013.01); *C07K 14/70517* (2013.01); *C07K 16/2803* (2013.01); *C07K 16/3092* (2013.01); *C12N 5/0636* (2013.01); *C12N 5/0638* (2013.01); *A61K 2039/5158* (2013.01); *C07K 2317/622* (2013.01); *C07K 2319/02* (2013.01); *C07K 2319/03* (2013.01); *C07K 2319/33* (2013.01); *C12N 2506/45* (2013.01); *C12N 2510/00* (2013.01)

(58) Field of Classification Search
CPC ............ A61K 39/001153; A61K 35/17; A61K 35/545; A61K 38/1774; A61K 39/001102; A61K 2039/5158; C07K 14/4748; C07K 16/3092; C07K 14/70517; C07K 16/2803; C07K 14/7051; C07K 2319/33; C07K 2317/622; C07K 2319/02; C07K 2319/03; A61P 35/00; C12N 5/0636; C12N 5/0638; C12N 2506/45; C12N 2510/00
See application file for complete search history.

(56) References Cited

U.S. PATENT DOCUMENTS

| 5,786,146 A | 7/1998 | Herman et al. |
| 6,465,247 B1 | 10/2002 | Weissman et al. |
| 6,761,883 B2 | 7/2004 | Weissman et al. |
| 6,908,763 B1 | 6/2005 | Akashi et al. |
| 7,217,568 B2 | 5/2007 | Jamieson et al. |

(Continued)

FOREIGN PATENT DOCUMENTS

| CN | 103492406 A | 1/2014 |
| CN | 104159909 A | 11/2014 |

(Continued)

OTHER PUBLICATIONS

Deniger et al. (2013, Molecular Therapy, vol. 21(3), pp. 638-647) (Year: 2013).*
McGuinness et al. Anti-Tumor Activity of Human T Cells Expressing the CC49-z Chimeric Immune Receptor Human Gene Therapy, vol. 10, No. 2 165-173 1999 (Year: 1999).*
Curran K.J. et al., "Enhancing Antitumor Efficacy of Chimeric Antigen Receptor T Cells Through Constitutive CD40L Expression", Molecular Therapy 23(4):769-778 (Apr. 2015).

(Continued)

*Primary Examiner* — Amy E Juedes
*Assistant Examiner* — Brian Hartnett
(74) *Attorney, Agent, or Firm* — Scully, Scott, Murphy & Presser, P.C.

(57) ABSTRACT

The present invention relates generally to a population of stem cells (e.g., iPSCs or HSCs) that comprise nucleic acids encoding a T cell receptor and a chimeric antigen receptor directed to multiple distinct antigenic determinants, for example two distinct tumour antigenic determinants. The present invention is also directed to a population of T cells that co-express a T cell receptor and a chimeric antigen receptor directed to multiple distinct antigenic determinants, such as two distinct tumour antigenic determinants. The cells of the present invention can be derived from chosen donors whose HLA type is compatible with significant sectors of the populations, and are useful in a wide variety of applications, in particular in the context of the therapeutic treatment of neoplastic conditions.

22 Claims, 30 Drawing Sheets
(17 of 30 Drawing Sheet(s) Filed in Color)
Specification includes a Sequence Listing.

(56) References Cited

U.S. PATENT DOCUMENTS

| | | | |
|---|---|---|---|
| 7,297,329 B2 | 11/2007 | Akashi et al. | |
| 7,300,760 B2 | 11/2007 | Weissman et al. | |
| 7,494,807 B2 | 2/2009 | Nakorn et al. | |
| 7,514,229 B2 | 4/2009 | Jamieson et al. | |
| 7,589,181 B2 | 9/2009 | Kashmiri et al. | |
| 7,592,174 B2 | 9/2009 | Sylvester et al. | |
| 7,618,654 B2 | 11/2009 | Weissman et al. | |
| 7,622,255 B2 | 11/2009 | Jamieson et al. | |
| 7,641,897 B2 | 1/2010 | Weissman et al. | |
| 7,749,754 B2 | 7/2010 | Sherwood et al. | |
| 7,767,410 B2 | 8/2010 | Weissman et al. | |
| 7,781,179 B2 | 8/2010 | Weissman et al. | |
| 7,816,088 B2 | 10/2010 | Jamieson et al. | |
| 8,153,388 B2 | 4/2012 | Jamieson et al. | |
| 8,232,071 B2 | 7/2012 | Weissman et al. | |
| 8,236,313 B2 | 8/2012 | Isenberg et al. | |
| 8,320,687 B2 | 11/2012 | Weissman et al. | |
| 8,361,736 B2 | 1/2013 | Majeti et al. | |
| 8,377,448 B2 | 2/2013 | Smith et al. | |
| 8,557,788 B2 | 10/2013 | Isenberg et al. | |
| 8,562,997 B2 | 10/2013 | Jaiswal et al. | |
| 8,691,780 B2 | 4/2014 | Lih et al. | |
| 8,709,429 B2 | 4/2014 | Majeti et al. | |
| 8,758,750 B2 | 6/2014 | Weissman et al. | |
| 8,765,390 B2 | 7/2014 | Ailles et al. | |
| 8,865,672 B2 | 10/2014 | Isenberg et al. | |
| 8,906,682 B2 | 12/2014 | June et al. | |
| 9,017,675 B2 | 4/2015 | Liu et al. | |
| 9,045,734 B2 | 6/2015 | Weissman et al. | |
| 9,151,760 B2 | 10/2015 | Weissman et al. | |
| 9,175,079 B2 | 11/2015 | Tang et al. | |
| 9,193,955 B2 | 11/2015 | Majeti et al. | |
| 9,221,908 B2 | 12/2015 | Frazier et al. | |
| 2004/0043401 A1* | 3/2004 | Sadelain ................ | C07H 21/04 435/6.16 |
| 2005/0069879 A1 | 3/2005 | Berlin | |
| 2006/0171941 A1 | 8/2006 | Kashmiri et al. | |
| 2009/0203104 A1* | 8/2009 | Fox ........................ | B82Y 5/00 435/188 |
| 2013/0149337 A1 | 6/2013 | Cooper et al. | |
| 2013/0280285 A1 | 10/2013 | Schonfeld et al. | |
| 2013/0287748 A1 | 10/2013 | June et al. | |
| 2014/0017213 A1 | 1/2014 | Li et al. | |
| 2014/0050708 A1 | 2/2014 | Powell et al. | |
| 2014/0363442 A1 | 12/2014 | Frazier et al. | |
| 2015/0183874 A1 | 7/2015 | Liu et al. | |
| 2015/0322169 A1 | 11/2015 | June et al. | |

FOREIGN PATENT DOCUMENTS

| | | | |
|---|---|---|---|
| CN | 105073776 A | 11/2015 | |
| CN | 105331586 A | 2/2016 | |
| WO | 98/18809 A1 | 5/1998 | |
| WO | WO-9818809 A1 * | 5/1998 | ....... C07K 14/70514 |
| WO | 00/70090 A1 | 11/2000 | |
| WO | 2011/000054 A1 | 1/2011 | |
| WO | 2012079000 A1 | 6/2012 | |
| WO | WO-2012079000 A1 * | 6/2012 | .............. A61P 35/02 |
| WO | 2013063419 A2 | 5/2013 | |
| WO | 2013126712 A1 | 8/2013 | |
| WO | 2013154760 A1 | 10/2013 | |
| WO | 2014011984 A1 | 1/2014 | |
| WO | 2014/165707 A2 | 10/2014 | |
| WO | 2016/154628 A1 | 9/2016 | |

OTHER PUBLICATIONS

Deniger D C et al., "Bispecific T-Cells Expressing Polyclonal Repertoire of Endogenous γδ T-Cell Receptors and Introduced CD19-Specific Chimeric Antigen Receptor", Molecular Therapy 21(3):638-647 (Mar. 2013).
Gourraud P-A et al., "The Role of Human Leukocyte Antigen Matching in the Development of Multiethnic "Haplobank" of Induced Pluripotent Stem Cell Lines", Cells 30(2):180-186 (Jan. 18, 2012).
Themeli M. et al., "New Cell Sources for T Cell Engineering and Adoptive Immunotherapy", Cell Stem Cell 16(4):357-366 (Apr. 2, 2015).
Extended Supplementary European Search Report dated Feb. 28, 2019 received in European Application No. 16 86 7445.5.
Hege K.M. et al., "Safety, Tumor Trafficking and Immunogenicity of Chimeric Antigen Receptor (CAR)-T Cells Specific for TAG-72 in Colorectal Cancer", Journal for ImmunoTherapy of Cancer 5:22 (2017).
Roberge M. et al., "Construtcion and Optimization of a CC49-Based scFv-β-Lactamase Fusion Protein for ADEPT", Protein Engineering & Selection 19(4):141-145 (Jan. 2006).
European Office Action dated Dec. 10, 2019 received in European Application No. 16 867 445.5.
Abergel C. et al., "Crystallographic Studies and Primary Structure of the Antitumor Monoclonal CC49 Fab", Proteins: Structure, Function, and Genetics 17:438-443 (1993).
Kashmiri S.V.S et al., "Generation, Characterization, and In Vivo Studies of Humanized Anticarcinoma Antibody CC49", Hybridoma 14(5):461-473 (Nov. 5, 1995).
Li L. et al., "Monodispersed PEG-DOTA Conjugated Anti-TAG-72 Diabody has Low Kidney Uptake and High Tumor to Blood Ratios Resulting in Improved 64Cu PET Imaging", J Nucl Med. 51(7):1139-1146 (Jul. 2010).
Louis C.U. et al., "Antitumor Activity and Long-Term Fate of Chimeric Antigen Receptor-Positive T Cells in Patients with Neuroblastoma", Blood 118(23):6050-6056 (2011).
Pavlinkova G. et al., "Effects of Humanization and Gene Shuffling on Immunogenicity and Antigen Binding of Anti-Tag-72 Single-Chain FVs", Int. J. Cancer 94:717-726 (2001).
Patel S.D. et al., "T-Cell Killing of Heterogenous Tumor or Viral Targets With Bispecific Chimeric Immune Receptors", Cancer Gene Therapy 7(8):1127-1134 (2000).
Sadelain M. et al., "The Basic Principles of Chimeric Antigen Receptor Design", Cancer Discovery 3(4):388-398 (2013).
Slaney C.Y. et al., "Dual-Specific Chimeric Antigen Receptor T Cells and an Indirect Vaccine Eradicate a Variety of Large Solid Tumors in an Immunocompetent, Self-Antigen Setting", Clinical Cancer Research 23(10):2478-2490 (2016).
Slanety C.Y. et al., "Dual-Specific T Cells and Oncolytic Virus Eradicate Large Solid Tumors", European Journal of Immunology 46(Suppl. 1):829, Abstract 1607 (Aug. 2016).
Wang X. et al., "CMVpp65 Vaccine Enhances the Antitumor Efficacy of Adoptively Transferred CD19-Redirected CVM-Specific T Cells", Clinical Cancer Research 21(13):2993-3002 (Jul. 1, 2015).
Wilkie S. et al., "Dual Targeting of ErbB2 and MUC1 in Breast Cancer Using Chimeric Antigen Receptors Engineered to Provide Complementary Signalling", J Clin Immunol 32:1059-1070 (2012).
Notices of Federal Register 72(95):27818-27821 (May 17, 2007).
Clinical Trials With CC49 (anti-Tag72) (10 pages) (2005).
International Search Report dated Feb. 15, 2017 received in International Application No. PCT/AU2016/051141.
European Communication dated Apr. 24, 2020 received in European Application No. 16 867 445.5.
Chmielewski M. et al., "TRUCKS: The Fourth Generation of CARS", Expert Opinion Biol. Ther. 15(8):1145-1154 (2015).
McGuinness R.P. et al., "Anti-Tumor Activity of Human T Cells Expression the CC49-ζ Chimeric Immune Receptor", Human Gene Therapy 10:165-173 (Jan. 20, 1999).
Pegram H.J. et al., "Blocking CD47 Improves CAR T Cell Therapy", Molecular Therapy 22(S1):S297 (May 2014).
Themeli M. et al., "Generation of Tumor-Targeted Human T Lymphocytes from Induced Pluripotent Stem Cells for Cancer Therapy", Nature Biotechnology 31(10):928-933 (Oct. 2013).
Supplementary Partial European Search Report dated Dec. 5, 2018 received in European Patent Application No. 16 86 7445.5.
Fitzer-Attas C.J. et al., "Harnessing Syk Family Tyrosine Kinases as Signaling Domains for Chimeric Single Chain of the Variable Domain Receptors: Optimal Design for T Cell Activation", The Journal of Immunology 160:145-154 (1998).

(56) References Cited

OTHER PUBLICATIONS

Malik N. et al., "A Reivew of the Methods for Human iPSC Derivation", Methods Mol Biol. 997:23-33 (2013).

Nolan K.F. et al., "Bypassing Immunization: Optimized Design of "Designer T Cells" Against Carcinoembryonic Antigen (CEA)-Expressing Tumors, and Lack of Suppression by Soluble CEA", Clinical Cancer Research 5:3928-3941 (Dec. 1999).

Pappas D J et al., "Proceedings: Human Leukocyte Antigen Haplo-Homozygous Induced Pluripotent Stem Cell Haplobank Modeled After the California Population: Evaluating Matching in a Multiethnic and Admixed Population", Stem Cells Translational Medicine 4:413-418 (2015).

Rodgers D.T. et al., "Switch-Mediated Activation and Retargeting of CAR-T Cells for B-Cell Malignancies", PNAS E459-E468 (Jan. 12, 2016).

Turner M. et al., "Toward the Development of a Global Induced Pluripotent Stem Cell Library", Cell Stem Cell 13:382-384 (Oct. 3, 2013).

Vizcardo R. et al. , "Regeneration of Human Tumor Antigen-Specific T Cells from iPSCs Derived from Mature CD8+ T Cells", Cell Stem Cell 12:31-36 (Jan. 3, 2013).

Wilmut I. et al., "Development of a Global Network of Induced Pluripotent Stem Cell Haplobanks", Regenerative Medicine 10(3):235-238 (2015).

Minagawa A. et al., "Rise of iPSCs as a Cell Source for Adoptive Immunotherapy", Human Cell 27:47-50 (2014).

Ueda T. et al., "Pluripotent Stem Cells as a Source for T Cell Research and Clinical Application", Jpn. J. Clin. Immunol. 38(2):101-108 (2015), together with an English-language abstract.

Japanese Notice of Reasons for Rejection dated Dec. 2, 2020 received in Japanese Patent Application No. 2018-546725, together with an English-language translation.

Desplancq D. et al., "Multimerization Behaviour of Single Chain Fv Variants for the Tumour-Binding Antibody B72.3", Protein Engineering 7(8):1027-1033 (1994).

Long N.E. et al., "Linker Engineering in Anti-TAG-72 Antibody Fragments Optimizes Biophysical Properties, Serum Half-Life, and High-Specificity Tumor Imaging", J Biol Chem. 293(23):9030-9040 (Jun. 8, 2018).

Shu L. et al., "Secretion of a Single-Gene-Encoded Immunoglobulin from Myeloma Cells", Proc. Natl. Acad. Sci. USA 90:7995-7999 (Sep. 1993).

Sun M, "Construction of a Novel Anti-HER2 Chimeric Antigen Receptor and its Function Evaluation in Vitro and In Vivo", Wanfang China Dissertation Database pp. 1-119 (2015).

Chinese Office Action dated Sep. 2, 2021 received in Chinese Application No. 201680069543.6, together with an English-language translation.

* cited by examiner

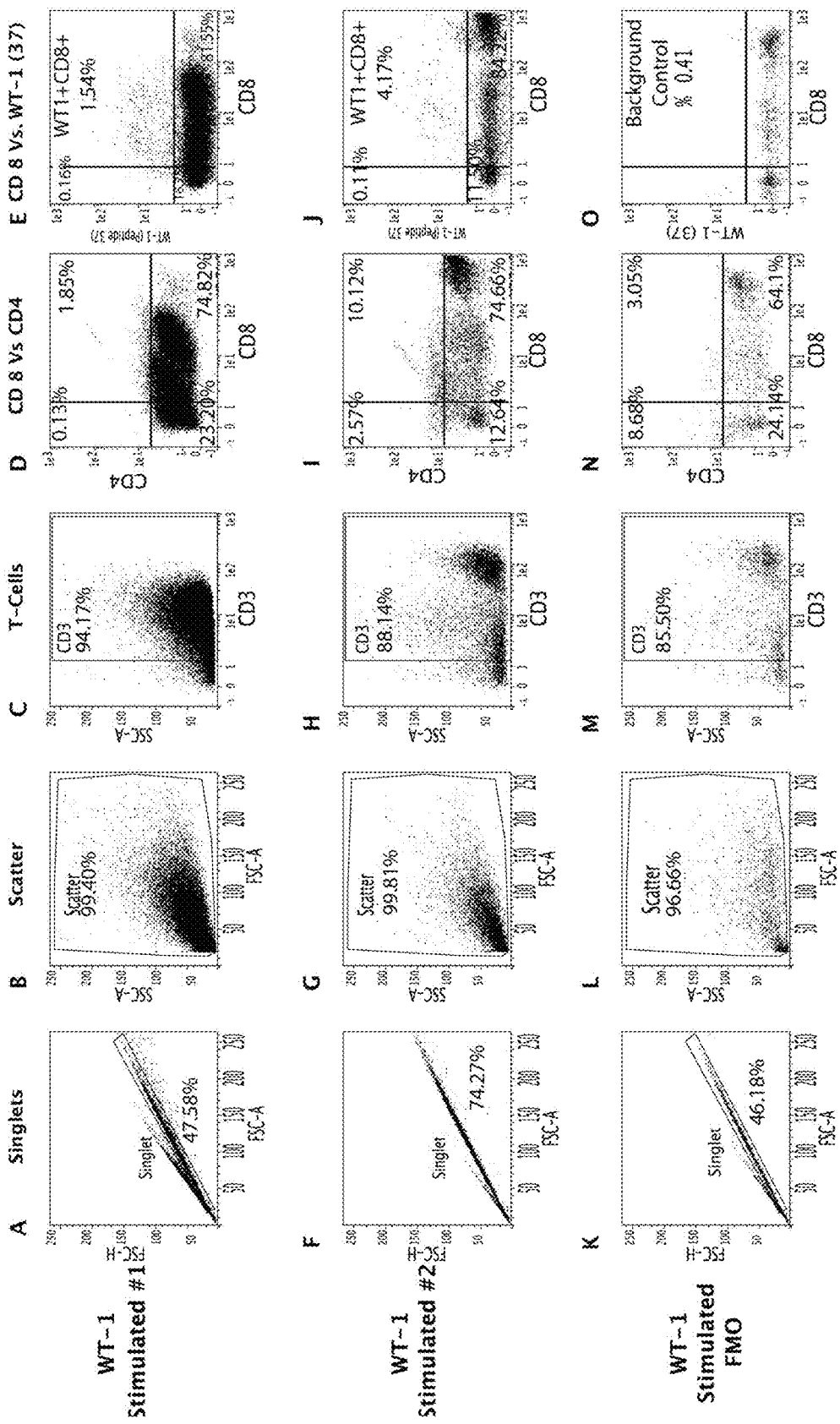

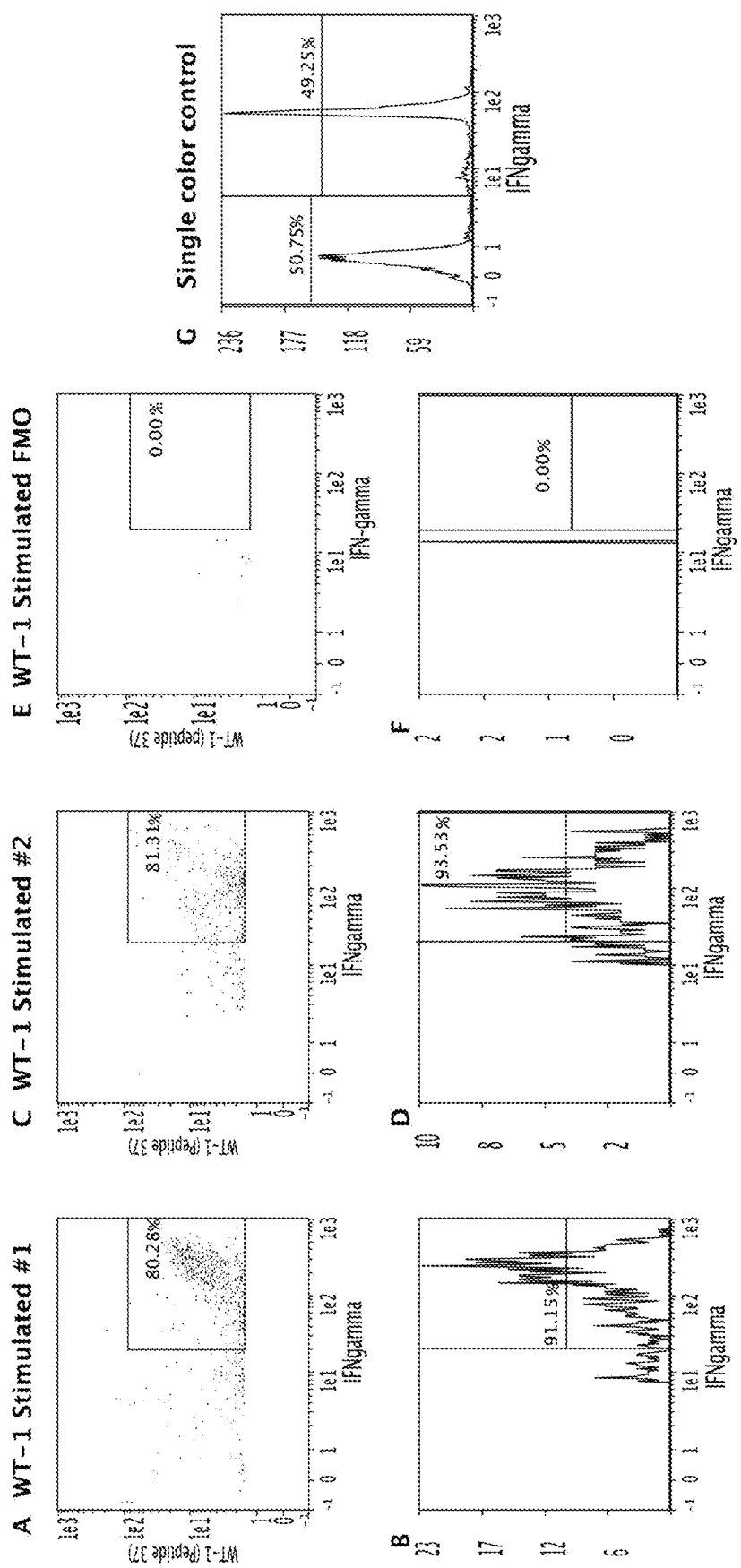

LAG 3 inhibitor (IMP 321) increases the frequency of WT-1 specific T cells

Production of iPSC from cancer specific (eg WT-1) TCR T cells

Differentiation of iPSC to hematopoietic T-cell precursors on OP9 feeder layers HSC-like cells are present after 13 days culture on OP9 cells Figure 5 (Continued)
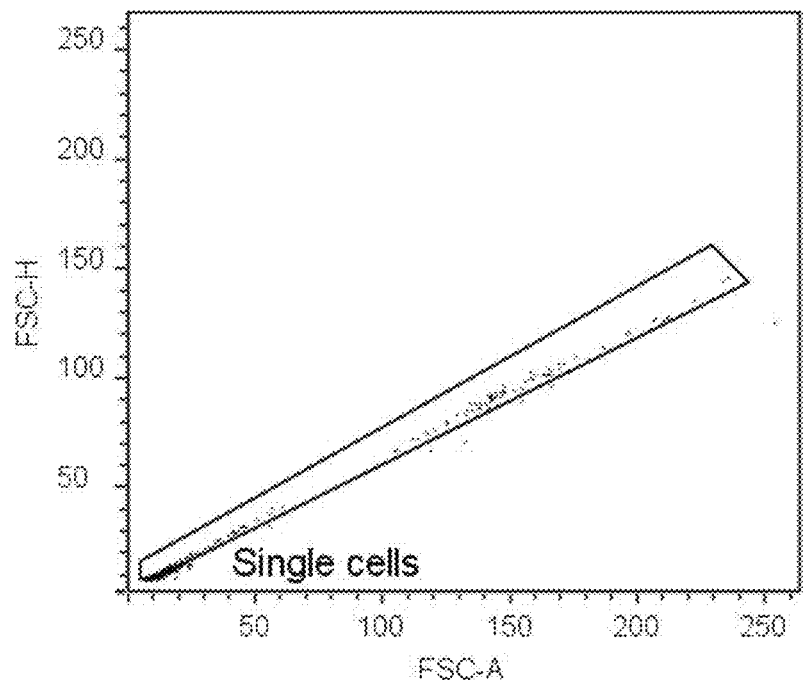
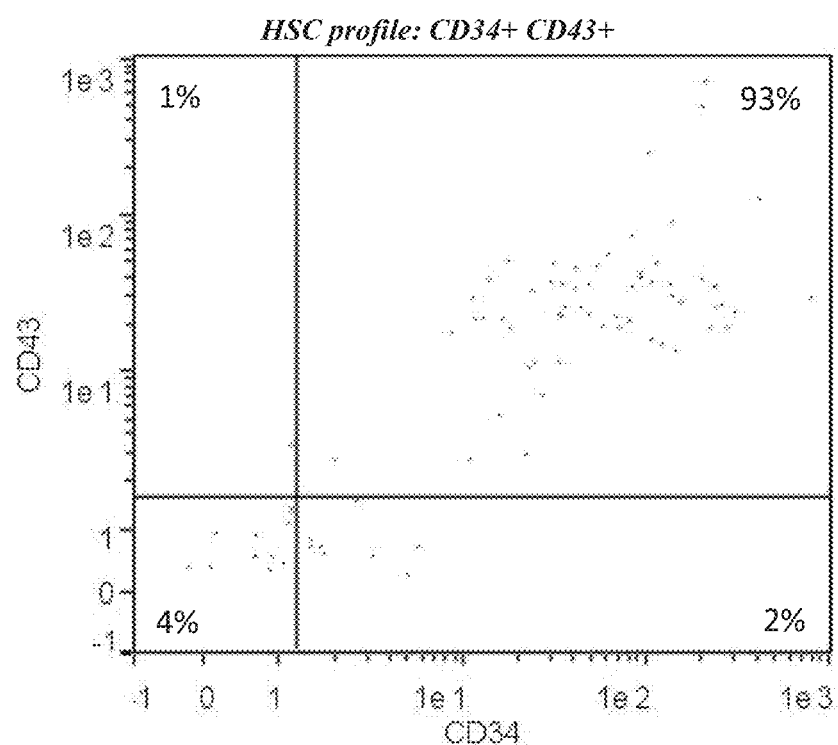

Figure 6
HSC are reduced after 9 days culture on OPDL-1 cells
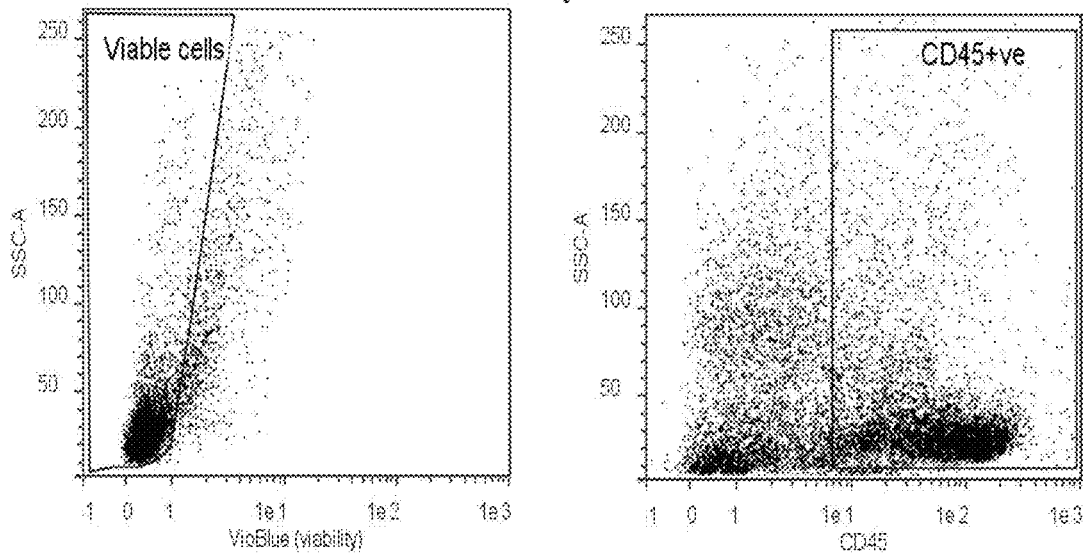
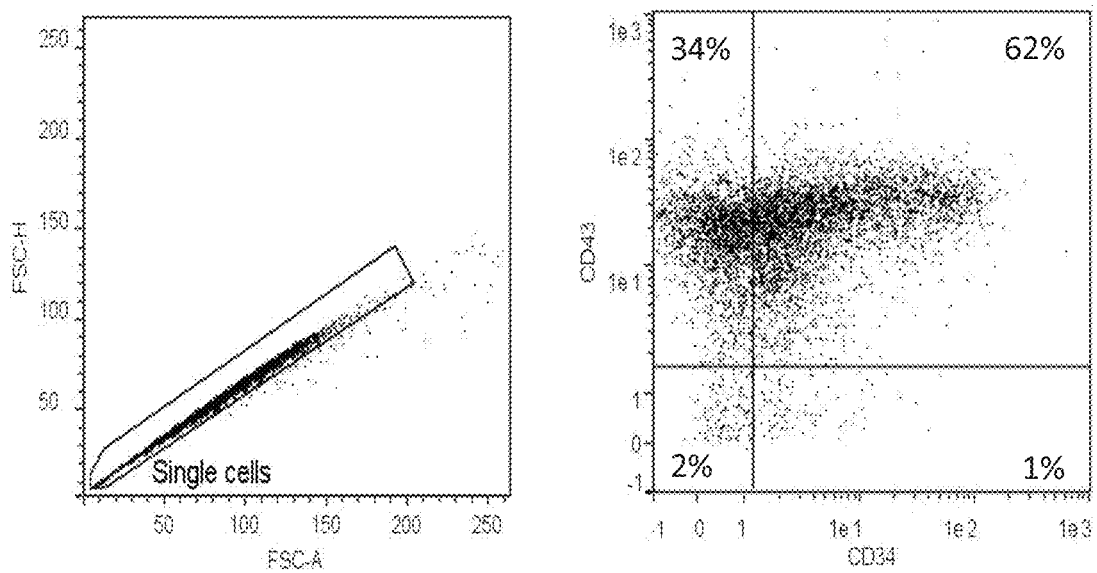
HSC profile: CD34+ CD43+

T cells are present after 9 days culture on OPDL-1 cells

Mature (CD3+α/β TCR+) CD8+ T cells are present after 16 days in culture on OPDL-1 cells Schematic representation of the induction of WT-1 specific TCR, CD8αβ T cells from iPSC Function of WT-1 specific TCR, CD8αβ T cells induced from iPSC Schematic diagram of chimeric antigen receptor and antigen-binding receptor constructs Retrovirus Transformation scheme

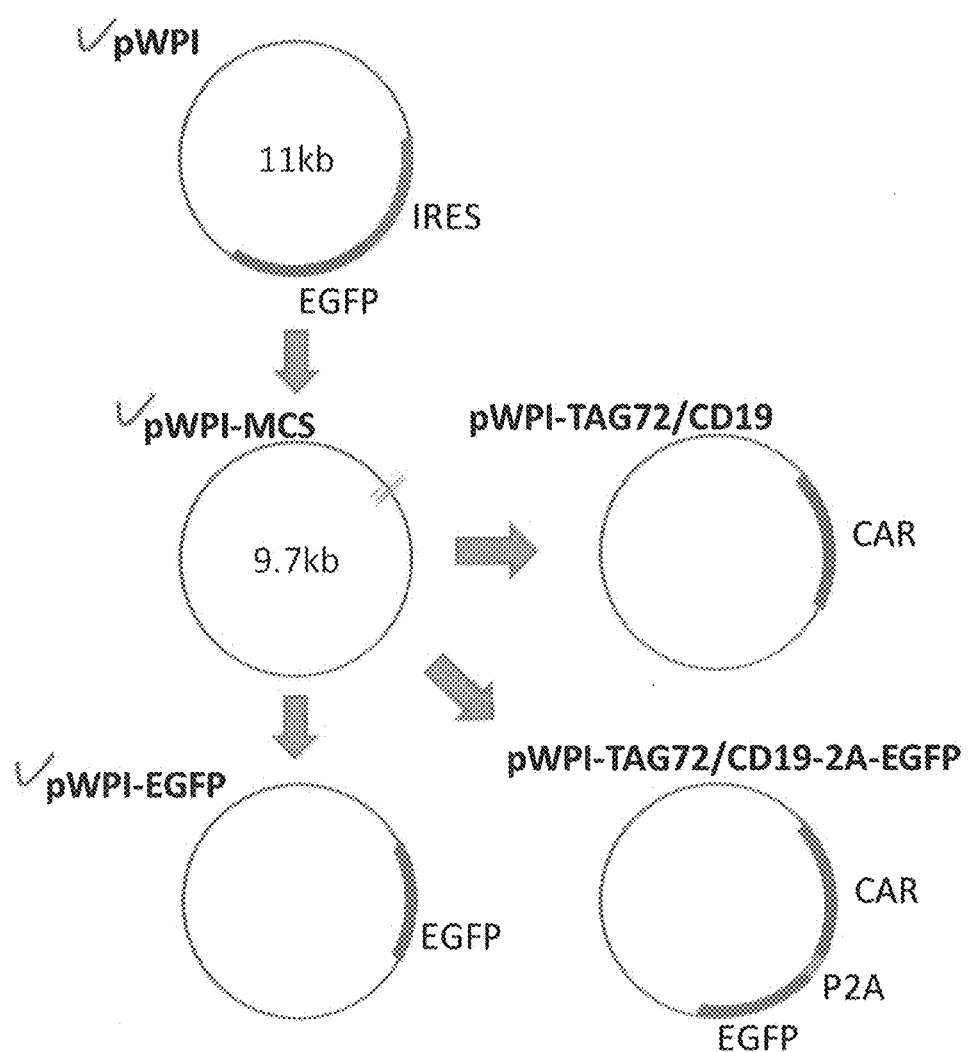

Figures 14A-14B
Schematic of a non-signalling antigen-binding receptor, a truncated CD47 "attachment stalk"
A  2$^{nd}$ Generation CAR
B  CD47 attachment stalk
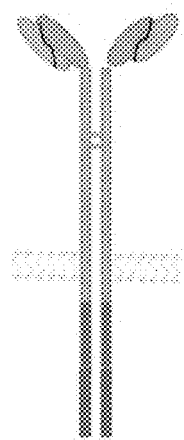
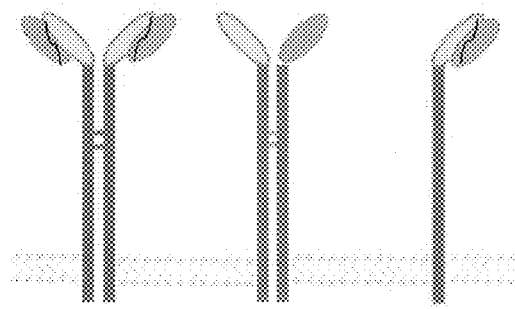
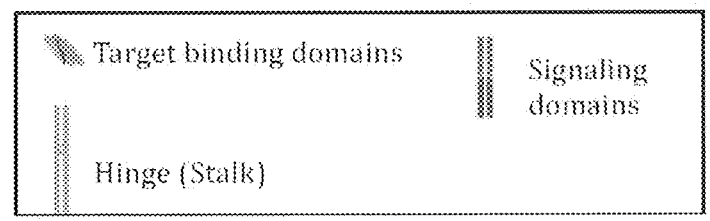

Flow cytometry analysis of CAR-transduced human PBMC-derived CD3+ T cells

Western blot analysis confirming protein expression in TAG72 and CD19 CAR-transfected T cells Western blot analysis of Tag72-CAR and CD19-CAR transduced human T cells under reducing (+) and non-reducing condition (-). It shows that the CARs are present as both covalent dimers and monomers within T cells.

TAG-72 CAR-T mediated killing of ovarian cancer cell line

Specificity of TAG-72 CAR-T killing

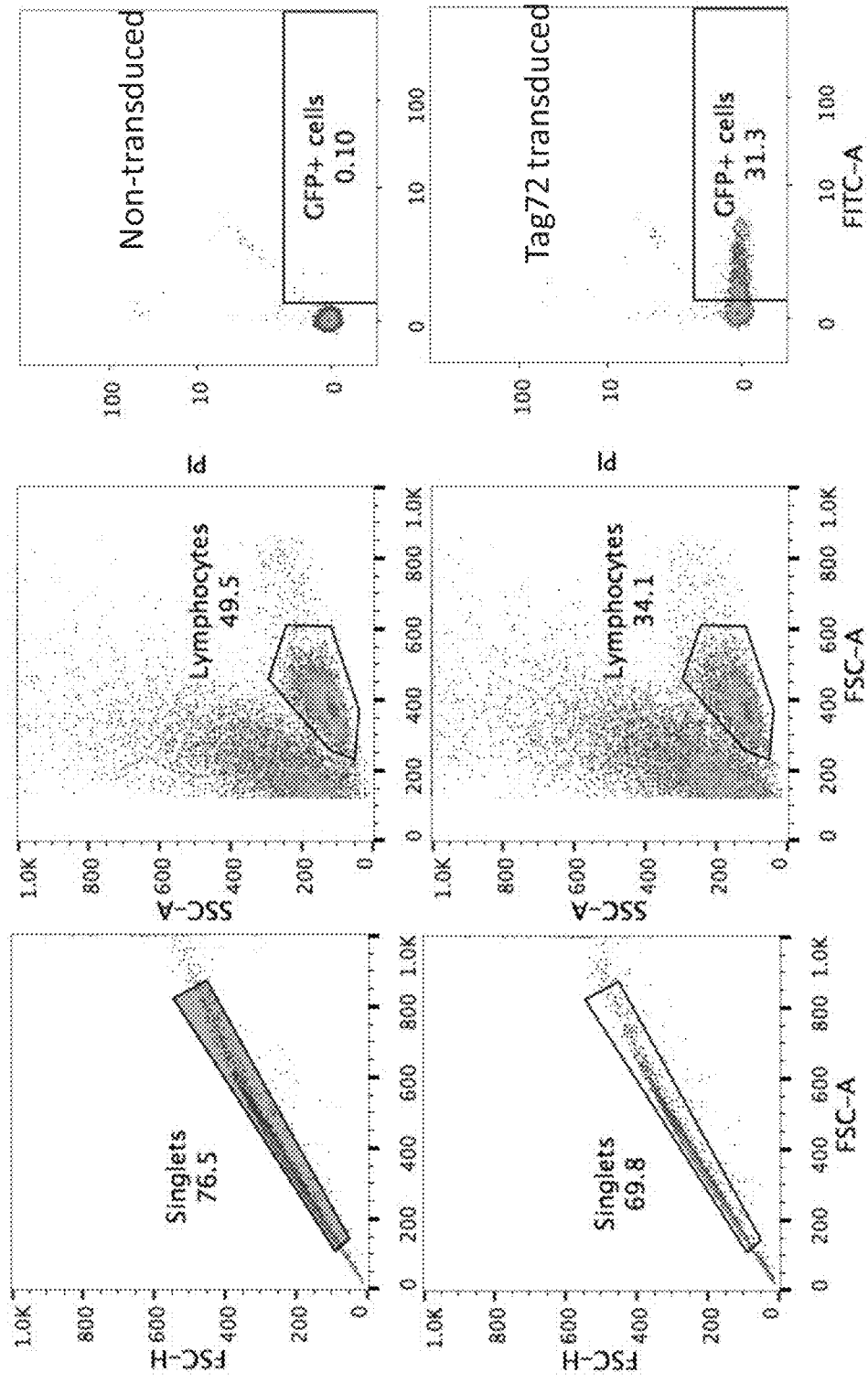
Figure 19A: Successful transduction of WT-1 specific TCR cytotoxic T cells derived from iPSCs produced from WT-1 specific TCR, with a CAR construct encoding TAG72

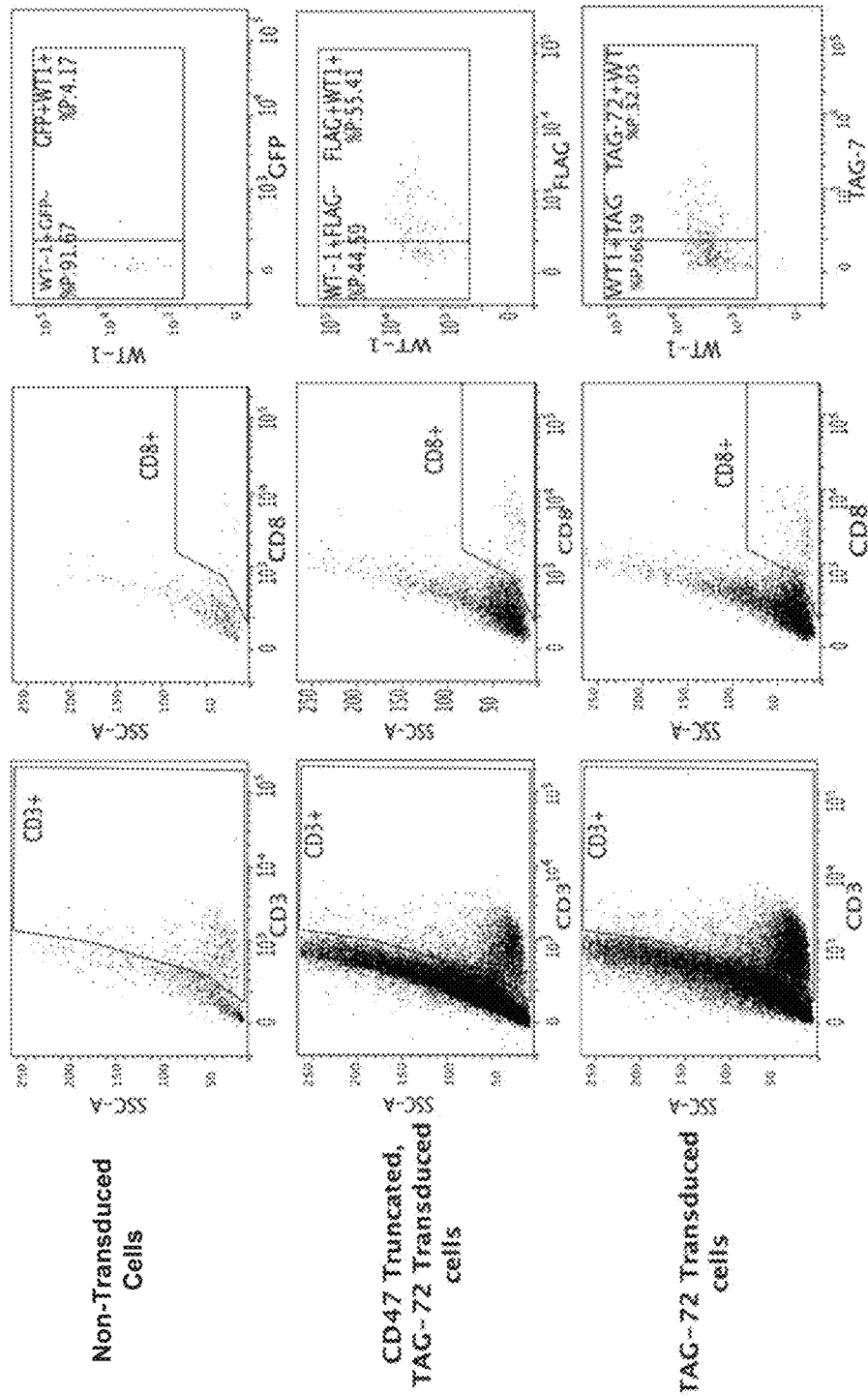
Figure 19B. Successful transduction of WT-1 specific TCR cytotoxic T cells derived from iPSC produced from WT-1 specific TCR T cells, with a CAR construct encoding TAG72 and truncated (non-signalling) CD47, as well as a TAG72 alone viral vector. Values are expressed as a percentage of CD8+ T cells.

Cytotoxicity of WT-1 TCR T cells, and dual specific TAG-72 CAR/WT-1 TCR T cells

TAG 72 CAR transduction of iPSC derived from WT-1 Tcells

Flow cytometric analysis of Chimeric Antigen Receptor transduced iPSC

Overlay of dot plots comparing non-transduced control cells (blue) to CAR transduced iPSC cultures (green)

```
                        SEQUENCE LISTING

<160> NUMBER OF SEQ ID NOS: 25

<210> SEQ ID NO 1
<211> LENGTH: 2670
<212> TYPE: DNA
<213> ORGANISM: Artificial Sequence
<220> FEATURE:
<223> OTHER INFORMATION: DNA coding for TAG72 CAR-P2A-CD47 binding
      receptor

<400> SEQUENCE: 1
atggagttcg gcctgcgctg ggtgttcctg gtggccatcc tgaaggacgt gcagtgccag      60
gtgcagctgc agcagagcga cgccgagctg gtgaagcccg gcgccagcgt gaagatcagc     120
tgcaaggcca gcggctacac cttcaccgac cacgccatcc actgggtgaa gcagaacccc     180
gagcagggcc tggagtggat cggctacttc agccccggca acgacgactt caagtacaac     240
gagcgcttca agggcaaggc caccctgacc gccgacaaga gcagcagcac cgcctacctg     300
cagctgaaca gcctgaccag cgaggacagc gccgtgtact tctgcacccg cagcctgaac     360
atggcctact ggggccaggg caccagcgtg accgtgagca gcggcggcgg cggcagcggc     420
ggcggcggca gcggcggcgg cggcagcgac atcgtgatga cccagagccc cagcagcctg     480
cccgtgagcg tgggcgagaa ggtgaccctg agctgcaaga gcagccagag cctgctgtac     540
agcggcaacc agaagaacta cctggcctgg taccagcaga gcccggcca gagcccccaag     600 ctcctgatct actgggccag cacccgcgag agcggcgtgc ccgaccgctt caccggcagc     660
ggcagcggca ccgacttcac cctgagcatc agcagcgtgg agaccgagga cctggccgtg     720
tactactgcc agcagtacta cagctacccc ctgaccttcg gcgccggcac caagctggtg     780
ctgaagcgcg actacaagga cgacgacgac aagctgagca actccatcat gtacttcagc     840
cacttcgtgc cggtcttcct gccagcgaag cccaccacga cgccagcgcc gcgaccacca     900
acaccggcgc ccaccatcgc gtcgcagccc ctgtccctgc gcccagaggc gtgccggcca     960
gcggcggggg gcgcagtgca cacgaggggg ctgttttggg tgctggtggt ggttggtgga    1020
gtcctggctt gctatagctt gctagtaaca gtggccttta ttattttctg ggtgaggagt    1080
aagaggagca ggctcctgca cagtgactac atgaacatga ctccccgccg ccccgggccc    1140
acccgcaagc attaccagcc ctatgcccca ccacgcgact cgcagcccta tcgctccaga    1200
gtgaagttca gcaggagcgc agacgccccc ggcgtaccagc agggccagaa ccagctctat    1260
aacgagctca atctaggacg aagagaggag tacgatgttt tggacaagag acgtggccgg    1320
```

```
gaccctgaga tgggggggaaa gccgagaagg aagaaccctc aggaaggcct gtacaatgaa    1380
ctgcagaaag ataagatggc ggaggcctac agtgagattg ggatgaaagg cgagcgccgg    1440
aggggcaagg ggcacgatgg cctttaccag ggtctcagta cagccaccaa ggacacctac    1500 gacgccttc acatgcaggc cctgcccct cgcgtcgacg aagcggagc tactaacttc      1560 agcctgctga agcaggctgg agacgtggag gagaaccctg acctatggc cctgcccgtg    1620 accgccctgc tgctgcccct ggccctgctg ctgcacgccg cccgcgccca ggtgcagctg    1680
gtgcagagcg gcgccgaggt gaagaagccc ggcgccagct gaaggtgag ctgcaaggcc    1740 agcggctaca ccttcaccaa ctacaacatg cactgggtgc gccaggcccc cggccagcgc    1800
ctggagtgga tgggcaccat ctaccccggc aacgacgaca ccagctacaa ccagaagttc    1860
aaggaccgcg tgaccatcac cgccgacacc agcgccagca ccgcctacat ggagctgagc    1920
agcctgcgca gcgaggacac cgccgtgtac tactgcgccc gggcggcta ccgcgccatg    1980 gactactggg gccagggcac cctggtgacc gtgagcagcg gcggaggcgg aagcggaggc    2040
ggaggcagcg ggggcggcgg aagcgacatc gtgatgaccc agagccccct gagcctgccc    2100 gtgaccccg cgagcccgc cagcatcagc tgccgcagca gcagagcat cgtgtacagc      2160 aacggcaaca cctacctggg ctggtacctg cagaagcccg gccagagccc ccagctgctg    2220
atctacaagg tgagcaaccg cttcagcggc gtgcccgacc gcttcagcgg cagcggcagc    2280
ggcaccgact tcaccctgaa gatcagccgc gtggaggccg aggacgtggg cgtgtactac    2340
tgcttccagg gcagccacgt gccctacacc ttcggccagg gcaccaagct ggagatcaag    2400
gccgccgagc agaagctgat cagcgaggag gacctgatcg aggtgatgta ccccccccc    2460 tacctggaca cgagaagag caacggcacc atcatccacg tgaagggcaa gcacctgtgc    2520
cccagccccc tgttccccgg ccccagcaag cccttctggg tgctggtggt ggtgggcggc    2580
gtgctggcct gctacagcct gctggtgacc gtggccttca tcatcttctg ggtgcgcagc    2640
aagcgcagcc gcctgctgca cagcgactaa                                     2670
```

<210> SEQ ID NO 2
<211> LENGTH: 889
<212> TYPE: PRT
<213> ORGANISM: Artificial Sequence
<220> FEATURE:
<223> OTHER INFORMATION: Protein sequence of TAG72 CAR-P2A-CD47 binding
      receptor
<220> FEATURE:
<221> NAME/KEY: misc_feature
<222> LOCATION: (1)..(19)
<223> OTHER INFORMATION: Kappa leader
<220> FEATURE:
<221> NAME/KEY: misc_feature
<222> LOCATION: (20)..(134)
<223> OTHER INFORMATION: anti-TAG72 VH
<220> FEATURE:
<221> NAME/KEY: misc_feature
<222> LOCATION: (135)..(149)
<223> OTHER INFORMATION: GS Linker
<220> FEATURE:
<221> NAME/KEY: misc_feature
<222> LOCATION: (150)..(263)
<223> OTHER INFORMATION: anti-TAG72 VL
<220> FEATURE:
<221> NAME/KEY: misc_feature
<222> LOCATION: (264)..(272)
<223> OTHER INFORMATION: FLAG epitope
<220> FEATURE:
<221> NAME/KEY: misc_feature
<222> LOCATION: (273)..(331)
<223> OTHER INFORMATION: CD8 hinge
<220> FEATURE:

```
<221> NAME/KEY: misc_feature
<222> LOCATION: (332)..(358)
<223> OTHER INFORMATION: CD28 TM
<220> FEATURE:
<221> NAME/KEY: misc_feature
<222> LOCATION: (359)..(399)
<223> OTHER INFORMATION: CD28 Signalling domain
<220> FEATURE:
<221> NAME/KEY: misc_feature
<222> LOCATION: (400)..(513)
<223> OTHER INFORMATION: TCR3-zeta Signalling domain
<220> FEATURE:
<221> NAME/KEY: misc_feature
<222> LOCATION: (514)..(535)
<223> OTHER INFORMATION: P2A self cleaving peptide
<220> FEATURE:
<221> NAME/KEY: misc_feature
<222> LOCATION: (536)..(556)
<223> OTHER INFORMATION: CD8a leader
<220> FEATURE:
<221> NAME/KEY: misc_feature
<222> LOCATION: (557)..(673)
<223> OTHER INFORMATION: anti-CD47 VH
<220> FEATURE:
<221> NAME/KEY: misc_feature
<222> LOCATION: (674)..(688)
<223> OTHER INFORMATION: GS linker
<220> FEATURE:
<221> NAME/KEY: misc_feature
<222> LOCATION: (689)..(800)
<223> OTHER INFORMATION: anti-CD47 VL
<220> FEATURE:
<221> NAME/KEY: misc_feature
<222> LOCATION: (801)..(812)
<223> OTHER INFORMATION: c-Myc epitope
<220> FEATURE:
<221> NAME/KEY: misc_feature
<222> LOCATION: (813)..(851)
<223> OTHER INFORMATION: CD28 hinge
<220> FEATURE:
<221> NAME/KEY: misc_feature
<222> LOCATION: (852)..(878)
<223> OTHER INFORMATION: CD28 TM
<220> FEATURE:
<221> NAME/KEY: misc_feature
<222> LOCATION: (879)..(889)
<223> OTHER INFORMATION: cytoplasmic tail derived from CD28

<400> SEQUENCE: 2

Met Glu Phe Gly Leu Arg Trp Val Phe Leu Val Ala Ile Leu Lys Asp
1               5                  10                  15

Val Gln Cys Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Asn Pro Glu Gln Gly Leu
    50                  55                  60

Glu Trp Ile Gly Tyr Phe Ser Pro Gly Asn Asp Asp Phe Lys Tyr Asn
65                  70                  75                  80

Glu Arg Phe Lys Gly Lys Ala Thr Leu Thr Ala Asp Lys Ser Ser Ser
                85                  90                  95

Thr Ala Tyr Leu Gln Leu Asn Ser Leu Thr Ser Glu Asp Ser Ala Val
            100                 105                 110

Tyr Phe Cys Thr Arg Ser Leu Asn Met Ala Tyr Trp Gly Gln Gly Thr
        115                 120                 125

Ser Val Thr Val Ser Ser Gly Gly Gly Gly Ser Gly Gly Gly Gly Ser
    130                 135                 140

Gly Gly Gly Gly Ser Asp Ile Val Met Thr Gln Ser Pro Ser Ser Leu
145                 150                 155                 160
```

```
Pro Val Ser Val Gly Glu Lys Val Thr Leu Ser Cys Lys Ser Ser Gln
                165                 170                 175
Ser Leu Leu Tyr Ser Gly Asn Gln Lys Asn Tyr Leu Ala Trp Tyr Gln
            180                 185                 190
Gln Lys Pro Gly Gln Ser Pro Lys Leu Leu Ile Tyr Trp Ala Ser Thr
        195                 200                 205
Arg Glu Ser Gly Val Pro Asp Arg Phe Thr Gly Ser Gly Ser Gly Thr
    210                 215                 220
Asp Phe Thr Leu Ser Ile Ser Ser Val Glu Thr Glu Asp Leu Ala Val
225                 230                 235                 240
Tyr Tyr Cys Gln Gln Tyr Tyr Ser Tyr Pro Leu Thr Phe Gly Ala Gly
                245                 250                 255
Thr Lys Leu Val Leu Lys Arg Asp Tyr Lys Asp Asp Asp Asp Lys Leu
            260                 265                 270
Ser Asn Ser Ile Met Tyr Phe Ser His Phe Val Pro Val Phe Leu Pro
        275                 280                 285
Ala Lys Pro Thr Thr Thr Pro Ala Pro Arg Pro Pro Thr Pro Ala Pro
    290                 295                 300
Thr Ile Ala Ser Gln Pro Leu Ser Leu Arg Pro Glu Ala Cys Arg Pro
305                 310                 315                 320
Ala Ala Gly Gly Ala Val His Thr Arg Gly Leu Phe Trp Val Leu Val
                325                 330                 335
Val Val Gly Gly Val Leu Ala Cys Tyr Ser Leu Leu Val Thr Val Ala
            340                 345                 350
Phe Ile Ile Phe Trp Val Arg Ser Lys Arg Ser Arg Leu Leu His Ser
        355                 360                 365
Asp Tyr Met Asn Met Thr Pro Arg Arg Pro Gly Pro Thr Arg Lys His
    370                 375                 380
Tyr Gln Pro Tyr Ala Pro Pro Arg Asp Phe Ala Ala Tyr Arg Ser Arg
385                 390                 395                 400
Val Lys Phe Ser Arg Ser Ala Asp Ala Pro Ala Tyr Gln Gln Gly Gln
                405                 410                 415
Asn Gln Leu Tyr Asn Glu Leu Asn Leu Gly Arg Arg Glu Glu Tyr Asp
            420                 425                 430
Val Leu Asp Lys Arg Arg Gly Arg Asp Pro Glu Met Gly Gly Lys Pro
        435                 440                 445
Arg Arg Lys Asn Pro Gln Glu Gly Leu Tyr Asn Glu Leu Gln Lys Asp
    450                 455                 460
Lys Met Ala Glu Ala Tyr Ser Glu Ile Gly Met Lys Gly Glu Arg Arg
465                 470                 475                 480
Arg Gly Lys Gly His Asp Gly Leu Tyr Gln Gly Leu Ser Thr Ala Thr
                485                 490                 495
Lys Asp Thr Tyr Asp Ala Leu His Met Gln Ala Leu Pro Pro Arg Val
            500                 505                 510
Asp Gly Ser Gly Ala Thr Asn Phe Ser Leu Leu Lys Gln Ala Gly Asp
        515                 520                 525
Val Glu Glu Asn Pro Gly Pro Met Ala Leu Pro Val Thr Ala Leu Leu
    530                 535                 540
Leu Pro Leu Ala Leu Leu Leu His Ala Ala Arg Ala Gln Val Gln Leu
545                 550                 555                 560
Val Gln Ser Gly Ala Glu Val Lys Lys Pro Gly Ala Ser Val Lys Val
                565                 570                 575
```

-continued

```
Ser Cys Lys Ala Ser Gly Tyr Thr Phe Thr Asn Tyr Asn Met His Trp
            580                 585                 590

Val Arg Gln Ala Pro Gly Gln Arg Leu Glu Trp Met Gly Thr Ile Tyr
        595                 600                 605

Pro Gly Asn Asp Asp Thr Ser Tyr Asn Gln Lys Phe Lys Asp Arg Val
    610                 615                 620

Thr Ile Thr Ala Asp Thr Ser Ala Ser Thr Ala Tyr Met Glu Leu Ser
625                 630                 635                 640

Ser Leu Arg Ser Glu Asp Thr Ala Val Tyr Tyr Cys Ala Arg Gly Gly
                645                 650                 655

Tyr Arg Ala Met Asp Tyr Trp Gly Gln Gly Thr Leu Val Thr Val Ser
            660                 665                 670

Ser Gly Gly Gly Gly Ser Gly Gly Gly Gly Ser Gly Gly Gly Gly Ser
        675                 680                 685

Asp Ile Val Met Thr Gln Ser Pro Leu Ser Leu Pro Val Thr Pro Gly
    690                 695                 700

Glu Pro Ala Ser Ile Ser Cys Arg Ser Ser Gln Ser Ile Val Tyr Ser
705                 710                 715                 720

Asn Gly Asn Thr Tyr Leu Gly Trp Tyr Leu Gln Lys Pro Gly Gln Ser
                725                 730                 735

Pro Gln Leu Leu Ile Tyr Lys Val Ser Asn Arg Phe Ser Gly Val Pro
            740                 745                 750

Asp Arg Phe Ser Gly Ser Gly Ser Gly Thr Asp Phe Thr Leu Lys Ile
        755                 760                 765

Ser Arg Val Glu Ala Glu Asp Val Gly Val Tyr Tyr Cys Phe Gln Gly
    770                 775                 780

Ser His Val Pro Tyr Thr Phe Gly Gln Gly Thr Lys Leu Glu Ile Lys
785                 790                 795                 800

Ala Ala Glu Gln Lys Leu Ile Ser Glu Glu Asp Leu Ile Glu Val Met
                805                 810                 815

Tyr Pro Pro Pro Tyr Leu Asp Asn Glu Lys Ser Asn Gly Thr Ile Ile
            820                 825                 830

His Val Lys Gly Lys His Leu Cys Pro Ser Pro Leu Phe Pro Gly Pro
        835                 840                 845

Ser Lys Pro Phe Trp Val Leu Val Val Val Gly Gly Val Leu Ala Cys
    850                 855                 860

Tyr Ser Leu Leu Val Thr Val Ala Phe Ile Ile Phe Trp Val Arg Ser
865                 870                 875                 880

Lys Arg Ser Arg Leu Leu His Ser Asp
                885
```

<210> SEQ ID NO 3
<211> LENGTH: 1062
<212> TYPE: DNA
<213> ORGANISM: Artificial Sequence
<220> FEATURE:
<223> OTHER INFORMATION: DNA coding for CD47-binding receptor

<400> SEQUENCE: 3

```
atggccctgc ccgtgaccgc cctgctgctg cccctggccc tgctgctgca cgccgcccgc      60
gcccaggtgc agctggtgca gagcggcgcc gaggtgaaga agcccggcgc cagcgtgaag     120
gtgagctgca aggccagcgg ctacaccttc accaactaca acatgcactg ggtgcgccag     180
gcccccggcc agcgcctgga gtggatgggc accatctacc ccggcaacga cgacaccagc     240
tacaaccaga agttcaagga ccgcgtgacc atcaccgccg acaccagcgc cagcaccgcc     300
```

```
tacatggagc tgagcagcct gcgcagcgag gacaccgccg tgtactactg cgcccgcggc    360
ggctaccgcg ccatggacta ctggggccag ggcaccctgg tgaccgtgag cagcggcgga    420
ggcggaagcg gaggcggagg cagcgggggc ggcggaagcg acatcgtgat gacccagagc    480
cccctgagcc tgcccgtgac ccccggcgag cccgccagca tcagctgccg cagcagccag    540
agcatcgtgt acagcaacgg caacacctac ctgggctggt acctgcagaa gcccggccag    600
agcccccagc tgctgatcta caaggtgagc aaccgcttca gcggcgtgcc cgaccgcttc    660
agcggcagcg gcagcggcac cgacttcacc ctgaagatca gccgcgtgga ggccgaggac    720
gtgggcgtgt actactgctt ccagggcagc cacgtgccct acaccttcgg ccagggcacc    780
aagctggaga tcaaggccgc cgagcagaag ctgatcagcg aggaggacct gatcgaggtg    840
atgtaccccc cccctacct ggacaacgag aagagcaacg gcaccatcat ccacgtgaag    900
ggcaagcacc tgtgccccag ccccctgttc ccggcccca gcaagccctt ctgggtgctg    960
gtggtggtgg gcggcgtgct ggcctgctac agcctgctgg tgaccgtggc cttcatcatc   1020
ttctgggtgc gcagcaagcg cagccgcctg ctgcacagcg ac                      1062
```

<210> SEQ ID NO 4
<211> LENGTH: 354
<212> TYPE: PRT
<213> ORGANISM: Artificial Sequence
<220> FEATURE:
<223> OTHER INFORMATION: Protein sequence of CD47-binding receptor
<220> FEATURE:
<221> NAME/KEY: misc_feature
<222> LOCATION: (1)..(21)
<223> OTHER INFORMATION: CD8a leader
<220> FEATURE:
<221> NAME/KEY: misc_feature
<222> LOCATION: (22)..(138)
<223> OTHER INFORMATION: anti-CD47 VH
<220> FEATURE:
<221> NAME/KEY: misc_feature
<222> LOCATION: (139)..(153)
<223> OTHER INFORMATION: GS linker
<220> FEATURE:
<221> NAME/KEY: misc_feature
<222> LOCATION: (154)..(265)
<223> OTHER INFORMATION: anti-CD47 VL
<220> FEATURE:
<221> NAME/KEY: misc_feature
<222> LOCATION: (266)..(277)
<223> OTHER INFORMATION: c-Myc epitope
<220> FEATURE:
<221> NAME/KEY: misc_feature
<222> LOCATION: (278)..(316)
<223> OTHER INFORMATION: CD28 hinge
<220> FEATURE:
<221> NAME/KEY: misc_feature
<222> LOCATION: (317)..(343)
<223> OTHER INFORMATION: CD28 TM
<220> FEATURE:
<221> NAME/KEY: misc_feature
<222> LOCATION: (344)..(354)
<223> OTHER INFORMATION: cytoplasmic tail derived from CD28

<400> SEQUENCE: 4

Met Ala Leu Pro Val Thr Ala Leu Leu Leu Pro Leu Ala Leu Leu Leu
1               5                   10                  15

His Ala Ala Arg Ala Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Asn Tyr Asn Met His Trp Val Arg Gln Ala Pro Gly Gln

-continued

```
    50                  55                  60

Arg Leu Glu Trp Met Gly Thr Ile Tyr Pro Gly Asn Asp Asp Thr Ser
65                  70                  75                  80

Tyr Asn Gln Lys Phe Lys Asp Arg Val Thr Ile Thr Ala Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Gly Gly Tyr Arg Ala Met Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Asp Ile Val Met Thr Gln Ser
145                 150                 155                 160

Pro Leu Ser Leu Pro Val Thr Pro Gly Glu Pro Ala Ser Ile Ser Cys
                165                 170                 175

Arg Ser Ser Gln Ser Ile Val Tyr Ser Asn Gly Asn Thr Tyr Leu Gly
            180                 185                 190

Trp Tyr Leu Gln Lys Pro Gly Gln Ser Pro Gln Leu Leu Ile Tyr Lys
        195                 200                 205

Val Ser Asn Arg Phe Ser Gly Val Pro Asp Arg Phe Ser Gly Ser Gly
    210                 215                 220

Ser Gly Thr Asp Phe Thr Leu Lys Ile Ser Arg Val Glu Ala Glu Asp
225                 230                 235                 240

Val Gly Val Tyr Tyr Cys Phe Gln Gly Ser His Val Pro Tyr Thr Phe
                245                 250                 255

Gly Gln Gly Thr Lys Leu Glu Ile Lys Ala Ala Glu Gln Lys Leu Ile
            260                 265                 270

Ser Glu Glu Asp Leu Ile Glu Val Met Tyr Pro Pro Pro Tyr Leu Asp
        275                 280                 285

Asn Glu Lys Ser Asn Gly Thr Ile Ile His Val Lys Gly Lys His Leu
    290                 295                 300

Cys Pro Ser Pro Leu Phe Pro Gly Pro Ser Lys Pro Phe Trp Val Leu
305                 310                 315                 320

Val Val Val Gly Gly Val Leu Ala Cys Tyr Ser Leu Leu Val Thr Val
                325                 330                 335

Ala Phe Ile Ile Phe Trp Val Arg Ser Lys Arg Ser Arg Leu Leu His
            340                 345                 350

Ser Asp
```

<210> SEQ ID NO 5
<211> LENGTH: 1065
<212> TYPE: DNA
<213> ORGANISM: Artificial Sequence
<220> FEATURE:
<223> OTHER INFORMATION: DNA coding for CD47-binding receptor with C to S substitution

<400> SEQUENCE: 5

```
atggccctgc ccgtgaccgc cctgctgctg cccctggccc tgctgctgca cgccgcccgc     60
gcccaggtgc agctggtgca gagcggcgcc gaggtgaaga agcccggcgc cagcgtgaag    120
gtgagctgca aggccagcgg ctacaccttc accaactaca acatgcactg ggtgcgccag    180
gcccccggcc agcgcctgga gtggatgggc accatctacc ccggcaacga cgacaccagc    240
tacaaccaga agttcaagga ccgcgtgacc atcaccgccg acaccagcgc cagcaccgcc    300
```

```
tacatggagc tgagcagcct gcgcagcgag gacaccgccg tgtactactg cgcccgcggc    360
ggctaccgcg ccatggacta ctggggccag ggcaccctgg tgaccgtgag cagcggcgga    420
ggcggaagcg gaggcggagg cagcggggc ggcggaagcg acatcgtgat gacccagagc    480
cccctgagcc tgcccgtgac ccccggcgag cccgccagca tcagctgccg cagcagccag    540
agcatcgtgt acagcaacgg caacacctac ctgggctggt acctgcagaa gcccggccag    600
agcccccagc tgctgatcta caaggtgagc aaccgcttca gcggcgtgcc cgaccgcttc    660
agcggcagcg gcagcggcac cgacttcacc ctgaagatca gccgcgtgga ggccgaggac    720
gtgggcgtgt actactgctt ccagggcagc cacgtgccct acaccttcgg ccagggcacc    780
aagctggaga tcaaggccgc cgagcagaag ctgatcagcg aggaggacct gatcgaggtg    840
atgtaccccc ccccctacct ggacaacgag aagagcaacg gcaccatcat ccacgtgaag    900
ggcaagcacc tgagccccag ccccctgttc cccggcccca gcaagccctt ctgggtgctg    960
gtggtggtgg gcggcgtgct ggccagctac agcctgctgg tgaccgtggc cttcatcatc   1020
ttctgggtgc gcagcaagcg cagccgcctg ctgcacagcg actaa                    1065
```

<210> SEQ ID NO 6
<211> LENGTH: 354
<212> TYPE: PRT
<213> ORGANISM: Artificial Sequence
<220> FEATURE:
<223> OTHER INFORMATION: Protein sequence of CD47-binding receptor with C to S substitution

<400> SEQUENCE: 6

```
Met Ala Leu Pro Val Thr Ala Leu Leu Leu

Ser Gly Thr Asp Phe Thr Leu Lys Ile Ser Arg Val Glu Ala Glu Asp
225                 230                 235                 240

Val Gly Val Tyr Tyr Cys Phe Gln Gly Ser His Val Pro Tyr Thr Phe
            245                 250                 255

Gly Gln Gly Thr Lys Leu Glu Ile Lys Ala Ala Glu Gln Lys Leu Ile
        260                 265                 270

Ser Glu Glu Asp Leu Ile Glu Val Met Tyr Pro Pro Pro Tyr Leu Asp
        275                 280                 285

Asn Glu Lys Ser Asn Gly Thr Ile Ile His Val Lys Gly Lys His Leu
        290                 295                 300

Ser Pro Ser Pro Leu Phe Pro Gly Pro Ser Lys Pro Phe Trp Val Leu
305                 310                 315                 320

Val Val Val Gly Gly Val Leu Ala Ser Tyr Ser Leu Leu Val Thr Val
            325                 330                 335

Ala Phe Ile Ile Phe Trp Val Arg Ser Lys Arg Ser Arg Leu Leu His
            340                 345                 350

Ser Asp

<210> SEQ ID NO 7
<211> LENGTH: 732
<212> TYPE: DNA
<213> ORGANISM: Artificial Sequence
<220> FEATURE:
<223> OTHER INFORMATION: DNA coding for TAG72 scFV

<400> SEQUENCE: 7
caggtgcagc tgcagcagag cgacgccgag ctggtgaagc ccggcgccag cgtgaagatc     60
agctgcaagg ccagcggcta caccttcacc gaccacgcca tccactgggt gaagcagaac    120
cccgagcagg gcctggagtg gatcggctac ttcagccccg caacgacga cttcaagtac    180 aacgagcgct tcaagggcaa ggccaccctg accgccgaca agagcagcag caccgcctac    240
ctgcagctga acagcctgac cagcgaggac agcgccgtgt acttctgcac cgcagcctg     300 aacatggcct actggggcca gggcaccagc gtgaccgtga gcagcggcgg cggcggcagc    360
ggcggcggcg gcagcggcgg cggcggcagc gacatcgtga tgacccagag ccccagcagc    420
ctgcccgtga gcgtgggcga aaggtgacc ctgagctgca gagcagcca gagcctgctg     480 tacagcggca accagaagaa ctacctggcc tggtaccagc agaagcccgg ccagagcccc    540
aagctcctga tctactgggc cagcacccgc gagagcggcg tgcccgaccg cttcaccggc    600
agcggcagcg gcaccgactt caccctgagc atcagcagcg tggagaccga ggacctggcc    660
gtgtactact gccagcagta ctacagctac ccctgacct tcggcgccgg caccaagctg    720
gtgctgaagc gc                                                        732

<210> SEQ ID NO 8
<211> LENGTH: 244
<212> TYPE: PRT
<213> ORGANISM: Artificial Sequence
<220> FEATURE:
<223> OTHER INFORMATION: Protein sequence of TAG72 scFV

<400> SEQUENCE: 8

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile

```
                35                  40                  45
Gly Tyr Phe Ser Pro Gly Asn Asp Asp Phe Lys Tyr Asn Glu Arg Phe
 50                  55                  60
Lys Gly Lys Ala Thr Leu Thr Ala Asp Lys Ser Ser Thr Ala Tyr
 65                  70                  75                  80
Leu Gln Leu Asn Ser Leu Thr Ser Glu Asp Ser Ala Val Tyr Phe Cys
                 85                  90                  95
Thr Arg Ser Leu Asn Met Ala Tyr Trp Gly Gln Gly Thr Ser Val Thr
            100                 105                 110
Val Ser Ser Gly Gly Gly Gly Ser Gly Gly Gly Gly Ser Gly Gly Gly
            115                 120                 125
Gly Ser Asp Ile Val Met Thr Gln Ser Pro Ser Ser Leu Pro Val Ser
            130                 135                 140
Val Gly Glu Lys Val Thr Leu Ser Cys Lys Ser Ser Gln Ser Leu Leu
145                 150                 155                 160
Tyr Ser Gly Asn Gln Lys Asn Tyr Leu Ala Trp Tyr Gln Gln Lys Pro
                165                 170                 175
Gly Gln Ser Pro Lys Leu Leu Ile Tyr Trp Ala Ser Thr Arg Glu Ser
            180                 185                 190
Gly Val Pro Asp Arg Phe Thr Gly Ser Gly Ser Gly Thr Asp Phe Thr
            195                 200                 205
Leu Ser Ile Ser Ser Val Glu Thr Glu Asp Leu Ala Val Tyr Tyr Cys
            210                 215                 220
Gln Gln Tyr Tyr Ser Tyr Pro Leu Thr Phe Gly Ala Gly Thr Lys Leu
225                 230                 235                 240
Val Leu Lys Arg

<210> SEQ ID NO 9
<211> LENGTH: 117
<212> TYPE: PRT
<213> ORGANISM: Artificial Sequence
<220> FEATURE:
<223> OTHER INFORMATION: Protein sequence of Hu5F9 VH-2 (CD47)

<400> SEQUENCE: 9

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asn Tyr
             20                  25                  30
Asn Met His Trp Val Arg Gln Ala Pro Gly Gln Arg Leu Glu Trp Met
             35                  40                  45
Gly Thr Ile Tyr Pro Gly Asn Asp Asp Thr Ser Tyr Asn Gln Lys Phe
 50                  55                  60
Lys Asp Arg Val Thr Ile Thr Ala Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Arg Ala Met Asp Tyr Trp Gly Gln Gly Thr Leu
            100                 105                 110
Val Thr Val Ser Ser
            115

<210> SEQ ID NO 10
<211> LENGTH: 112
<212> TYPE: PRT
<213> ORGANISM: Artificial Sequence
```

<220> FEATURE:
<223> OTHER INFORMATION: Protein sequence of Hu5F9 VL-12

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 11
<211> LENGTH: 244
<212> TYPE: PRT
<213> ORGANISM: Artificial Sequence
<220> FEATURE:
<223> OTHER INFORMATION: Protein sequence of scFv for CD47 Attachment
      stalk

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Ile Val Tyr Ser Asn Gly Asn Thr Tyr Leu Gly Trp Tyr Leu Gln Lys
                165                 170                 175

Pro Gly Gln Ser Pro Gln Leu Leu Ile Tyr Lys Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

```
Cys Phe Gln Gly Ser His Val Pro Tyr Thr Phe Gly Gln Gly Thr Lys
225                 230                 235                 240

Leu Glu Ile Lys

<210> SEQ ID NO 12
<211> LENGTH: 60
<212> TYPE: PRT
<213> ORGANISM: Artificial Sequence
<220> FEATURE:
<223> OTHER INFORMATION: CD8 hinge protein sequence

<400> SEQUENCE: 12

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
                20                  25                  30

Pro Thr Ile Ala Ser Gln Pro Leu Ser Leu Arg Pro Glu Ala Cys Arg
            35                  40                  45

Pro Ala Ala Gly Gly Ala Val His Thr Arg Gly Leu
        50                  55                  60

<210> SEQ ID NO 13
<211> LENGTH: 24
<212> TYPE: PRT
<213> ORGANISM: Artificial Sequence
<220> FEATURE:
<223> OTHER INFORMATION: CD8 TM protein sequence

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 14
<211> LENGTH: 39
<212> TYPE: PRT
<213> ORGANISM: Artificial Sequence
<220> FEATURE:
<223> OTHER INFORMATION: CD28 hinge protein sequence

<400> SEQUENCE: 14

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro
            35

<210> SEQ ID NO 15
<211> LENGTH: 39
<212> TYPE: PRT
<213> ORGANISM: Artificial Sequence
<220> FEATURE:
<223> OTHER INFORMATION: CD28 hinge protein sequence with C to S
      substitution

<400> SEQUENCE: 15

Ile Glu Val Met Tyr Pro Pro Pro Tyr Leu Asp Asn Glu Lys Ser Asn
1               5                   10                  15

Gly Thr Ile Ile His Val Lys Gly Lys His Leu Ser Pro Ser Pro Leu
                20                  25                  30
```

```
Phe Pro Gly Pro Ser Lys Pro
        35

<210> SEQ ID NO 16
<211> LENGTH: 27
<212> TYPE: PRT
<213> ORGANISM: Artificial Sequence
<220> FEATURE:
<223> OTHER INFORMATION: CD28 TM protein sequence

<400> SEQUENCE: 16

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 17
<211> LENGTH: 27
<212> TYPE: PRT
<213> ORGANISM: Artificial Sequence
<220> FEATURE:
<223> OTHER INFORMATION: CD28 TM with C to S substitution

<400> SEQUENCE: 17

Phe Trp Val Leu Val Val Val Gly Gly Val Leu Ala Ser Tyr Ser Leu
1               5                   10                  15

Leu Val Thr Val Ala Phe Ile Ile Phe Trp Val
            20                  25

<210> SEQ ID NO 18
<211> LENGTH: 41
<212> TYPE: PRT
<213> ORGANISM: Artificial Sequence
<220> FEATURE:
<223> OTHER INFORMATION: CD28 signalling domain protein sequence

<400> SEQUENCE: 18

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 19
<211> LENGTH: 42
<212> TYPE: PRT
<213> ORGANISM: Artificial Sequence
<220> FEATURE:
<223> OTHER INFORMATION: 4-1BB signalling domain protein sequence

<400> SEQUENCE: 19

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 20
<211> LENGTH: 112
<212> TYPE: PRT
<213> ORGANISM: Artificial Sequence
<220> FEATURE:
```

<223> OTHER INFORMATION: TCR zeta signalling domain protein sequence

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 22
<212> TYPE: PRT
<213> ORGANISM: Artificial Sequence
<220> FEATURE:
<223> OTHER INFORMATION: P2A protein sequence

<400> SEQUENCE: 21

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide WT-1(37)

<400> SEQUENCE: 22

Val Leu Asp Phe Ala Pro Pro Gly Ala
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide WT-1(126)

<400> SEQUENCE: 23

Arg Met Phe Pro Asn Ala Pro Tyr Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide WT-1(187)

<400> SEQUENCE: 24

Ser Leu Gly Glu Gln Gln Tyr Ser Val
1               5

```
<210> SEQ ID NO 25
<211> LENGTH: 9
<212> TYPE: PRT
<213> ORGANISM: Artificial Sequence
<220> FEATURE:
<223> OTHER INFORMATION: Synthetic peptide WT-1(235)

<400> SEQUENCE: 25

Cys Met Thr Trp Asn Gln Met Asn Leu
1               5
```

GENETICALLY MODIFIED CELLS AND USES THEREOF

This application claims the benefits of priority from Australian Provisional Patent Application No. 2015904933, filed Nov. 27, 2015, and No. 2016901328, filed Apr. 11, 2016, the entire contents of which are incorporated herein by reference.

FIELD OF THE INVENTION

The present invention relates generally to a population of stem cells (e.g., iPSCs or HSCs) that comprise nucleic acids encoding a T cell receptor and a chimeric antigen receptor directed to multiple distinct antigenic determinants, for example two distinct tumour antigenic determinants. The present invention is also directed to a population of T cells that co-express a T cell receptor and a chimeric antigen receptor directed to multiple distinct antigenic determinants, such as two distinct tumour antigenic determinants. The cells of the present invention can be derived from chosen donors whose HLA type is compatible with significant sectors of the populations, and are useful in a wide variety of applications, in particular in the context of the therapeutic treatment of neoplastic conditions.

INCORPORATION BY REFERENCE OF SEQUENCE LISTING

The Sequence Listing in an ASCII text file, named as 34247 Sequence Listing.txt of 36 KB, created on May 14, 2018, and submitted to the United States Patent and Trademark Office via EFS-Web, is incorporated herein by reference.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Malignant tumours, or cancers, grow in an uncontrolled manner, invade normal tissues, and often metastasize and grow at sites distant from the tissue of origin. In general, cancers are derived from one or only a few normal cells that have undergone a poorly understood process called malignant transformation. Cancers can arise from almost any tissue in the body. Those derived from epithelial cells, called carcinomas, are the most common kinds of cancers. Sarcomas are malignant tumours of mesenchymal tissues, arising from cells such as fibroblasts, muscle cells, and fat cells. Solid malignant tumours of lymphoid tissues are called lymphomas, and marrow and blood-borne malignant tumours of lymphocytes and other hematopoietic cells are called leukaemias.

Cancer is one of the three leading causes of death in industrialised nations. As treatments for infectious diseases and the prevention of cardiovascular disease continue to improve, and the average life expectancy increases, cancer is likely to become the most common fatal disease in these countries. Therefore, successfully treating cancer requires that all the malignant cells be removed or destroyed without killing the patient. An ideal way to achieve this would be to induce an immune response against the tumour that would discriminate between the cells of the tumour and their normal cellular counterparts. However, immunological approaches to the treatment of cancer have been attempted for over a century with unsustainable results.

Solid tumours cause the greatest number of deaths from cancer. Solid tumours are not usually curable once they have spread or 'metastasised' throughout the body. The prognosis of metastatic solid tumours has improved only marginally in the last 50 years. The best chance for the cure of a solid tumour relies on early detection followed by the use of local treatments such as surgery and/or radiotherapy when the solid tumour is localised and has not spread either to the lymph nodes that drain the tumour or elsewhere. Nonetheless, even at this early stage, and particularly if the tumour has spread to the draining lymph nodes, microscopic deposits of cancer known as micrometastases may have already spread throughout the body and will subsequently lead to the death of the patient. In this sense, cancer is a systemic disease that requires systemically administered treatments.

There is a long history of "Golden Bullet" attempts with toxin-loaded antibodies to attack cancers, taking advantage of their capacity to potentially target any specific molecular entity such as carbohydrate, lipid or protein, or combinations thereof. Antibodies, once bound to a cancer cell, can engage Complement or FcR+NK/K cells and induce cell lysis. Unfortunately antibody treatment of cancer has met generally only moderate success, primarily because of low affinity binding, poor lytic efficiency and their brief longevity. Collectively, these compromise the ability of antibodies to rapidly destroy cancer cells, increasing the risk of mutation and immune evasion. More recently, there have been reports of antibody-related therapies including those based on antibodies directed with high affinity to cancer molecules and to immune checkpoint blockade molecules. Although there are some clinical successes particularly with the latter, such therapies are still associated with various limitations.

Accordingly, common methods of treating cancer continue to follow the long used protocol of surgical excision (if possible) followed by radiotherapy and/or chemotherapy, if necessary. The success rate of this rather crude form of treatment is extremely variable but generally decreases significantly as the tumour becomes more advanced and metastasises. Further, these treatments are associated with severe side effects including disfigurement and scarring from surgery (eg. mastectomy or limb amputation), severe nausea and vomiting from chemotherapy, and most significantly, damage to normal tissues such as the hair follicles, gut and bone marrow which is induced as a result of the relatively non-specific targeting mechanism of the toxic drugs which form part of most cancer treatments.

Accordingly, there is an urgent and ongoing need to develop improved systemic therapies for cancers, in particular metastatic cancers.

Thymic generation of mainstream T cells is fundamentally required for defence against infection. This pool of "immune surveillance" T cells patrols the body to remove damaged or abnormal cells including cancers. Since thymus-based T cell production is characterised by random generation of the T cell receptor (TCR) repertoire, thymopoiesis must also include very strict selection processes that eliminate or functionally silence those developing thymus T cells with the potential to attack self. This "self tolerance" therefore restricts autoimmune disease (Fletcher et al (2011). However, by necessity, this very process compromises the immune surveillance against cancers—given that non-viral induced cancers are by definition diseases of "self". This means that many T cells arising in the thymus, which could potentially have been reactive with tumour-associated antigens may be eliminated before entry into the blood. At the very least they will be numerically deficient and perhaps have a low affinity TCR. Notwithstanding this, T cells are clearly potentially a major weapon against cancer—the challenges are thus to increase their ability to detect cancer, numerically expand them and retain, or better, enhance their powerful cytolytic capacity. While antibodies and T cells are the most logical weapons against cancer, their potential rapid and effective cancer destruction has not been clinically realized. Advances in immunotherapy have evolved through genetically engineering T cells to express a novel chimeric membrane receptor consisting of a cancer antigen binding antibody fragment, coupled cytoplasmically to T cell signal transduction molecules. The latter are commonly one or all of the TCR ζ chain, CD 28, or CD40-Ligand (Corrigan-Curay et al (2014); Fedorov et al (2014); Perna et al (2014); Curran et al (2015); Curran et al (2012); Dotti et al (2014); Han et al (2013)). Such chimeric antigen receptor (CAR) expressing T cells (CAR-T) not only harness the two most powerful anticancer weapons of the immune system, but also overcome their individual inadequacies. CAR-T retain the potent, focal, cell lytic capacity and avoid the normal reliance on the instrinsic TCR to detect very rare "cancer peptide(s)" expressed in HLA clefts. The repertoire of T cells specific to such nominal peptides is very rare. The antibody portion of the CAR endows the T cells with cancer seeking specificity and overcomes the notoriously poor cancer destructive efficacy of circulating antibodies. Thus cancer binding is mediated by the antibody domain of the CAR, leading to cytoplasmic signal transduction, triggering the T cell lytic pathways to destroy the cancer.

Although still in its clinical infancy, numerous CAR-T trials are underway. As promising as it is though, there are several aspects of CAR-T technology that are problematic and are preventing its clinical efficacy to be fully realized. The most obvious is the cytokine storm that occurs during T cell mediated cancer destruction and is tumour load dependent. Fever is indicative of cancer destruction, but can lead to severe clinical side effects unless managed carefully (Davila et al (2014); Casucci et al (2015)). Current management is by cytokine modulation treatments such as anti-IL6. Further, there exists a significant problem with the numerical deficiency of generated CAR-T cells to not only attack the initial cancer, but also to be preserved in sufficient supply in case of relapse. Currently, attempts to deal with this problem are based on the excessive use of proliferation inducing cytokines in vitro. Still further, as effective as CAR-T cells are at attacking cancer, even for CD19$^+$ cancers the tumour destruction is not 100% effective. While up to 90% responsiveness has been reported for B-ALL, in other CD19$^+$ cancers the results are much less effective. Accordingly, despite the encouraging observations in relation to the utility of CAR-T, there are still significant issues to be overcome before this technology can take its place as reliable, effective and the new gold standard in relation to cancer treatment.

In work leading up to the present invention it has been determined, inter alia, that the seemingly disparate problems currently existing in relation to the effective therapeutic application of CAR-T technology are resolvable where the CAR-T cells can be derived from transfected stem cells, such as adult stem cells, rather than transfected thymocytes or other transfected somatic cell types. For example, by transfecting stem cells (such as induced pluripotent stem cells ("iPSCs") derived from adult somatic cells) with a chimeric antigen receptor, the issue of providing sufficient present and future supplies of CAR-T cells directed to a particular tumour is resolved due to the ongoing source of somatic T cells derived from these self-renewing transfected stem cells. Still further, these iPSCs, and hence the CAR-T cells derived from them, can be prior selected from donors expressing a homozygous HLA haplotype, in particular homozygous for an HLA type which is expressed widely in the population, thereby providing a means of generating a bank of cells which exhibit broad donor suitability. Still further, it has been determined that the generation of an iPSC from a T cell which exhibits T cell receptor specificity directed to an antigen of interest means that the gene rearrangements for that TCR specific for the cancer antigen will be embedded in the iPSC. All T cells induced from that iPSC will retain the anti-cancer TCR specificity. This can be followed by transfection of such iPSC with a CAR, enabling the subsequent differentiation of said iPSC to a T cell, such as a CD4+ or CD8+ T cell, which stably exhibits dual specificity for the antigen to which the CAR is directed and a TCR directed to the antigen to which the original T cell was directed to. Without limiting the present invention to any one theory or mode of action, it is thought that this is due to the actions of epigenetic memory. Still further, it has also been determined that dual specific NKT cells can be similarly generated. Accordingly, there can be provided an ongoing source of T and NKT cells which are selectively and stably directed to multiple distinct antigenic determinants, such as multiple distinct tumour antigenic determinants, thereby enabling a more therapeutically effective treatment step to be effected.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

The subject specification contains amino acid sequence information prepared using the program PatentIn Version 3.5, presented herein after the bibliography. Each amino acid sequence is identified in the sequence listing by the numeric indicator <210> followed by the sequence identifier (eg. <210>1, <210>2, etc). The length, type of sequence (protein, etc) and source organism for each amino acid sequence are indicated by information provided in the numeric indicator fields <211>, <212> and <213>, respectively. Amino acid sequences referred to in the specification are identified by the indicator SEQ ID NO: followed by the sequence identifier (e.g., SEQ ID NO: 1, SEQ ID NO: 2, etc.). The sequence identifier referred to in the specification correlates to the information provided in numeric indicator field <400> in the sequence listing, which is followed by the sequence identifier (e.g., <400>1, <400>2, etc.). That is SEQ ID NO:

1 as detailed in the specification correlates to the sequence indicated as <400>1 in the sequence listing.

Unless otherwise defined, all technical and scientific terms used herein have the same meaning as commonly understood by one of ordinary skill in the art to which this invention belongs.

One aspect of the present invention is directed to a genetically modified mammalian stem cell, or a T cell differentiated therefrom, which cell is capable of differentiating to a T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified mammalian stem cell expresses at least one homozygous HLA haplotype.

In another aspect there is provided a genetically modified mammalian stem cell, or a T cell differentiated therefrom, which cell is capable of differentiating to a CD4$^+$ T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified mammalian stem cell expresses at least one homozygous HLA haplotype.

In still another aspect there is provided a genetically modified mammalian stem cell, or a T cell differentiated therefrom, which cell is capable of differentiating to a CD8$^+$ T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified mammalian stem cell expresses at least one homozygous HLA haplotype.

In a further aspect there is provided a genetically modified mammalian stem cell, or a T cell differentiated therefrom, which cell is an iPSC (induced pluripotent stem cell) or an HSC (haemopoietic stem cell), is capable of differentiating to a T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified stem cell such as iPSC or HSC expresses at least one homozygous HLA haplotype.

In accordance with this aspect of the invention, in one embodiment, the stem cell (e.g., iPSC) is derived from a cell in which the TCR genes have undergone re-arrangement.

In another embodiment, said stem cell (e.g., iPSC) is derived from a T cell or thymocyte expressing an αβ TCR.

In still another embodiment, said stem cell (e.g., iPSC) is derived from a T cell or thymocyte expressing a γδ TCR.

In yet another embodiment, said stem cell (e.g., iPSC) is derived from a T cell or thymocyte expressing a TCR directed to said first antigenic determinant, i.e., the same antigenic determinant to which the TCR expressed on a T cell derived from said stem cell (e.g., iPSC) is directed.

In still another embodiment, said stem cell (e.g., iPSC) is derived from a T cell or thymocyte that is CD8$^+$.

In yet another embodiment, said stem cell (e.g., iPSC) is derived from a T cell or thymocyte that is CD4$^+$.

In one embodiment, the stem cell (e.g., iPSC or HSC) is capable of differentiating into a CD4$^+$ T cell expressing a TCR directed to a first antigenic determinant. In another embodiment, the stem cell (e.g., iPSC or HSC) is capable of differentiating into a CD8$^+$ T cell expressing a TCR directed to a first antigenic determinant.

In still another further aspect there is provided a genetically modified mammalian stem cell, or a T cell differentiated therefrom, which cell is capable of differentiating to a T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety, and wherein said antigenic determinants are selected from tumour antigens, microorganism antigens or autoreactive immune cell antigens. In some embodiments, the genetically modified mammalian stem cell expresses at least one homozygous HLA haplotype.

In one embodiment, said stem cell is an iPSC. In another embodiment, the stem cell is an HSC.

In another embodiment, said stem cell is capable of differentiating to a CD4$^+$ T cell or a CD8$^+$ T cell.

In still another embodiment, said TCR is an αβ TCR.

In yet still another embodiment, said stem cell (e.g., iPSC) is derived from a T cell or thymocyte, preferably a CD8$^+$ T cell or thymocyte. In some embodiments, said stem cell (e.g., iPSC) is derived from a CD8$^+$ T cell or thymocyte expressing a TCR directed to said first antigenic determinant, i.e., the same antigenic determinant to which the TCR expressed on a T cell derived from said stem cell (e.g., iPSC) is directed.

In yet another aspect there is provided a genetically modified mammalian stem cell, or a T cell differentiated therefrom, which cell is capable of differentiating to a T cell expressing a TCR directed to a first tumour antigenic determinant, and comprises a nucleic acid molecule encoding a chimeric antigen receptor, wherein said receptor comprises an antigen recognition moiety directed to a second tumour antigenic determinant, which antigen recognition moiety is operably linked to a T cell activation moiety, and wherein said first antigenic determinant is selected from TCR recognized peptides such as WT-1 or EbvLMP2, and said second antigenic determinant is selected from, for example, TAG-72, CD19, MAGE, or CD47. In some embodiments, the genetically modified mammalian stem cell expresses at least one homozygous HLA haplotype.

The genetically modified mammalian stem cells (e.g., iPSCs or HSCs) disclosed herein are capable of differentiating to a T cell expressing a TCR directed to a first antigenic determinant (e.g., a first tumour antigenic determinant), and comprises a nucleic acid molecule encoding a chimeric antigen receptor which comprises an antigen recognition moiety directed to a second antigenic determinant (e.g., a second tumour antigenic determinant), operably linked to a T cell activation moiety. That is, the genetically modified stem cells (e.g., iPSCs or HSCs) disclosed herein are capable of differentiating into T cells directed to multiple, i.e., at least two (namely two or more) antigenic determinants. In some embodiments, the genetically modified mammalian stem cell expresses at least one homozygous HLA haplotype.

Accordingly, in a further aspect, there is provided a genetically modified mammalian stem cell capable of differentiating into a T cell directed to more than two antigenic determinants.

In accordance with this aspect of the invention, in some embodiments, the genetically modified mammalian stem cell (e.g., iPSC or HSCs) is capable of differentiating to a T cell expressing a TCR directed to a first antigenic determinant, and comprises multiple (i.e., two or more) nucleic acid molecules encoding multiple chimeric antigen receptors, wherein each chimeric antigen receptor comprises an antigen recognition moiety directed to an antigenic determinant, which antigen recognition moiety is operably linked to a T cell activation moiety. In some embodiments, the genetically modified mammalian stem cell expresses at least one homozygous HLA haplotype.

In one embodiment, the multiple antigenic determinants which the multiple chimeric antigen receptors are directed to are each distinct from said first antigenic determinant to which the TCR expressed on a T cell derived from said stem cell is directed. In another embodiment, the multiple antigenic determinants which the multiple chimeric antigen receptors are directed to are distinct, one from another, and are also distinct said first antigenic determinant to which the TCR expressed on a T cell derived from said stem is directed.

In one embodiment, the multiple CAR-encoding nucleic acids are included in one contiguous nucleic acid fragment. For example, the multiple CAR-encoding nucleic acids are placed in one construct or vector which is transfected into a cell to generate a genetically modified mammalian stem cell comprising the multiple CAR-encoding nucleic acids. In a specific embodiment, the multiple CAR encoding nucleic acids can be linked to each other within one expression unit and reading frame (for example, by utilizing a self-cleaving peptide such as P2A), such that one single polypeptide comprising multiple CAR polypeptide sequences is initially produced and subsequently processed to produce multiple CARs. In another embodiment, the multiple CAR-encoding nucleic acids are placed in separate vectors which are used in transfection to generate a genetically modified mammalian stem cell comprising the multiple CAR-encoding nucleic acids. Examples of CAR-encoding nucleic acid constructs are depicted in FIG. 11, and exemplary sequences for a CAR and various domains suitable for use in a CAR are provided in SEQ ID NOS: 1-2 and 7-20.

Further in accordance with the aspect of the invention providing a genetically modified mammalian stem cell capable of differentiating into a T cell directed to more than two antigenic determinants, in other embodiments, the genetically modified mammalian stem cell (e.g., iPSC or HSC) (which optionally expresses at least one homozygous HLA haplotype), is capable of differentiating to a T cell expressing a TCR directed to a first antigenic determinant, comprises a nucleic acid molecule encoding a chimeric antigen receptor which comprises an antigen recognition moiety directed to a second antigenic determinant, operably linked to a T cell activation moiety, and further comprises a nucleic acid molecule encoding an antigen-binding receptor which comprises an antigen recognition moiety directed to a third antigenic determinant. According to these embodiments, such genetically modified stem cell is capable of differentiating into a T cell directed to multiple antigenic determinants, preferably multiple antigenic determinants that are distinct one from another. Additional antigenic specificity can be provided by employing multiple CAR-encoding nucleic acids as described herein, and/or utilizing multiple nucleic acids encoding antigen binding receptors.

In one embodiment, the antigen-binding receptor is a non-signalling antigen-binding receptor, namely, the receptor is anchored to the cell surface and binds to the third antigenic determinant, but does not transduce signal into the cytoplasmic part of the cell. In one embodiment, the antigen-binding receptor comprises an antigen recognition moiety directed to a third antigenic determinant, operably linked to a transmembrane domain, but lacks a T cell activation moiety.

In a specific embodiment, the antigen-binding receptor is a non-signalling antigen-binding receptor directed to CD47. For example, the antigen-binding receptor is a non-signalling CD47-binding molecule, e.g., a truncated, CD47-binding molecule.

Accordingly, there is provided a genetically modified mammalian stem cell (e.g., iPSC or HSC), or a T cell differentiated therefrom, which cell is capable of differentiating to a T cell expressing a TCR directed to a first antigenic determinant, comprises (i) a nucleic acid molecule encoding a chimeric antigen receptor, wherein said receptor comprises an antigen recognition moiety directed to a second antigenic determinant, which antigen recognition moiety is operably linked to a T cell activation moiety and (ii) a nucleic acid molecule encoding a non-signalling CD47-binding molecule, e.g., a truncated, CD47-binding molecule. In some embodiments, the genetically modified mammalian stem cell (e.g., iPSC or HSC) expresses at least one homozygous HLA haplotype.

In another aspect there is provided a method of making a genetically modified mammalian stem cell (such as an iPSC or HSC) disclosed herein.

In one embodiment, the subject method comprises obtaining a mammalian stem cell (such as an iPSC or HSC) that is capable of differentiating to a T cell expressing a TCR directed to a first antigenic determinant, which stem cell (e.g., iPSC or HSC), in one embodiment, expresses at least one homozygous HLA haplotype; and introducing into the stem cell (e.g., via transfection) one or more nucleic acid molecules encoding one or more chimeric antigen receptors, each chimeric antigen receptor comprising an antigen recognition moiety directed to an antigenic determinant, which antigen recognition moiety is operably linked to a T cell activation moiety. In another embodiment, the method further comprises introducing into the stem cell (e.g., via transfection) one or more nucleic acid molecules encoding one or more antigen-binding receptors (e.g., non-signalling antigen-binding receptors), each antigen-binding receptor comprising an antigen recognition moiety directed to an antigenic determinant. As further disclosed herein, the multiple receptor-encoding nucleic acids can be introduced by way of a single vector or separate vectors.

In another embodiment, the subject method comprises obtaining a T cell or thymocyte (preferably CD8+ T cell or thymocyte) which expresses a TCR directed to a first antigenic determinant, and which, in one embodiment, also expresses at least one homozygous HLA haplotype; introducing into the T cell or thymocyte one or more nucleic acid molecules encoding one or more chimeric antigen receptors, each chimeric antigen receptor comprising an antigen recognition moiety directed to an antigenic determinant, which antigen recognition moiety is operably linked to a T cell activation moiety; and deriving a stem cell (e.g., iPSC) from the T cell or thymocyte. In another embodiment, the method further comprises, before the step of deriving a stem cell from the T cell or thymocyte, introducing into the T cell or thymocyte one or more nucleic acid molecules encoding one or more antigen-binding receptors (e.g., non-signalling antigen-binding receptors), each antigen-binding receptor comprising an antigen recognition moiety directed to an antigenic determinant.

In still another embodiment, the subject method comprises obtaining an HSC (e.g., from the bone marrow or blood) which, in some embodiments, expresses at least one homozygous HLA haplotype; introducing to the HSC (i) one or more nucleic acids encoding a TCR directed to a first antigenic determinant, (ii) one or more nucleic acid molecules encoding one or more chimeric antigen receptors, each chimeric antigen receptor comprising an antigen recognition moiety directed to an antigenic determinant that is different from said first antigenic determinant, which antigen recognition moiety is operably linked to a T cell activation moiety; and optionally (iii) one or more nucleic acid molecules encoding one or more antigen-binding receptors (e.g., non-signalling antigen-binding receptors), each antigen-binding receptor comprising an antigen recognition moiety directed to an antigenic determinant that is different from said first antigenic determinant and different from the antigen determinant(s) to which the chimeric antigen receptor(s) is(are) directed. As disclosed herein, the multiple receptor-encoding nucleic acids can be introduced by way of a single vector or separate vectors. Such genetically modified HSC can be used to generate T cells having specificity to multiple antigenic determinants.

In a further aspect there is provided a T cell that expresses a TCR directed to a first antigenic determinant, and expresses one or more chimeric antigen receptors, wherein each receptor comprises an antigen recognition moiety directed to an antigenic determinant, which antigen recognition moiety is operably linked to a T cell activation moiety. In some embodiments, the T cell further expresses an antigen-binding receptor which comprises an antigen recognition moiety directed an antigenic determinant. In some embodiments, the T cell provided therein expresses at least one homozygous HLA haplotype.

In another aspect there is provide a method for making a T cell that expresses a TCR directed to a first antigenic determinant, and expresses one or more CARs wherein each CAR comprises an antigen recognition moiety directed to an antigenic determinant, which antigen recognition moiety is operably linked to a T cell activation moiety, and optionally also expresses one or more non-signalling antigen-binding receptors each of which comprises an antigen recognition moiety directed to an antigenic determinant. In some embodiments, the method provided herein is directed to making a T cell that expresses at least one homozygous HLA haplotype.

Another aspect of the present invention is directed to a method of treating a condition characterised by the presence of an unwanted population of cells in a mammal, said method comprising administering to said mammal an effective number of stem cells or T cells, as hereinbefore described.

In one embodiment, said condition is a neoplastic condition, a microorganism infection (such as HIV, STD or antibiotic resistant bacteria), or an autoimmune condition.

According to this embodiment, there is provided a method of treating a neoplastic condition, said method comprising administering to said mammal an effective number of stem cells, or T cells, as hereinbefore defined wherein said TCR is directed to a first tumour antigenic determinant and said CAR is directed to a second tumour antigenic determinant.

In still another embodiment, said first tumour antigenic determinant is WT-1.

In another embodiment, said second tumour antigenic determinant is TAG-72, CD19, MAGE, or CD47.

Yet another aspect of the present invention is directed to the use of stem cells or T cells, as hereinbefore defined in the manufacture of a medicament for the treatment of a condition characterised by the presence of an unwanted population of cells in a mammal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1O. Stimulation and expansion of cytotoxic T cells expressing a TCR specific for Wilm's Tumor 1 (WT-1) antigen. Cells were isolated from whole blood peripheral blood mononuclear cells (PBMCs). Cells were gated on single cells (A, F, K) where the scatter plot is also depicted (B, G, L), followed by CD3 positive cells (conjugated to APCCy7; C, H, M), followed by CD8 (conjugated to PECy7) and CD4 (conjugated to PerCp; D, I, N), and finally on CD8 cells alone (E, J, O). WT-1 staining was carried out using HLA-A02 tetramer specific for the WT-$1_{37}$ peptide. Representations are from two separate patients (patient 1 A-E; patient 2 F-J) that are HLA-A02 positive and compared to a fluorescence minus one (FMO; this stain lacks the WT-1 tetramer stain, showing the specificity stain of WT-$1_{37}$, K-O). Proportions shown are a percentage of CD3+ cells. The percentage of WT-1 TCR T cells increased to 1.5% and 4.5% for the two samples; in unstimulated PBMC these cells are very low (below the level of detection using the tetramer technology herein). In other studies (e.g., Schmeid et al (2015)) they are as few 1 per $10^{-6}$ of CD8+ cells (range $3 \times 10^{-7}$ to $3 \times 10^{-6}$ cells).

FIGS. 2A-2G. CD8+ Cytotoxic T cells with TCR specific for Wilm's Tumor 1 (WT-1) antigen are functional. Function is represented by production of interferon gamma (IFN-$\gamma$) (Ghanekar et al 2001). IFN-$\gamma$ expression was found after WT-1 specific stimulation. Activated cells were gated on the CD8+ and HLA-A02 tetramer to the WT-$1_{37}$ peptide-PE conjugated fluorochrome. These cytotoxic T cells with TCR specific for WT-1, when stimulated with WT-1, demonstrated intracellular cytokine stain of IFN-$\gamma$ (conjugated to the pacific blue fluorochrome). Representations are from two separate patients (Wt-1 #1 and WT-1 #2) (patient 1: A-B; patient 2: C-D) that are HLA-A02 positive and compared to a fluorescence minus one (FMO; E-F; this stain lacked the WT-1 tetramer stain, showing the specificity stain of WT-$1_{37}$ (G). Proportions shown are a percentage of WT1+CD8+ cells. Over 80% of the WT-1 TCR T cells produced IFN$\gamma$.

FIG. 6. Flow cytometry for HSC in iPSC-derived cells after 13 days culture on OP9 cells followed by 9 days culture on OP9 DL-L1 cells. Cells were gated on viability, CD45 expressions, single cells then examined for HSC content by staining for CD34 and CD43. Note the reduction in HSC from >90% pre OPDL-L1 culture (FIG. 5), to ~60% after 9 days culture on OP9DL-L1 cells.

FIG. 13. Lentivirus Transformation scheme. Schematic of the processes undertaken for generating CAR containing lentiviral constructs. The CAR construct is cloned into the pWP1 plasmid vector and is linked to the fluorescent reporter EGFP by a P2A self-cleaving polypeptide to separate the CAR and reporter. When transduction of the cell is successful the P2A is expressed and cleaved, and the EGFP identified by flow cytometry and immunofluorescence microscopy.

FIG. 14A. Schematic of normal second generation CAR structure. scFv binding domains to target antigens; hinge region (stalk) allowing integration of the CAR into the plasma membrane (length of hinge can differentially influence scFv binding to target cells); cytoplasmic signalling domains which induce T cell activation upon engagement of the scFv. The CAR structure is shown as a dimer, stabilised by disulphide bonds between adjacent cysteine residues in the hinges region.

FIG. 14B. Schematic of a non-signalling antigen-binding receptor, a truncated CD47 "attachment stalk". Structure shows scFv domains or single V-domains for CD47 antigen binding, attached to a hinge and transmembrane region but no signalling domains are present in the endodomain. This construct would allow increased binding affinity of the CAR-T cell to the cancer cells expressing high levels of CD47. While this receptor could also bind to normal cells which express lower levels of CD47, there would be no signal transduction and hence no damage to the normal cells. The Hinge region may contain cysteine residues to direct dimerization by disulphide bond formation between adjacent hinge domains, or may have the cysteine residues substituted by other residues, such as serine, which do not form disulphide bonds and do not form covalently stabilised dimers.

FIGS. 19A-19B. Flow cytometry analysis of CAR transduction of WT-1 specific TCR CD8+ T cells derived from iPSC produced from WT-1 specific T cells. FIG. 19A. WT-1 specific TCR T cells were successfully transduced with the TAG72 Lentivirus CAR construct (31.3% positive compared to <0.1% in the controls). FIG. 19B. WT-1 specific TCR T cells derived from iPSC formed from WT-1 specific TCR T cells successfully transduced with dual specificity CAR construct for TAG 72 plus non-signalling truncated CD47 (55% transduced); transduced with TAG 72 alone 32%. These transduced T cells contained 3 anti-cancer specificities: WT-1 (TCR); TAG72 (CAR); truncated non-signalling CD47.

FIG. 21B demonstrates the successful transduction of WT-1 T cell derived iPSCs with TAG72 CAR. These iPSCs were therefore successfully imprinted for both WT-1 TCR and TAG 72 specificity.

DETAILED DESCRIPTION OF THE INVENTION

Figure 2H:
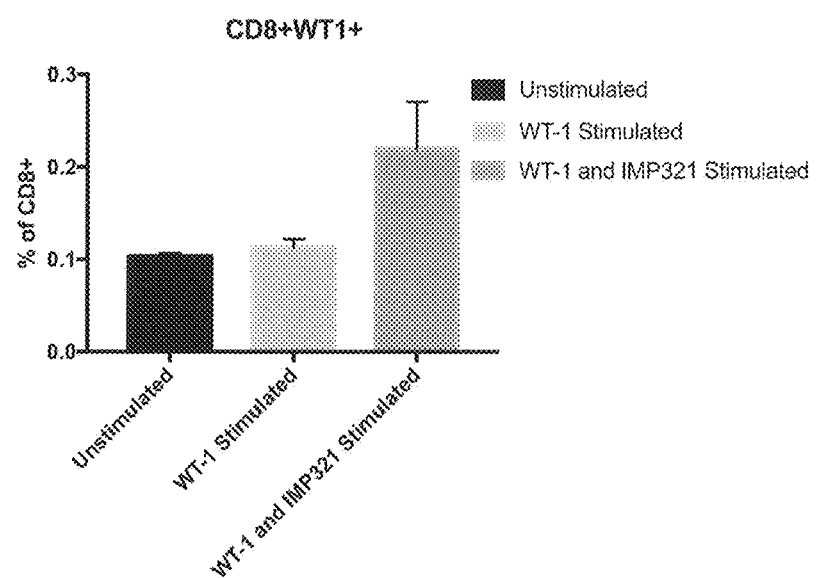
FIG. 2H. Addition of the LAG3 inhibitor (IMP 321) increases the frequency of WT-1 specific T cells after 4 days stimulation. In this experiment, purified but unseparated cord blood mononuclear cells were plated either alone, with either anti CD28 alone, with WT-1 peptide (Miltenyi Biotech) and CD28 (1 µg/ml) or with WT-1 peptide plus IMP321, for 24 hours and 4 days. No effects were observed by 24 hours (data not shown) but, consistent with the kinetics of IMP 321 effect on activation dendritic cells (Brigone et al (2007)), there was a doubling of WT-1 specific CD8+ T cells after 4 days.

The present invention is predicated, in part, on the determination that dual TCR/CAR expressing T cells, directed to two distinct antigenic determinants, can be consistently and stably generated by, for example, transfecting a CAR cassette into an iPSC derived from a T cell exhibiting TCR specificity directed to an antigenic determinant of interest. By virtue of the actions of epigenetic memory, a T cell differentiated from this iPSC has been found to stably express both the TCR specificity of the somatic T cell from which the iPSC was derived, and a CAR directed to a distinct antigenic determinant. Specificity to additional antigenic determinants can be achieved by introducing into cells additional nucleic acid(s) encoding a molecule(s) that bind (s) to such additional antigenic determinant(s). Such multi-specificity cell thereby provides a more effective therapeutic outcome than currently available. These determinations have therefore now enabled the development of an ongoing source of stably transformed dual antigen specific T cells, in particular cytotoxic CD8+αβ TCR T cells, for use in the context of any disease condition which is characterised by an unwanted cellular population, such as a neoplastic condition, a viral infection, bacterial infection or an autoimmune condition. This finding, and the generation of cells based thereon, have now facilitated the improvement of therapeutic treatment regimes directed to treating such conditions, in particular neoplastic conditions such as solid tumours or blood cancers (e.g., leukaemias), including metastatic disease.

Accordingly, one aspect of the present invention is directed to a genetically modified mammalian stem cell, or a T cell differentiated therefrom, which cell is capable of differentiating to a T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified mammalian stem cell expresses at least one homozygous HLA haplotype.

Reference to a "T cell" should be understood as a reference to any cell comprising a T cell receptor. In this regard, the T cell receptor may comprise any one or more of the α, β, γ or δ chains. As would be understood by the person of skill in the art, NKT cells also express a T cell receptor and therefore dual specific NKT cells can also be generated according to the present invention. The present invention is not intended to be limited to any particular sub-class of T cell, although in a preferred embodiment the subject T cell expresses an α/β TCR dimer. Still more preferably, said T cell is a $CD4^+$ helper T cell, a $CD8^+$ killer T cell, or an NKT cell. Without limiting the present invention to any one theory or mode of action, $CD8^+$ T cells are also known as cytotoxic cells. As a major part of the adaptive immune system, $CD8^+$ T cells scan the intracellular environment in order to target and destroy, primarily, infected cells. Small peptide fragments, derived from intracellular content, are processed and transported to the cell surface where they are presented in the context of MHC class I molecules. However, beyond just responding to viral infections, CD8+ T cells also provide an additional level of immune surveillance by monitoring for and removing damaged or abnormal cells, including cancers. $CD8^+$ T cell recognition of an MHC I presented peptide usually leads to either the release of cytotoxic granules or lymphokines or the activation of apoptotic pathways via the FAS/FASL interaction to destroy the subject cell. $CD4^+$ T cell, on the other hand, generally recognise peptide presented by antigen presenting cells in the context of MHC class II, leading to the release of cytokines designed to regulate the B cell and/or CD8+ T cell immune responses. Accordingly, unlike cytotoxic T cells, T helper cells do not directly kill unwanted cells, such as cancer cells, although they can augment such a response, to the extent that it is effected by cytotoxic T cells and/or antibody based clearance mechanisms.

Natural killer T (NKT) cells are a specialised population of T cells that express a semi-invariant T cell receptor (TCR α β) and surface antigens typically associated with natural killer cells. The TCR on NKT cells is unique in that it recognizes glycolipid antigens presented by the MHC I-like molecule CD1d. Most NKT cells express an invariant TCR alpha chain and one of a small number of TCR beta chains. The TCRs present on type I NKT cells recognise the antigen alpha-galactosylceramide (alpha-GalCer). Within this group, distinguishable subpopulations have been identified, including $CD4^+CD8^-$ cells, $CD4^-CD^+$ cells and $CD4^-/CD8^-$ cells. Type II NKT cells (or noninvariant NKT cells) express a wider range of TCR α chains and do not recognise the alpha-GalCer antigen. NKT cells produce cytokines with multiple, often opposing, effects, for example either promoting inflammation or inducing immune suppression including tolerance. As a result, they can contribute to antibacterial and antiviral immune responses, promote tumour-related immunosurveillance, and inhibit or promote the development of autoimmune diseases. Like natural killer cells, NKT cells can also induce perforin-, Fas-, and TNF-related cytoxicity. Accordingly, reference to the genetically modified T cells of the present invention should be understood to include reference to NKT cells.

Since thymus-based T cell production is characterised by random generation of the T cell receptor (TCR) repertoire, thymopoiesis must also include very strict selection processes that eliminate or functionally silence those developing thymus T cells with the potential to attack self. This "self tolerance" therefore reduces the potential for autoimmune disease. However, by necessity, this very process compromises the immune surveillance against cancers—given that non-viral induced cancers are by definition diseases of "self". This means that many T cells arising in the thymus, which could potentially have been reactive with tumour-associated antigens, may be eliminated before entry into the blood. At the very least they will be numerically deficient and perhaps express a low affinity TCR.

In one embodiment there is provided a genetically modified mammalian stem cell, or a T cell differentiated therefrom, which cell is capable of differentiating to a $CD4^+$ T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In one embodiment, the genetically modified mammalian stem cell expresses at least one homozygous HLA haplotype.

In another embodiment there is provided a genetically modified mammalian stem cell, or a T cell differentiated therefrom, which cell is capable of differentiating to a $CD8^+$ T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In one embodiment, the genetically modified mammalian stem cell expresses at least one homozygous HLA haplotype.

In some embodiments, the genetically modified cell of the present invention, e.g., the genetically modified stem cell (such as an iPSC or an HSC) or T cell, is homozygous for at least one HLA haplotype. Without limiting the present invention to any one theory or mode of action, the major histocompatibility complex (MHC) represents a set of cell surface molecules, the major function of which is to bind peptide fragments derived from antigens and to present them to T cells. The MHC gene family is divided into three subgroups: class I, class II and class 111. Class 1 MHC molecules express β2 subunits and therefore can only be recognised by CD8 co-receptors. Class II MHC molecules express no β2 subunits and can therefore be recognised by CD4 co-receptors. In this way, MHC molecules regulate which type of lymphocytes may bind to a given antigen with high affinity, since different lymphocytes express different TCR co-receptors. Diversity of antigen presentation, mediated by MHC classes I and II, is attained in at least three ways:

(1) an organism's MHC repertoire is usually polygenic (via multiple, interacting genes);

(2) MHC expression is codominant (from both sets of inherited alleles); and (3) MHC gene variants are highly polymorphic (diversely varying from organism to organism within a species).

MHC molecules bind to both the T cell receptor and a CD4/CD8 co-receptor on T lymphocytes. The antigen epitope held in the peptide-binding groove of the MHC molecule interacts with the variable Ig-Like domain of the TCR to trigger T-cell activation. However, the MHC molecules can also themselves act as antigens and can provoke an immune response in the recipient of a tissue or cells which express a foreign MHC, thus causing transplant rejection. Still further, the transplantation of immunocompetent cells can actually result in rejection of host tissue, also known as graft vs host disease. In this regard, each human cell expresses six MHC class I alleles (one HLA-A, -B, and -C allele from each parent) and six to eight MHC class II alleles (one HLA-DP and -DQ, and one or two HLA-DR from each parent, and combinations of these). The MHC variation in the human population is high, with at least 350 alleles for HLA-A genes, 620 alleles for HLA-B, 400 alleles for DR, and 90 alleles for DQ. Any two individuals who are not identical twins will express differing MHC molecules.

All MHC molecules can mediate transplant rejection, but HLA-C and HLA-DP, which show low polymorphism, are less important. Transplant rejection can be minimised by attempting to match as much of the cell surface HLA repertoire as possible between a donor and a recipient. A complete match is only possible as between identical twins. However, selecting donors based on minimising incompatibility at one or more of the range of HLA antigens expressed on a cell is highly desirable and can significantly minimise rejection problems. This is a particular issue addressed by the present invention since the usual method of managing tissue/cell rejection is the administration of immunosuppressive treatment regimes, this not being desirable in the context of a treatment regime based on the administration of genetically modified immune cells which are required to function at an optimum level of functionality. In accordance with the present invention, this can be achieved by utilizing cells, such as iPSCs, or cells such as T cells from which iPSCs are derived, which are homozygous for one or more MHC haplotypes, the HLA allele of interest being one which is a major transplantation antigen and which is preferably expressed by a significant proportion of the population, such as at least 5%, at least 10/o, at least 15%, at least 17%, at least 20%, or more of the population. Where the homozygous HLA haplotype corresponds to a dominant MHC I or MHC II HLA type (in terms of tissue rejection), the use of such a cell will result in significantly reduced problems with tissue rejection in the wider population who receive the cells of the present invention in the context of a treatment regime. In terms of the present invention, the genetically modified cells may be homozygous in relation to one cellular HLA antigen or they may be homozygous in relation to more than one HLA antigen, e.g., 2, 3, or more HLA antigens. In some embodiments, the genetically modified cells are homozygous in relation to one HLA antigen selected from those listed in Table 1, including e.g., HLA A1, B8, C7, DR17, DQ2, or HLA A2, B44, C5, DR4, DQ8, or HLA A3, B7, C7, DR15, DQ6. In some embodiments, the genetically modified cells are homozygous in relation to two or more HLA antigens selected from those listed in Table 1, including e.g., HLA A1, B8, C7, DR17, DQ2, or HLA A2, B44, C5, DR4, DQ8, or HLA A3, B7, C7, DR15, DQ6.

The term "HLA-type" should therefore be understood to refer to the complement of HLA antigens present on the cells of an individual.

Obtaining a suitable homozygous HLA T cell for use in generating an iPSC can be achieved by any suitable method including, for example, screening a population (such as via a blood bank) to identify individuals expressing HLA homozygocity and then screening for T cells from that individual which exhibit the TCR specificity of interest. These normally very rare T cells can be selectively stimulated by the specific antigenic peptide that their TCR recognises and vastly increased in frequency (e.g., from <0.0001 to 0.2).

It would be appreciated by the person skilled in the art that significant information is widely available in the public literature which describes the identification and utility of homozygous haplotypes in terms of minimizing donor-recipient HLA mismatch across a given population of interest, thereby enabling the generation of donor banks. See for example Pappas et al (2015). In one example, Table 1 identifies the 15 highest ranked homozygous HLA haplotypes relative to the proportion of the UK population to which this provides minimal mismatch. The first 8 listed homozygous HLA haplotypes are compatible with 49% of the population. A further example is outlined in Table 2 which details the first 10 ranked haplotypes compatible with the ethnically diverse Californian population. Table 2 includes match frequencies for subpopulations, including, black or African American, Asian and Pacific Islander, white, Hispanic and American Indian and Alaska natives. Further still, Table 3 outlines the 50 most frequent haplotypes for HLA-A-B-DR, A-B, A-DR and B-DR in the North China population. It would be appreciated that a person skilled in the art would understand that the data depicted in Table 3 can be used to define a set of homozygous haplotypes which would provide minimal mismatch for the North Chinese population.

TABLE 1

Utility of 15 highest ranked homozygous HLA-A, -B, -DR types identified to provide a zero HLA mismatch for the UK population.

| Rank | HLA-A | HLA-B | HLA-DR | Recipients matched (%) | Recipients matched (cumulative %) |
|---|---|---|---|---|---|
| 1 | A1 | B8 | DR17(3) | 16.87 | 16.87 |
| 2 | A2 | B44(12) | DR4 | 9.51 | 26.38 |
| 3 | A3 | B7 | DR15(2) | 7.45 | 33.83 |
| 4 | A2 | B7 | DR15(2) | 4.28 | 38.11 |
| 5 | A2 | B44(12) | DR7 | 3.41 | 41.52 |
| 6 | A2 | B62(15) | DR4 | 2.85 | 44.37 |
| 7 | A1 | B57(17) | DR7 | 2.54 | 46.91 |
| 8 | A3 | B35 | DR1 | 2.10 | 49.01 |
| 9 | A29(19) | B44(12) | DR7 | 2.04 | 51.05 |
| 10 | A2 | B60(40) | DR4 | 1.75 | 52.80 |
| 11 | A2 | B8 | DR17(3) | 1.60 | 54.40 |
| 12 | A2 | B27 | DR1 | 1.28 | 55.68 |
| 13 | A2 | B44(12) | DR13(6) | 1.23 | 56.91 |
| 14 | A3 | B7 | DR4 | 1.20 | 58.11 |
| 15 | A1 | B8 | DR4 | 0.94 | 59.05 |

TABLE 2

Top cis and trans matched haplolines of the California population.

| Haplotype HLA-A~B~DRB1 | CIS | | TRANS | | Expected CIS match frequency | | | | | |
|---|---|---|---|---|---|---|---|---|---|---|
| | Match % ($K_i$) | SD | Match % ($K_i$) | SD | $f_{CAU}$ | $f_{HIS}$ | $f_{API}$ | $f_{AFA}$ | $f_{NAM}$ | $f_{exp}$ |
| 01:01 g~08:01 g~03:01 | 6.32 | 0.24 | 6.64 | 0.26 | 11.63 | 3.57 | 0.47 | 2.181 | 8.484 | 5.59 |
| 03:01 g~07:02 g~15:01 | 3.47 | 0.18 | 1.06 | 0.19 | 5.967 | 2.37 | 0.4 | 1.198 | 4.618 | 3.06 |
| 29:02 g~44:03~07:01 | 2.57 | 0.15 | 2.71 | 0.15 | 3.731 | 1.17 | 0.11 | 0.68 | 2.88 | 1.8 |

TABLE 2-continued

Top cis and trans matched haplolines of the California population.

| Haplotype HLA- A~B~DRB1 | CIS Match % ($K_i$) | SD | TRANS Match % ($K_i$) | SD | Expected CIS match frequency | | | | | |
|---|---|---|---|---|---|---|---|---|---|---|
| | | | | | $f_{CAU}$ | $f_{HIS}$ | $f_{API}$ | $f_{AFA}$ | $f_{NAM}$ | $f_{exp}$ |
| 02:01 g~07:02 g~15:01 | 2.03 | 0.15 | 3.6 | 0.2 | 3.565 | 0.76 | 0.06 | 0.927 | 3.206 | 1.64 |
| 02:01 g~44:02 g~04:01 | 1.85 | 0.13 | 2.22 | 0.15 | 2.851 | 3.63 | 0.07 | 0.779 | 2.55 | 2.23 |
| 01:01 g~57:01 g~07:01 | 1.68 | 0.13 | 1.95 | 0.14 | 2.356 | 0.84 | 0.35 | 0.465 | 1.617 | 1.2 |
| 03:01 g~35:01 g~01:01 | 1.35 | 0.11 | 1.61 | 0.11 | 2.521 | 0.47 | 0.05 | 0.435 | 1.877 | 1.11 |
| 02:01 g~15:01 g~04:01 | 1.24 | 0.12 | 1.57 | 0.14 | 2.124 | 0.89 | 2.89 | 0.43 | 1.973 | 1.47 |
| 30:01 g~13:02 g~07:01 | 1.24 | 0.12 | 1.3 | 0.12 | 1.663 | 0.3 | 0.04 | 0.282 | 1.203 | 0.73 |
| 33:01 g~14:02~01:02 | 0.99 | 0.1 | 1.02 | 0.1 | 1.532 | 0.62 | 0.08 | 0.304 | 1.21 | 0.79 |

Abbreviations
AFA, black or African American;
API, Asian and Pacific Islander;
CAU, white (non-Hispanic);
CIS, cis match benefit;
$f_{exp}$, expected cis match frequency;
HIS, Hispanic;
$K_i$, number of matches as a count or percentages of the total number of subjects;
NAM, American Indian and Alaska native;
TRANS, trans match benefit.

TABLE 3

50 most frequent haplotypes for HLA-A-B-DR, A-B, A-DR and B-DR
(at $10^{-5}$) HF = haplotype frequency per 100,000

| HLA-A-B-DR | | | HLA-A-A-B | | | HLA-A-DR | | | HLA-A-B-DR | | |
|---|---|---|---|---|---|---|---|---|---|---|---|
| Haplotype | HF | R.L.D | Haplotype | HF | R.L.D | Haplotype | HF | R.L.D | Haplotype | HF | R.L.D |
| A30-B13-DR7 | 4446 | 0.58 | A30-B13 | 5538 | 0.81 | A2-DR9 | 5882 | 0.23 | B13-DR7 | 5617 | 0.44 |
| A2-B46-DR9 | 2388 | 0.16 | A2-B46 | 5090 | 0.60 | A2-DR15 | 4703 | −0.04 | B46-DR9 | 3225 | 0.37 |
| A33-B58-DR17 | 1436 | 0.29 | A33-B58 | 3201 | 0.74 | A30-DR7 | 4532 | 0.64 | B13-DR12 | 2303 | 0.12 |
| A2-B13-DR12 | 1088 | 0.04 | A2-B61 | 2592 | 0.17 | A2-DR12 | 4118 | 0.13 | B52-DR15 | 2285 | 0.55 |
| A2-B46-DR8 | 1046 | 0.07 | A2-B51 | 2411 | 0.6 | A11-DR15 | 3426 | 0.03 | B62-DR4 | 2070 | 0.18 |
| A33-B58-DR13 | 1010 | 0.18 | A2-B62 | 2198 | 0.00 | A24-DR15 | 3143 | 0.03 | B61-DR9 | 2045 | 0.22 |
| A33-B44-DR13 | 936 | 0.14 | A11-B60 | 2197 | 0.18 | A2-DR4 | 2987 | −0.11 | B62-DR15 | 1921 | 0.11 |
| A2-B61-DR9 | 904 | 0.01 | A2-B13 | 2136 | −0.35 | A11-DR12 | 2979 | 0.12 | B44-DR7 | 1869 | 0.28 |
| A1-B37-DR10 | 860 | 0.46 | A11-B62 | 2106 | 0.13 | A11-DR4 | 2704 | 0.07 | B7-DR15 | 1867 | 0.29 |
| A11-B75-DR12 | 848 | 0.12 | A2-B60 | 1879 | −0.3 | A2-DR8 | 2660 | 0.20 | B58-DR17 | 1858 | 0.42 |
| A11-B62-DR4 | 814 | 0.04 | A24-B61 | 1802 | 0.15 | A24-DR4 | 2584 | 0.08 | B51-DR9 | 1727 | 0.12 |
| A24-B54-DR4 | 697 | 0.11 | A24-B62 | 1798 | 0.10 | A11-DR9 | 2378 | 0.01 | B54-DR4 | 1497 | 0.38 |
| A2-B62-DR15 | 676 | 0.02 | A24-B60 | 1765 | 0.13 | A24-DR9 | 2375 | 0.03 | B44-DR13 | 1480 | 0.25 |
| A3-B7-DR15 | 658 | 0.10 | A33-B44 | 1752 | 0.29 | A2-DR14 | 2169 | 0.08 | B46-DR8 | 1453 | 0.18 |
| A1-B57-DR7 | 647 | 0.38 | A11-B13 | 1689 | −0.16 | A33-DR13 | 2057 | 0.34 | B75-DR12 | 1405 | 0.26 |
| A11-B7-DR1 | 647 | 0.11 | A2-B75 | 1679 | 0.18 | A2-DR11 | 2012 | −0.01 | B60-DR15 | 1325 | 0.04 |
| A24-B61-DR9 | 607 | 0.03 | A11-B75 | 1632 | 0.28 | A24-DR12 | 1860 | 0.02 | B58-DR13 | 1269 | 0.26 |
| A2-B51-DR9 | 597 | 0.15 | A24-B54 | 1468 | 0.33 | A2-DR7 | 1553 | −0.53 | B13-DR15 | 1204 | −0.35 |
| A2-B61-DR12 | 586 | 0.02 | A2-B35 | 1446 | −0.19 | A24-DR11 | 1524 | 0.07 | B37-DR10 | 1188 | 0.67 |
| A24-B62-DR4 | 579 | 0.02 | A24-B51 | 1445 | 0.4 | A33-DR17 | 1502 | 0.31 | B35-DR15 | 1122 | 0.02 |
| A32-B52-DR15 | 575 | 0.23 | A11-B51 | 1399 | 0.1 | A24-DR14 | 1410 | 0.08 | B7-DR1 | 1102 | 0.24 |

TABLE 3-continued 50 most frequent haplotypes for HLA-A-B-DR, A-B, A-DR and B-DR
(at $10^{-5}$) HF = haplotype frequency per 100,000

| HLA-A-B-DR | | | HLA-A-B | | | HLA-A-DR | | | HLA-B-DR | | |
|---|---|---|---|---|---|---|---|---|---|---|---|
| Haplotype | HF | R.L.D | Haplotype | HF | R.L.D | Haplotype | HF | R.L.D | Haplotype | HF | R.L.D |
| A11-B13-DR15 | 572 | 0.03 | A2-B48 | 1365 | 0.18 | A11-DR14 | 1348 | 0.04 | B61-DR12 | 1094 | 0.07 |
| A11-B62-DR15 | 556 | 0.01 | A1-B37 | 1325 | 0.69 | A11-DR8 | 1211 | 0.02 | B8-DR17 | 1058 | 0.82 |
| A33-B44-DR7 | 532 | 0.05 | A2-B38 | 1264 | 0.19 | A3-DR15 | 1173 | 0.07 | B61-DR15 | 1001 | −0.07 |
| A11-B13-DR12 | 532 | 0.00 | A24-B35 | 1079 | 0.3 | A11-DR11 | 1070 | −0.15 | B57-DR7 | 986 | 0.65 |
| A11-B52-DR15 | 512 | 0.01 | A11-B52 | 1060 | 0.13 | A1-DR7 | 1011 | 0.08 | B75-DR15 | 986 | 0.09 |
| A32-B44-DR7 | 493 | 0.19 | A24-B48 | 1003 | 0.17 | A2-DR16 | 958 | 0.19 | B51-DR15 | 982 | −0.21 |
| A2-B75-DR9 | 484 | 0.03 | A3-B7 | 1001 | 0.18 | A24-DR8 | 954 | −0.03 | B60-DR9 | 967 | 0.02 |
| A11-B51-DR9 | 452 | 0.02 | A1-B57 | 984 | 0.67 | A11-DR1 | 921 | 0.06 | B35-DR11 | 949 | 0.10 |
| A2-B13-DR7 | 431 | 0.67 | A3-B35 | 960 | 0.13 | A1-DR10 | 887 | 0.48 | B60-DR4 | 943 | 0.03 |
| A2-B46-DR14 | 427 | 0.01 | A11-B46 | 906 | −0.30 | A31-DR15 | 879 | 0.08 | B60-DR11 | 929 | 0.08 |
| A11-B75-DR15 | 425 | 0.02 | A24-B13 | 885 | −0.50 | A33-DR7 | 863 | 0.01 | B62-DR12 | 850 | 0.01 |
| A24-B60-DR15 | 420 | 0.01 | A2-B54 | 874 | −0.08 | A3-DR1 | 785 | 0.15 | B51-DR4 | 837 | −0.01 |
| A2-B60-DR15 | 417 | 0.01 | A11-B7 | 848 | 0.1 | A1-DR15 | 781 | −0.13 | B62-DR9 | 821 | −0.15 |
| A24-B51-DR9 | 414 | 0.01 | A11-B35 | 787 | −0.27 | A2-DR17 | 691 | −0.43 | B51-DR11 | 794 | 0.04 |
| A2-B62-DR4 | 408 | 0.30 | A11-B61 | 776 | −0.32 | A3-DR7 | 691 | 0.02 | B60-DR12 | 786 | 0.01 |
| A2-B75-DR12 | 397 | 0.21 | A32-B44 | 763 | 0.34 | A32-DR15 | 683 | 0.20 | B60-DR8 | 771 | 0.06 |
| A2-B46-DR12 | 389 | 0.28 | A31-B51 | 757 | 0.14 | A3-DR4 | 678 | 0.02 | B75-DR9 | 750 | 0.06 |
| A11-B46-DR9 | 387 | 0.28 | A29-B7 | 726 | 0.62 | A11-DR7 | 652 | −0.68 | B51-DR12 | 701 | −0.11 |
| A11-B60-DR9 | 379 | 0.01 | A3-B44 | 705 | 0.9 | A2-DR13 | 624 | −0.59 | B27-DR4 | 693 | 0.25 |
| A11-B60-DR8 | 378 | 0.03 | A2-B71 | 697 | 0.23 | A26-DR15 | 616 | 0.02 | B48-DR15 | 665 | 0.05 |
| A24-B13-DR12 | 377 | 0.01 | A24-B7 | 679 | −0.5 | A2-DR1 | 609 | −0.49 | B71-DR4 | 663 | 0.35 |
| A2-B54-DR4 | 377 | 0.09 | A32-B52 | 677 | 0.31 | A24-DR7 | 596 | −0.67 | B51-DR14 | 644 | 0.03 |
| A2-B75-DR15 | 362 | 0.00 | A11-B55 | 674 | 0.19 | A32-DR7 | 579 | 0.19 | B50-DR7 | 640 | 0.68 |
| A24-B7-DR15 | 362 | 0.01 | A2-B55 | 670 | 0.7 | A1-DR13 | 572 | 0.06 | B35-DR9 | 632 | −0.18 |
| A2-B71-DR4 | 350 | 0.10 | A2-B39 | 654 | 0.7 | A33-DR15 | 550 | −0.54 | B35-DR4 | 625 | −0.09 |
| A11-B60-DR15 | 350 | 0.19 | A11-B54 | 649 | 0.2 | A3-DR13 | 484 | 0.04 | B46-DR14 | 612 | 0.03 |
| A2-B61-DR15 | 345 | 0.15 | A2-B67 | 620 | 0.56 | A31-DR9 | 480 | −0.01 | B62-DR14 | 599 | 0.02 |
| A2-B50-DR7 | 332 | 0.21 | A24-B46 | 604 | −0.46 | A33-DR4 | 476 | −0.42 | B48-DR9 | 556 | 0.05 |
| A2-B48-DR9 | 332 | 0.02 | A31-B62 | 570 | 0.8 | A26-DR4 | 468 | 0.02 | B35-DR1 | 542 | 0.08 |

As detailed hereinbefore, the present invention is predicated on the determination that a stem cell can be consistently and stably engineered to express dual T cell and chimeric antigen receptors directed to multiple distinct antigens, thereby providing an ongoing source of T cells which are more therapeutically effective than the cells used in currently available therapeutic cellular treatment regimes. In this regard, reference to a "stem cell" should be understood as a reference to any cell which exhibits the potentiality to develop in the direction of multiple lineages, given its particular genetic constitution, and thus to form a new organism or to regenerate a tissue or cellular population of an organism. The stem cells which are utilised in accordance with the present invention may be of any suitable type capable of differentiating along two or more lineages and include, but are not limited to, embryonic stem cells, adult stem cells, umbilical cord stem cells, haemopoietic stem cells (HSCs), totipotent cells, progenitor cells, precursor cells, pluripotent cells, multipotent cells or de-differentiated somatic cells (such as an induced pluripotent stem cell). By "totipotent" is meant that the subject stem cell can self renew. By "pluripotent" is meant that the subject stem cell can differentiate to form, inter alia, cells of any one of the three germ layers, these being the ectoderm, endoderm and mesoderm.

In one particular embodiment, the subject stem cell is an induced pluripotent stem cell (iPSC). Without limiting the present invention to any one theory or mode of action, adult stem cell expansion is not necessarily based on the occurrence of asymmetrical stem cell division in order to effect both stem cell renewal and differentiation along a specific somatic cell lineage. In particular, pluripotent stem cells can be sourced from T cells which are induced to transition to a state of multilineage potential. The development of technology to enable the de-differentiation of adult cells is of significant importance due to the difficulty of otherwise inducing stem cell renewal and expansion in vitro.

According to this embodiment there is therefore provided a genetically modified mammalian stem cell, or a T cell differentiated therefrom, which stem cell is an iPSC, is capable of differentiating to a T cell expressing a TCR directed to a first antigenic determinant, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In one embodiment, the genetically modified mammalian iPSC expresses at least one homozygous HLA haplotype.

iPSCs are usually generated directly from somatic cells, although it should be understood that the present invention is not limited in this regard. That is, the subject iPSC may be generated from a cell which is not terminally differentiated; indeed iPSC can be induced in principle from any nucleated cell including, for example, mononucleocytes from blood and skin cells. For example, in the context of one embodiment of the present invention, the subject iPSCs may be generated from fully differentiated T cells or they may be generated from precursor T cells, such as thymocytes. To the extent that the subject thymocyte has re-arranged its TCR and exhibits an antigen specificity of interest in the context of the present invention, one may seek to generate the iPSC from this cell. This may be relevant, for example, where the particular TCR rearrangement in issue is one which might be expected to be selected against during thymopoiesis. It would be appreciated by the skilled person that one of the complicating factors with respect to immunoresponsiveness to tumour cells or autoreactive cells is that in this situation the immune system is required to direct an immune response to a self cell and, therefore, a self-antigen. Such immune cells are usually selected against during T lymphocyte differentiation in the thymus in order to minimize the prospect of the onset of an autoimmune disease. In the context of neoplastic and autoimmune conditions, however, the unwanted cell is a self cell and, accordingly, the cell surface antigens which one may seek to target will be self antigens. Without limiting the present invention in any way, and as discussed in more detail hereafter, one of the advantages of using an iPSC from which to generate a TCR/CAR expressing T cell directed to multiple distinct antigenic determinants is that it has been determined that the actions of epigenetic memory may potentiate the differentiation of an iPSC to a functional T cell which expresses a TCR directed to the same antigen as the T cell from which the iPSC has been derived. However, in terms of selecting a specific TCR expressing cell from which to derive an iPSC, it may be difficult to identify a suitable fully differentiated T cell since a T cell expressing a functional TCR directed to a self antigen may have been selected against during thymopoiesis. It may therefore be more feasible to screen for a thymocyte which expresses the TCR re-arrangement of interest, which thymocyte has not yet undergone negative selection to remove potentially self reactive cells.

In another embodiment, an iPSC is transfected with one or more nucleic acid molecules coding for a TCR (such as rearranged TCR genes) directed to a first antigenic determinant (e.g., a tumour antigenic determinant).

In still another embodiment, the subject stem cell is a haemopoietic stem cell (HSC). Haemopoietic stem cells (HSCs) refer to stem cells that give rise to all the blood cells of the lymphoid and myeloid lineages through the process of haematopoiesis. HSCs are derived from mesoderm, and can be found in adult bone marrow, peripheral blood, and umbilical cord blood. HSCs can be collected from bone marrow, peripheral blood, and umbilical cord blood by established techniques, and are commonly associated with CD34+ expression. In some embodiments, human HSCs can be defined as being CD34+CD38−CD90+CD45RA−(see Reinisch et al (2015)). An HSC can be genetically modified, e.g., transfected, with one or more nucleic acids encoding a TCR directed to a first antigenic determinant, then subsequently directed to differentiate into a T cell. Nucleic acids encoding one or more CARs, and optionally nucleic acids encoding one or more docking antigen-binding receptors, can also be introduced into an HSC, before or after differentiation of the HSC into a T cell.

Reference to a "T cell receptor" (TCR) should therefore be understood as a reference to the heterodimer found on the surface of T cells or NKT cells which recognise peptides presented by MHC. Specifically, CD8+ T cells recognise peptide presented in the context of MHC class I while CD4+ T cells recognise peptide presented in the context of MHC class II. Without limiting the present invention to any one theory or mode of action, in the majority of human T cells, the TCR comprises an $\alpha$ and $\beta$ chain, while a minor population of cells express a TCR comprising a $\gamma\delta$ heterodimer. The TCR is a disulfide-linked membrane-anchored heterodimeric protein. The $\gamma$, $\delta$, $\alpha$ and $\beta$ chains are composed of two extracellular domains: a variable (V) region and a constant (C) region, which both form part of the immunoglobulin superfamily and which fold to form antiparallel $\beta$-sheets. The constant region is proximal to the cell membrane, followed by a transmembrane region and a short cytoplasmic tail, while the variable region binds to the peptide/MHC complex.

The variable domains of both the TCR $\alpha$-chain and $\beta$-chain each express three hypervariable or complementarity determining regions (CDRs), whereas the variable region of the $\beta$-chain has an additional area of hypervariability (HV4) that does not normally contact antigen and, therefore, is not considered a CDR. The processes for the generation of TCR diversity are based mainly on genetic recombination of the DNA encoded segments in precursor T cells—either somatic V(D)J recombination using RAG1 and RAG2 recombinases or gene conversion using cytidine deaminases. Each recombined TCR possesses unique antigen specificity, determined by the structure of the antigen-binding site formed by the $\alpha$ and $\beta$ chains, in the case of $\alpha\beta$ T cells, or $\gamma$ and $\delta$ chains in the case of $\gamma\delta$ T cells. The TCR $\alpha$ chain is generated by VJ recombination, whereas the $\beta$ chain is generated by VDJ recombination. Likewise, generation of the TCR $\gamma$ chain involves VJ recombination, whereas generation of the TCR $\delta$ chain occurs by VDJ recombination. The intersection of these specific regions (V and J for the $\alpha$ or $\gamma$ chain; V, D, and J for the $\beta$ and $\delta$ chain) corresponds to the CDR3 region that is important for peptide/MHC recognition. It is the unique combination of the segments at this region, along with palindromic and random nucleotide additions, which account for the even greater diversity of T cell receptor specificity for processed antigenic peptides.

Accordingly, reference to a TCR "directed" to an antigenic determinant should be understood as a reference to a TCR which has undergone rearrangement and which exhibits specificity for an antigenic determinant, preferably a self (particularly a self cancer) antigenic determinant.

In one embodiment, an iPSC is derived from a cell which expresses a rearranged TCR, preferably a rearranged αβ TCR. Examples of cells suitable for use in generating the iPSCs of the present invention include, but are not limited to CD4$^+$ T cells, CD8$^+$ T cells, NKT cells, thymocytes or other form of precursor T cells. In another embodiment, said cell expresses a rearranged γδ TCR.

There is therefore provided a genetically modified mammalian iPSC or HSC, or a T cell differentiated therefrom, which iPSC or HSC is capable of differentiating to a T cell expressing a TCR directed to a first antigenic determinant, is derived from a cell in which the TCR genes have undergone re-arrangement, or has been transduced with said rearranged genes, and comprises a nucleic acid molecule encoding a chimeric antigen receptor, wherein said receptor comprises an antigen recognition moiety directed to a second antigenic determinant, which antigen recognition moiety is operably linked to a T cell activation moiety. In some embodiments, the genetically modified mammalian iPSC or HSC expresses at least one homozygous HLA haplotype.

In one embodiment, said iPSC is derived from a T cell or a thymocyte.

In another embodiment, said iPSC is derived from a T cell or thymocyte expressing an αβ TCR.

In still another embodiment, said iPSC is derived from a T cell or thymocyte expressing a γδ TCR.

The subject stem cells may have been freshly isolated from an individual who is the subject of treatment or they may have been sourced from a non-fresh source, such as from a culture (for example, where cell numbers were expanded and/or the cells were cultured so as to render them receptive to differentiation signals) or a frozen stock of cells, which had been isolated at some earlier time point either from an individual or from another source. It should also be understood that the subject cells, prior to undergoing differentiation, may have undergone some other form of treatment or manipulation, such as but not limited to purification, modification of cell cycle status or the formation of a cell line such as an embryonic stem cell line. Accordingly, the subject cell may be a primary cell or a secondary cell. A primary cell is one which has been isolated from an individual. A secondary cell is one which, following its isolation, has undergone some form of in vitro manipulation such as the preparation of an embryonic stem cell line, prior to the application of the method of the invention.

To the extent that the stem cells of the present invention are iPSCs, methods for generating iPSCs are well known to the person of skill in the art. In this regard, and as detailed hereinbefore, iPSCs are cells which are derived from a more mature cell type, such as a somatic cell, which has been transitioned/de-differentiated back to a pluripotent state.

Without limiting the present invention to any one theory or mode of action, iPSCs can be derived by introducing a specific set of pluripotency-associated genes, or "reprogramming factors", into a somatic cell type. The most commonly used set of reprogramming factors (also know as the Yamanaka factors) are the genes Oct4 (Pou5f1), Sox2, cMyc, and Klf4. The transfection of these four specific genes encoding transcription factors were shown by Yamanaka in 2006 to convert adult human cells into pluripotent cells. While this combination is the most conventional combination used for producing iPSCs, each of the factors can be functionally replaced by related transcription factors, miRNAs, small molecules, or even non-related genes such as lineage specifiers. For example, the induction of iPSCs following transfection of Oct 3/4, Sox2, Klf4 and c-Myc using a retroviral system has been achieved, as it has also been via the transfection of Oct4, Sox2, Nanog and Lin28 using a lentiviral system. The former set of transcription factors are known as the Yamanaka factors while the latter are commonly known as the Thomson factors. As would be appreciated by the person of skill in the art, a wide range of modifications to the basic reprogramming factor expression vectors have been made and new modes of delivery have been designed in order to increase efficiency and minimise or remove vector sequences that might otherwise be integrated into the reprogrammed iPSC genome. These methods would be well known to the skilled person and include, but are not limited to:

(i) single cassette reprogramming vectors with Cre-Lox mediated transgene excision;

(ii) reprogramming by non-integrating viruses such as adenovirus or sendai virus. Alternatively, expression of reprogramming factors as proteins provides a means of generating iPSCs which have not undergone integration of the introduced vector DNA into the germline.

Non-viral reprograming methods have also been developed. These include, but are not limited to:

(i) mRNA Transfection—The ability to express reprogramming factors as mRNA offers a method to make iPSCs into which chromosomal integration of viral vectors does not occur. Warren et al. transcribes mRNAs to efficiently express reprogramming factors (Warren et al (2010)). By adding Lin28 to the Yamanaka reprogramming factor protocol, culturing at 5% $O_2$, and including valproic acid in the cell culture medium, the efficiency can be increased. Reprogramming factor mRNAs are commercially available.

(ii) miRNA Infection/Transfection—Several miRNA clusters are strongly expressed in embryonic stem cells. When synthetic mimics of the mature miR-302b and/or miR-372 plus the four lentiviral Yamanaka factors are added to MRC5 and BJ-1 fibroblasts there is a 10- to 15-fold increase in reprogramming efficiency in comparison with the four lentiviral factors alone (Subramanyam et al (2011)). It has also been found that certain miRNAs can reprogram cells at high efficiency without the presence of the Yamanaka factors.

(iii) PiggyBac—PiggyBac is a mobile genetic element (transposon) that in the presence of a transposase can be integrated into chromosomal TTAA sites and subsequently excised from the genome upon re-expression of the transposase. When cloned into a piggyBac vector and co-transfected into MEFs the Yamanaka factors can reprogram cells 14-25 days post-transfection (Kaji et al (2009); Woltjen et al (2009)). The piggyBac vector can be excised from the iPSCs upon re-expression of the transposase.

(iv) Minicircle Vectors—Minicircle vectors are minimal vectors containing only the eukaryotic promoter and cDNA(s) that will be expressed. A Lin28, GFP, Nanog, Sox2, and Oct4 minicircle vector expressed in human adipose stromal cells is able to reprogram cells (Narsinh et al (2011)).

(v) Episomal Plasmids—Transient expression of reprogramming factors as episomal plasmids allows for the generation of iPSCs. For example oriP/EBNA vectors can be constructed with the Yamanaka factors plus Lin28 in one cassette and another oriP/EBNA vector containing SV40 large T antigen (Chuo et al (2011)). These vectors have been shown to be expressed in CD34+ cord blood, peripheral blood, and bone mononuclear cells in media supplemented with sodium butyrate, resulting in iPSC colonies in 14 days. The transfected plasmids are ultimately lost.

In another aspect, the skilled person would also be familiar with adjunct methods which are known to enhance the programming efficiency of cells. For example, even when using the same method there can be variability in iPSC efficiency between cells. Various small molecules have been shown to enhance reprogramming efficiency (Table 4).

TABLE 4

Compounds increasing iPSC reprogramming efficiency

| Treatment | Process affected |
| --- | --- |
| Valproic acid | Histone deacetylase inhibition |
| Sodium butyrate | Histone deacetylase inhibition |
| PD0325901 | MEK inhibition |
| A-83-01 | TGFβ-inhibition |
| SB43152 | TGFβ-inhibition |
| Vitamin C | Enhances epigenetic modifiers, promotes survival of antioxidant effects |
| Thiazovivin | ROCK inhibitor, promotes cell survival |
| PS48 | P13K/Akit activation, promotes glycolysis |
| 5% Oxygen | Promotes glycolysis |

Several known mechanisms enable these molecules to facilitate reprogramming including inhibition of histone deacetylation (Mali et al (2010); Huangfu et al (2008)) blockade of the TGFβ and MEK signalling pathways (Lin et al (2009); Ichida et al (2009)), enhancement of function of epigenetic modifiers (Esteban et al (2010)), inhibition of the ROCK pathway (Noggle et al (2011)) and induction of glycolysis (Zhu et al (2010)). Amongst these small molecules, the histone deacetylase inhibitors valproic acid and sodium butyrate are the most commonly used in reprogramming protocols. It should also be noted that culture of cells in 5% oxygen during the reprogramming process can also increase efficiency of iPSC derivation (Yoshida et al (2009)). For cells that are particularly difficult to reprogram, the addition of a small molecule and culture in hypoxic conditions can yield improvements. Another option is to use embryonic stem cell-conditioned medium (ESCM) to induce expression of endogenous reprogramming factors (Balasubramanian et al (2009)). The efficiency can be improved further with the addition of valproic acid. Such a strategy can also be used to enhance the ability of exogenously introduced reprogramming factors to increase reprogramming efficiency.

To the extent that the stem cells of the present invention are HSCs, methods for generating or preparing HSCs are well known to the person of skill in the art. HSCs can be obtained by direct extraction from the bone marrow or from the blood after the HSCs are released from the bone marrow following e.g., treatment with specific molecules such as GM-CSF. The HSCs can then be purified through their plasma membrane expression of CD34 by for example magnetic beads coated with anti-CD34 or cell sorting by flow cytometry after labelling with fluorescent anti CD34. These so purified HSCs can be induced to T cell differentiation using the OP 9/OP9 DL-L1 system outlined in Example 3 and FIGS. 3-10 inclusive.

Reference to the subject stem cell, in particular iPSC or HSC, being "capable of" differentiating to a T cell expressing a TCR directed to an antigenic determinant should be understood as a reference to a cell which either does, or has the capacity to, transcribe and translate the subject TCR genes and then assemble the TCR heterodimer as a functional receptor on the cell surface. As would be appreciated by the skilled person, in most situations a stem cell such as an iPSC will not, in its undifferentiated form, express a TCR. TCR expression is generally expected to occur once directed differentiation along the T cell lineage has been induced. In one embodiment, the cell is one which, with or without a CAR genetic modification, can be induced to differentiate to a T cell expressing a functional TCR. It should be understood that the capacity of the cell to express a TCR of a particular specificity may be enabled by any suitable means. For example, the cell may have been transfected with genes encoding the two TCR chains (eg. α and β chain) which, when expressed, will associate to form the TCR heterodimer. Alternatively, and in the context of a preferred embodiment of the present invention, the stem cell of the present invention is one which has been generated from a T cell, thymocyte or other cell in which the TCR genes have been rearranged. It has been determined that an iPSC which has been generated from such a cell, if directed to differentiate to a CD4$^+$ or CD8$^+$ T cell under appropriate cell culture conditions, will express the same TCR antigen specificity as the somatic T cell from which the iPSC was derived. Of still further significance, and as discussed in more detail hereinafter, is that it has been determined that with or without transfection of the iPSC or HSC with one or more nucleic acids encoding one or more CARs, or the α and β chains of an antigen/MHC class I specific TCR, the T cell differentiated therefrom is capable of stably expressing both a functional TCR and one or more CARs (and optionally one or more antigen-binding receptors), and is therefore directed to two or more distinct antigenic determinants. Accordingly, such a stem cell is deemed "capable of" differentiating to a T cell and expressing the requisite TCR on the basis that if the iPSC or HSC is provided with the appropriate differentiative signal, this will occur. In this regard, since the rearrangement of the TCR genes is an entirely independent genomic event, the choice of T cell sub-population from which to generate the iPSC need not necessarily be the same as the T cell sub-population which it is sought to ultimately be produced via the directed differentiation of the iPSC. For example, one may select a CD4$^+$ T cell which exhibits an appropriate TCR specificity in order to generate an iPSC. However, once that iPSC has been generated, the skilled person may seek to direct the differentiation of the iPSC to a CD8$^+$ T cell. In this case, by virtue of epigenetic memory, the newly generated CD8$^+$ T cell will exhibit the functionality of a CD8$^+$ T cell but the TCR specificity will be that of the CD4$^+$ T cell from which the iPSC was derived. The converse is also true.

Reference to inducing the "transition" of a somatic cell, such as a T cell, to a multilineage potential phenotype, such as an iPSC, should be understood as a reference to inducing the genetic, morphologic and/or functional changes which are required to change a somatic phenotype to a multilineage (pluripotent) phenotype of the type defined herein.

To the extent that one may elect to render an iPSC capable of producing a TCR via the transfection of the cell with DNA encoding a TCR, it would be appreciated that this transfection may occur at any time point, such as prior to the generation of the iPSC of the present invention, subsequently to the generation of the iPSC, or it may occur simultaneously with the CAR transfection.

As detailed hereinbefore, a somatic cell, in particular a T cell or thymocyte, can be induced to transition into a stem cell, that is a functional state of multilineage differentiation potential. Accordingly, reference to a cell exhibiting "multilineage differentiation potential" or "multilineage potential" should be understood as a reference to a cell which exhibits the potentiality to develop along more than one somatic differentiative path. For example, the cell may be capable of generating a limited range of somatic cell types, such cells usually being referred to as pluripotent or multipotent. These cells exhibit the potential to commit to a more limited range of lineages than a totipotent cell, the latter being a cell which can develop in any of the differentiation directions inherently possible including all the somatic lineages and the gametes.

Cells that are classically termed "progenitor" cells or "precursor" cells fall within the scope of the definition of "multilineage differentiation potential" on the basis that, under appropriate stimulatory conditions, they can give rise to cells of more than one somatic lineage. To the extent that reference to "stem cell" is made herein in terms of the cells generated by the method of the invention, this should be understood as a reference to a cell exhibiting multilineage differentiative potential as herein defined.

In terms of the present invention, it should be understood that the important feature of the subject stem cell is that the multilineage differentiative potential which the cell exhibits includes the capacity to differentiate to a T cell and to express a TCR exhibiting specificity for an antigen of interest. Whether the TCR specificity is induced before or after the stem cell is generated (such as via the transfection of the stem cell with DNA encoding the TCR of interest) is irrelevant. It should be understood that the stem cells claimed herein encompass all stem cells exhibiting the requisite differentiative potential, irrespective of when or how that capability has been introduced. Still further, it should also be understood that the subject stem cells need not be totipotent. Provided that they exhibit the capacity to differentiate along more than one somatic cell lineage and provided that one of these lineages is a T cell lineage, said cells fall within the scope of the present invention.

As detailed hereinbefore, the stem cells provided by the present invention are genetically modified. By "genetically modified" is meant that the subject cell results from some form of molecular manipulation relative to that which is observed in the context of a corresponding unmodified cell. In the context of the present invention, the subject stem cell comprises a nucleic acid molecule encoding a chimeric antigen receptor, and optionally further comprises a nucleic acid molecule encoding an antigen-binding receptor. As disclosed herein, a nucleic acid encoding a receptor, whether a chimeric antigen receptor or an antigen-binding receptor, can be introduced to a stem cell such as an iPSC or an HSC, or to a cell (e.g., a T cell) from which a stem cell is derived; and in both instances, the resulting stem cell which comprises the receptor-encoding nucleic acid is considered herein to be a genetically modified stem cell. A T cell differentiated from a genetically modified stem cell, and a T cell engineered to contain a nucleic acid encoding a genetically engineered CAR or antigen-binding receptor, are also considered herein genetically modified T cells.

Reference to a "nucleic acid molecule" should be understood as a reference to both deoxyribonucleic acid and ribonucleic acid thereof. The subject nucleic acid molecule may be any suitable form of nucleic acid molecule including, for example, a genomic, cDNA or ribonucleic acid molecule. To this end, the term "expression" refers to the transcription and translation of DNA or the translation of RNA resulting in the synthesis of a peptide, polypeptide or protein. A DNA construct, for example, corresponds to the construct which one may seek to transfect into a cell for subsequent expression while an example of an RNA construct is the RNA molecule transcribed from a DNA construct, which RNA construct merely requires translation to generate the protein of interest. Reference to "expression product" is a reference to the product produced from the transcription and translation of a nucleic acid molecule.

Reference to "chimeric antigen receptor" (also known as an "artificial T cell receptor", "chimeric T cell receptor" and "chimeric immunoreceptors") should be understood as a reference to engineered receptors which graft an antigen binding moiety onto an immune effector cell. Typically, these receptors are used to graft the specificity of a monoclonal antibody onto a T cell; with transfection of their coding sequence facilitated by retroviral vectors. More specifically, and without limiting the invention in any way, the most common form of these molecules are fusions of single-chain variable fragments (scFv) derived from monoclonal antibodies, fused to a CD3-zeta chain transmembrane and endodomain. Such molecules result in the transmission of a CD3-zeta chain signal in response to recognition by the scFv of its target. When T cells express this chimeric molecule, they recognize and kill target cells that express the antigen to which the scFv is directed. For example, to target malignant B cells, the specificity of T cells has been redirected using a chimeric immunoreceptor specific for the B-lineage molecule, CD19.

The variable portions of an immunoglobulin heavy and light chain are generally fused by a flexible linker to form a scFv. This scFv is usually preceded by a signal peptide to direct the nascent protein to the endoplasmic reticulum and subsequent surface expression, which the signal peptide ultimately being cleaved. A flexible spacer allows the scFv to orient in different directions to enable antigen binding. The transmembrane domain is generally a typical hydrophobic alpha helix usually derived from the original molecule of the signalling endodomain which protrudes into the cell and transmits the desired signal. Accordingly, reference to an "antigen recognition moiety" should be understood as a reference to an extracellular portion of the receptor which recognises and binds to an antigenic determinant of interest, that is, a target specific binding element. The antigen recognition domain is usually an scFv. There are, however, many other alternatives. For example, an antigen recognition moiety from native T-cell receptor (TCR) alpha and beta single chains have also been used, as have simple ectodomains (e.g., CD4 ectodomain to recognize HIV infected cells) and other recognition components such as a linked cytokine (which leads to recognition of cells bearing the cytokine receptor). In fact any moiety that binds a given target with sufficiently high affinity can be used as an antigen recognition domain. Such molecules are well known to the person of skill in the art and selecting an appropriate molecule for use would be well within the skill of the person in the art. In terms of designing a chimeric antigen receptor, in particular the extracellular domain, the skilled person may include additional moieties which are useful in terms of effecting efficient expression or functioning. For example, and as detailed earlier, the nucleic acid molecule expressing a CAR may be designed to express a signal peptide at the N-terminal end of the antigen recognition moiety. Without limiting the present invention to any one theory or mode of action, a signal peptide directs the nascent protein into the endoplasmic reticulum. This is necessary if the receptor is to be glycosylated and anchored in the cell membrane. Any eukaryotic signal peptide sequence may be used. Generally, a signal peptide natively attached to the amino-terminal is used (e.g., in a scFv with orientation light chain-linker-heavy chain, the native signal of the light-chain is used). In another example the extracellular domain may also comprise a spacer region which may be used to link the antigen recognition domain to the transmembrane domain. It should be flexible enough to allow the antigen recognition domain to orient in different directions to facilitate antigen recognition and binding. The simplest form of a spacer region is the hinge region from IgG1. Alternatives include the $CH_2CH_3$ region of immunoglobulin and portions of CD3. For most scFv based constructs, the IgG1 hinge suffices. Accordingly, the term "spacer" refers to any oligo- or polypeptide that functions to link the transmembrane domain to either the extracellular domain or, the cytoplasmic domain in the polypeptide chain. A spacer domain may comprise up to 300 amino acids, preferably 10 to 100 amino acids and most preferably 25 to 50 amino acids. In yet another example, one may modify the hinge region to change its length and thereby achieve additional functional benefits. For example, in a traditional CAR which comprises a CD8 or CD28 hinge, a single Cysteine (Cys) can be left in the hinge to stabilize dimerization on the T-cell surface. Thus two scFv are usually displayed (bivalent). In another example, one may substitute the Cys (for Ser) so that the stabilizing disulphide bond cannot form thereby preventing dimerization and hence premature activation. The Cys may also be removed entirely. Another design is to display just the VH domain on one CAR and VL domain on another, thus the Cys pairing will align the VH/VL to form a functional monovalent Fv, targeting the antigen of interest.

The antigen recognition moiety of the subject chimeric antigen receptor is operably linked to a T cell activation moiety. By "T cell activation moiety" is meant the sub-region of the receptor which, after antigen recognition and binding, is responsible for transmitting the signal into the T cell to enable its activation and effector mechanism induction. The T cell activation moiety of a CAR is generally located within the intracellular domain (or "endodomain") of the CAR; hence, the intracellular domain of a CAR molecule also typically comprises, or is, its "intracellular signalling domain". A commonly used endodomain component is the intracellular domain of CD3-zeta which contains 3 ITAMs. This transmits an activation signal to the T cell after antigen is bound. CD3-zeta may not provide a fully competent activation signal and additional co-stimulatory signalling is desirable. For example, chimeric CD28 and OX40 can be used with CD3-Zeta to transmit a proliferative/survival signal, or all three can be used together. It should be understood that this intracellular signalling domain of the CAR is responsible for activation of at least one of the normal effector functions of the immune cell, preferably a T cell in which the CAR has been expressed. The term "intracellular signalling domain" refers to the portion of the protein which transduces the effector function signal and directs the cell to perform a specialized function. While usually the entire intracellular signalling domain can be employed, in many cases it is not necessary to use the entire domain. To the extent that a truncated portion of the intracellular signalling domain is used, such truncated portion may be used in place of the intact chain as long as it transduces the effector function signal. The term "intracellular signalling domain" is thus meant to include any truncated portion of the intracellular domain sufficient to transduce the effector function signal.

Preferred examples of intracellular signalling domains for use in a CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signalling sequence: those that initiate antigen-dependent primary activation through the TCR (primary cytoplasmic signalling sequences) and those that act in an antigen-independent manner to provide a secondary or co-stimulatory signal (secondary cytoplasmic signalling sequences). Primary cytoplasmic signalling sequences regulate primary activation of the TCR complex either in a stimulatory way, or in an inhibitory way. Primary cytoplasmic signalling sequences that act in a stimulatory manner may contain signalling motifs which are known as immunoreceptor tyrosine-based activation motifs or ITAMs. Examples of ITAM containing primary cytoplasmic signalling sequences that are of particular use include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signalling molecule in the CAR comprise a cytoplasmic signalling sequence derived from CD3-zeta.

In a preferred embodiment, the cytoplasmic domain of the CAR can be designed to comprise the CD3-zeta signalling domain by itself or combined with any other desired cytoplasmic domain(s) useful in the context of the CAR of the invention. For example, the cytoplasmic domain of the CAR can comprise a CD3 zeta chain portion and a costimulatory signalling region. The costimulatory signalling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD 137), OX40, CD30, CD40, PD-1, TIM3, ICOS, lymphocyte function-associated antigen-1 (LFA-1), CD2, CD7, LIGHT, NKG2C, B7-H3, and a ligand that specifically binds with CD83, and the like. The cytoplasmic signalling sequences within the cytoplasmic signalling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker. In one embodiment, the cytoplasmic domain is designed to comprise the signalling domain of CD3-zeta and the signalling domain of CD28.

As detailed hereinbefore, the antigen recognition moiety is operably linked to the T cell activation moiety. By "operably linked" is meant that the antigen recognition moiety is linked, bound or otherwise associated with the T cell activation moiety, such that upon binding of the antigen recognition moiety to the antigenic determinant, a signal is induced via the T cell activation moiety to activate the subject T cell and enable its effector functions to be activated. This is achieved, for example, via the design of a transmembrane domain.

In one embodiment, the transmembrane domain that is naturally associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. For example, transmembrane regions may be derived from (ie. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signalling domain of the CAR. A glycine-serine doublet provides a particularly suitable linker. Typically, the transmembrane domain is a hydrophobic alpha helix that spans the membrane. Generally, the transmembrane domain from the most membrane proximal component of the endodomain is used.

Reference to an "antigen-binding receptor" should be understood as a reference to engineered receptors which are anchored to the cell surface and bind to an antigen. Similar to chimeric antigen receptors disclosed herein, antigen-binding receptors disclosed herein also comprise an antigen recognition moiety directed to an antigenic determinant. The antigen recognition moiety in an antigen-binding receptor can take the same form and designed in the same way as the antigen recognition moiety of a chimeric antigen receptor, as described herein. Also similar to chimeric antigen receptors disclosed herein, the antigenic recognition moiety in an antigen-binding receptor is operably linked (e.g., through a spacer sequence such as a hinge region) to a transmembrane domain, such that the antigen-binding receptor is anchored to the cell surface. The spacer sequence and the transmembrane domain in an antigen-binding receptor can also be designed in the same way as the spacer sequence and the transmembrane domain of a chimeric antigen receptor, as described above. However, unlike chimeric antigen receptors, the antigen-binding receptor as defined herein is generally non-signalling, and may include an intracellular sequence that lacks a T-cell activation domain. Such a non-signalling antigen-binding receptor can bind to an antigen but does not trigger any signal transduction in T cells, and therefore is also referred to as a "docking receptor" or "anchoring receptor". Certain embodiments of antigen-binding receptors, such as a non-signalling CD47-binding receptor, are further described herein below.

Figure 11:
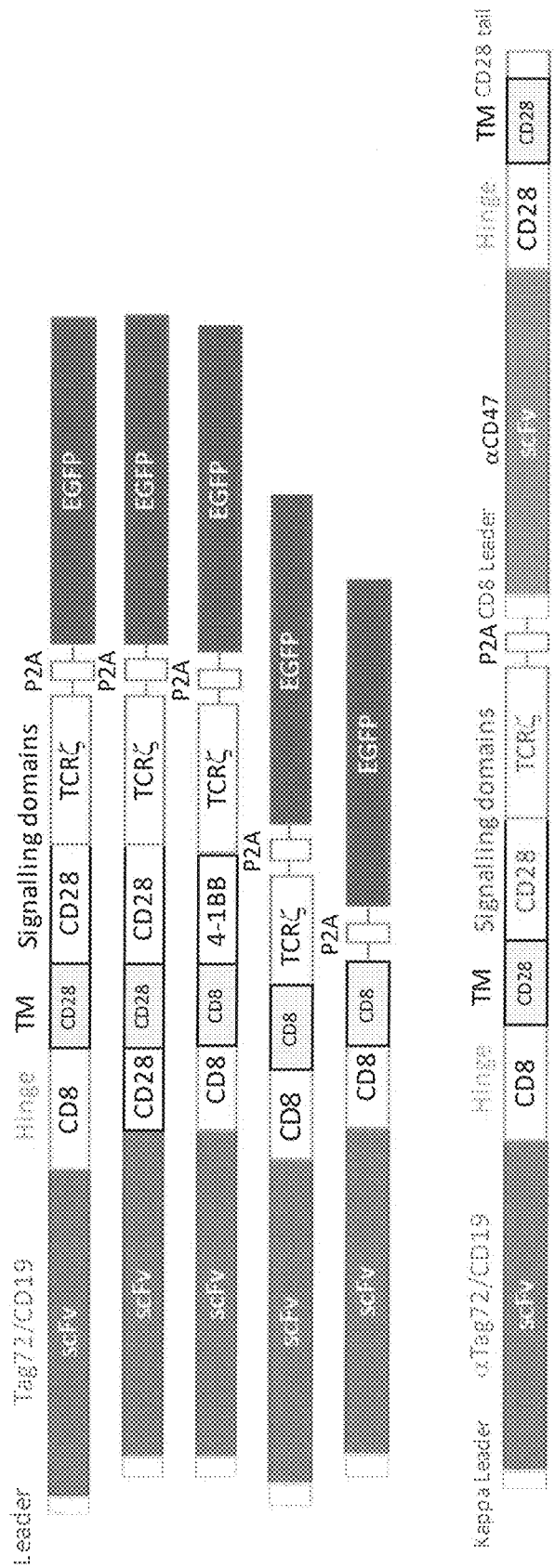
FIG. 11. Schematic diagram of chimeric antigen receptor and antigen-binding receptor constructs. A panel of Chimeric Antigen Receptor (CAR) constructs have been developed—with scFv for either TAG 72 or CD19 (as a positive control). The constructs used either human CD8 or CD28 as hinge and transmembrane regions and CD28, CD3ζ chain or 4-1BB cytoplasmic activation signalling domains. P2A is a signal sequence directing proteolytic cleavage, which in the top five constructs shown in FIG. 11 releases EGFP as a fluorescent reporter of expression, and in the lower (sixth) construct shown in FIG. 11, releases a second CAR receptor construct shown as Leader(CD8)-scFv (anti-CD47)-hinge/TM (CD28)-endodomain tail (CD8) in which the Leader will be processed to release the anti-CD47 scFv on the surface anchored by the hinge/TM and the endodomain tail contains no signalling sequences. Any CD47-binding ectodomain could be used for the purpose of binding to CD47 on target cells, including for example SIRP-alpha. The hinge region may contain cysteine residues to direct dimerization by disulphide bond formation between adjacent hinge domains, which is characteristic of the natural CD8 hinge, or may have the cysteine residues substituted by other residues, such as serine, which do not form disulphide bonds and do not form covalently stabilised dimers. Exemplary sequences of CAR and CD47-binding receptor, as well as various domain sequences suitable for use in constructing a CAR or an antigen-binding receptor, are set forth in SEQ ID NOS: 1-20.

Examples of nucleic acid constructs encoding a CAR and/or an antigen-binding receptor are depicted in FIG. 11, and exemplary sequences for CAR and antigen-binding receptor as well as various domains suitable for use in CARs and/or an antigen-binding receptors are provided in SEQ ID NOS: 1-20.

It would be appreciated by the person of skill in the art that the mechanism by which these genetic modifications are introduced into the cell may take any suitable form which would be well known and understood by those of skill in the art. For example, genetic material is generally conveniently introduced to cells via the use of an expression construct.

In one embodiment, a cell capable of differentiating into a T cell expressing a TCR (i.e., a stem cell such as an iPSC or HSC) or a cell that expresses a TCR from which a stem cell such as an iPSC can be derived, is transfected with a CAR-encoding expression construct. The expression construct can comprise one or more DNA regions comprising a promoter operably linked to a nucleotide sequence encoding a CAR and, optionally, a second DNA region encoding a selectable marker and, optionally, a third DNA region encoding a suicide protein. In this regard, it should be appreciated that one may design the construct with any one or more additional components, such as a suicide gene, which the person of skill in the art would deem useful, as a matter of routine procedure. In the context of the cells of the present invention, which are proposed to be used in vivo to treat patients, the ability to control the killing of the genetically modified cells of the invention, and therefore effect their elimination from the in vivo environment, is highly desirable. Without limiting the present invention to any one theory or mode of action, the adoptive transfer of the cells of the present invention, particularly to the extent that they may be directed to "self" antigens such as tumour antigens or antigens expressed on autoreactive cells, or antigens to which cross-reactivity with self antigens may occur, is not without risk. In this situation, outcomes similar to graft versus host disease may occur, where these cells attack healthy (non-diseased) cells. In the overall therapeutic scheme, these side-effects may still be more desirable than the non-specific systemic killing of healthy tissue which is characteristic of a treatment such as chemotherapy or the uncontrolled killing of healthy tissue in an autoimmune disorder. Nevertheless, killing the cancer cells is paramount but the ability to control the elimination of the cells of the present invention is highly desirable and can be routinely achieved by the very well known and widely used technique of building an inducible suicide gene into the gene construct which is introduced into the stem/T cells of the present invention.

The subject promoter may be constitutive or inducible. Where the subject construct expresses more than one protein of interest, these may be under the control of separate promoters or they may be under the control of a single promoter, such as occurs in the context of a bicistronic vector which makes use of an IRES sequence to facilitate the translation of more than one protein product, in an unfused form, from a single RNA transcript. The subject construct may additionally be designed to facilitate use of the Cre recombinase mediated splicing inducible gene expression system.

Reference to a nucleic acid "expression construct" should be understood as a reference to a nucleic acid molecule which is transmissible to a cell and designed to undergo transcription. The RNA molecule is then transcribed therefrom. In general, expression constructs are also referred to by a number of alternative terms, which terms are widely utilised interchangeably, including "expression cassette" and "vector".

For purposes of introducing nucleic acids encoding multiple receptors, whether the receptor is a CAR, an antigen-binding receptor, or a combination thereof, the multiple receptor-encoding nucleic acids can be placed in one construct which is transfected into a cell. In one embodiment, the multiple receptor-encoding nucleic acids can be included in a multicistronic vector which makes use of an IRES sequence to facilitate the translation of the multiple receptor proteins. In another embodiment, the multiple receptor-encoding nucleic acids can be linked to each other within one expression unit and reading frame, for example, by utilizing a self-cleaving peptide (e.g., P2A) such that one single polypeptide comprising multiple receptor sequences is initially produced and subsequently processed to produce multiple receptors. In another embodiment, the multiple receptor-encoding nucleic acids are placed in separate constructs which are used in transfection.

The expression construct of the present invention may be generated by any suitable method including recombinant or synthetic techniques. To this end, the subject construct may be constructed from first principles, as would occur where an entirely synthetic approach is utilised, or it may be constructed by appropriately modifying an existing vector. Where one adopts the latter approach, the range of vectors which could be utilised as a starting point are extensive and include, but are not limited to:

(i) Plasmids: Plasmids are small independently replicating pieces of cytoplasmic DNA, generally found in prokaryotic cells, which are capable of autonomous replication. Plasmids are commonly used in the context of molecular cloning due to their capacity to be transferred from one organism to another. Without limiting the present invention to any one theory or mode of action, plasmids can remain episomal or they can become incorporated into the genome of a host. Examples of plasmids which one might utilise include the bacterial derived pBR322 and pUC.

(ii) Bacteriophage: Bacteriophages are viruses which infect and replicate in bacteria. They generally consist of a core of nucleic acid enclosed within a protein coat (termed the capsid). Depending on the type of phage, the nucleic acid may be either DNA (single or double stranded) or RNA (single stranded) and they may be either linear or circular. Phages may be filamentous, polyhedral or polyhedral and tailed, the tubular tails to which one or more tubular tail fibres are attached. Phages can generally accommodate larger fragments of foreign DNA than, for example, plasmids. Examples of phages include, but are not limited to the *E. coli* lambda phages, P1 bacteriophage and the T-even phages (eg. T4).

(iii) Baculovirus: These are any of a group of DNA viruses which multiply only in invertebrates and are generally classified in the family Baculoviridae. Their genome consists of double-stranded circular DNA.

(iv) Mammalian virus: Examples of such viruses which infect mammals, include lentivirus, sendai virus, retrovirus, and vaccinia virus.

(v) Artificial Chromosomes: Artificial chromosomes such as yeast artificial chromosomes or bacterial artificial chromosomes.

(vi) Hybrid vectors such as cosmids, phagemids and phasmids: Cosmids are generally derived from plasmids but also comprise cos sites for lambda phage while phagemids represent a chimeric phage-plasmid vector. Phasmids generally also represent a plasmid-phage chimaera but are defined by virtue of the fact that they contain functional origins of replication of both. Phasmids can therefore be propagated either as a plasmid or a phage in an appropriate host strain.

(vii) Commercially available vectors which are themselves entirely synthetically generated or are modified versions of naturally occurring vectors, such as viral vectors.

It would be understood by the person of skill in the art that the selection of an appropriate vector for modification, to the extent that one chooses to do this rather than synthetically generate a construct, will depend on a number of factors including the ultimate use to which the genetically modified cell will be put. For example, where the cell is to be administered in vivo into a human, it may be less desirable to utilise certain types of vectors, such as viral vectors. Further, it is necessary to consider the amount of DNA which is sought to be introduced to the construct. It is generally understood that certain vectors are more readily transfected into certain cell types. For example, the range of cell types which can act as a host for a given plasmid may vary from one plasmid type to another. In still yet another example, the larger the DNA insert which is required to be inserted, the more limited the choice of vector from which the expression construct of the present invention is generated. To this end, the size of the inserted DNA can vary depending on factors such as the size of the DNA sequence encoding the protein of interest, the number of proteins which are sought to be expressed, the number of selection markers which are utilised and the incorporation of features such as linearisation polylinker regions and the like.

The expression construct which is used in the present invention may be of any form including circular or linear. In this context, a "circular" nucleotide sequence should be understood as a reference to the circular nucleotide sequence portion of any nucleotide molecule. For example, the nucleotide sequence may be completely circular, such as a plasmid, or it may be partly circular, such as the circular portion of a nucleotide molecule generated during rolling circle replication (this may be relevant, for example, where a construct is being initially replicated, prior to its introduction to a cell population, by this type of method rather than via a cellular based cloning system). In this context, the "circular" nucleotide sequence corresponds to the circular portion of this molecule. A "linear" nucleotide sequence should be understood as a reference to any nucleotide sequence which is in essentially linear form. The linear sequence may be a linear nucleotide molecule or it may be a linear portion of a nucleotide molecule which also comprises a non-linear portion such as a circular portion. An example of a linear nucleotide sequence includes, but is not limited to, a plasmid derived construct which has been linearised in order to facilitate its integration into the chromosomes of a host cell or a construct which has been synthetically generated in linear form. To this end, it should also be understood that the configuration of the construct of the present invention may or may not remain constant. For example, a circular plasmid-derived construct may be transfected into a cell where it remains a stable circular episome which undergoes replication and transcription in this form. However, in another example, the subject construct may be one which is transfected into a cell in circular form but undergoes intracellular linearisation prior to chromosomal integration. This is not necessarily an ideal situation since such linearisation may occur in a random fashion and potentially cleave the construct in a crucial region thereby rendering it ineffective.

The nucleic acid molecules which are utilised in the method of the present invention are derivable from any human or non-human source. Non-human sources contemplated by the present invention include primates, livestock animals (e.g., sheep, pigs, cows, goats, horses, donkeys), laboratory test animal (e.g., mice, hamsters, rabbits, rats, guinea pigs), domestic companion animal (e.g., dogs, cats), birds (e.g., chicken, geese, ducks and other poultry birds, game birds, emus, ostriches) captive wild or tamed animals (e.g., oxes, kangaroos, dingoes), reptiles, fish, insects, prokaryotic organisms or synthetic nucleic acids.

It should be understood that the receptor-encoding constructs of the present invention may comprise nucleic acid material from more than one source. For example, whereas the construct may originate from a particular microorganism, in modifying that construct to introduce the features defined herein, nucleic acid material from other microorganism sources may be introduced. These sources may include, for example, viral or bacterial DNA (eg. IRES DNA), mammalian DNA (e.g., the DNA encoding a CAR) or synthetic DNA (e.g., to introduce specific restriction endonuclease sites). Still further, the cell type in which it is proposed to express the subject construct may be different again in that it does not correspond to the same organism as all or part of the nucleic acid material of the construct. For example, a construct consisting of essentially bacterial and viral derived DNA may nevertheless be expressed in the mammalian stem cells contemplated herein.

Without limiting the present invention in any way, the present invention preferably uses a DNA construct comprising sequences of a CAR, wherein the sequence comprises the nucleic acid sequence of an antigen binding moiety operably linked to the nucleic acid sequence of an intracellular domain. For example, an intracellular domain that can be used in the subject CAR includes but is not limited to the intracellular domain of CD3-zeta. In another embodiment, the intracellular domain of a CAR includes the intracellular domain of CD3-zeta in operable linkage to the intracellular domain of CD28; and in a further embodiment, the intracellular domain of a CAR includes the intracellular domains of CD3-zeta, CD28 and OX40, in operable linkage with each other.

Vectors derived from retroviruses such as the lentivirus are one example of vectors suitable to achieve long-term gene transfer since they allow long-term, stable integration of a transgene and its propagation in daughter cells. Other suitable viruses include Sendai virus and Vaccinia virus. The vector should be suitable for replication and integration into eukaryotes. Typical cloning vectors contain transcription and translation terminators, initiation sequences, and promoters useful for regulation of the expression of the desired nucleic acid sequence. Viral vector technology is well known in the art and is described, for example, in Sambrook et al (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses and lentiviruses. In general, a suitable vector contains an origin of replication functional in at least one organism, a promoter sequence, convenient restriction endonuclease sites, and one or more selectable markers, (eg. WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to the subject stem cells. A number of retroviral systems are known in the art.

Additional promoter elements, eg. enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, the individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the construct should not be limited to the use of constitutive promoters. Inducible promoters are also contemplated to be used. The use of an inducible promoter provides a molecular switch capable of turning on expression of the CAR polynucleotide sequence to which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like. An epitope tag can also be included in the extracellular domain of a CAR molecule, such as the commonly used short polypeptide c-myc or FLAG, preferably placed within the hinge region, to identify CAR expression by epitope specific targeting agents such as antibodies used in combination for example with flow cytometry.

Reporter genes are used for identifying potentially transfected cells and for evaluating the functionality of regulatory sequences. In general, a reporter gene is a gene that is not present in or expressed by the recipient organism or tissue and encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al, 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription. It will be appreciated by those skilled in the art that a reporter such as eGFP (enhanced green fluorescent protein) can be incorporated as a C-terminal polypeptide extension to a CAR, separated by a self-cleaving peptide such as P2A, which will release the reporter such as eGFP intracellularly.

Methods of introducing and expressing genes in a cell are known in the art. In the context of an expression vector, the vector can be readily introduced into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, eg., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle is a liposome (eg., an artificial membrane vesicle).

In the case where a non-viral delivery system is sought to be utilized, an exemplary delivery vehicle is a liposome. The use of lipid formulations is contemplated for the introduction of the nucleic acids into a host cell. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al (1991)). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, Southern and Northern blotting, RT-PCR and PCR or by detecting the presence or absence of a particular peptide, eg., by immunological means (ELISAs and Western blots).

The TCR and CAR, and antigen-binding receptors in some embodiments, of the present cells are each directed to an antigenic determinant. Reference to "antigenic determinant" should be understood as a reference to any proteinaceous or non-proteinaceous molecule expressed by a cell which is sought to be targeted by the receptor-expressing T cells of the present invention. It would be appreciated that these are molecules which may be "self" molecules in that they are normally expressed in the body of a patient (such as would be expected on some tumour cells or an autoreactive cells) or they may be non-self molecules such as would be expected where a cell is infected with a microorganism (eg. viral proteins). It should also be understood that the subject antigen is not limited to antigens (whether self or not) which are naturally able to elicit a T or B cell immune response. Rather, in the context of the present invention, reference to "antigen" or "antigenic determinant" is a reference to any proteinaceous or non-proteinaceous molecule which is sought to be targeted. As detailed hereinbefore, the target molecule may be one to which the immune system is naturally tolerant, such as a tumour antigen or auto-reactive immune cell antigen. However, it may be desirable (even in light of potential collateral damage) to nevertheless target this antigen, for example to minimize the potentially even more severe side effects which might be observed with a highly non-specific and systemic treatment, such as chemotherapy or immunosuppression, or to reduce the duration of treatment via a highly targeted treatment and/or to maximise the prospect of killing all unwanted cells. Preferably, said molecule is expressed on the cell surface.

It would be understood by the skilled person that in the context of TCR binding, the subject antigenic determinant will take the form of a peptide derived from an antigen, which peptide is expressed in the context of either MHC I or MHC II. In the context of the CAR, since the design of this receptor is based on the use of an immunoglobulin variable region binding domain, the receptor will recognise an epitope present on the native form of the antigen. The subject epitope may be either linear or conformational. It should be understood that the subject antigenic determinant may be any molecule expressed by the cell which is sought to be targeted. That is, the molecule which is targeted may be exclusively expressed by the target cell or it may also be expressed by non-target cells too. Preferably, the subject antigenic determinant is a non-self antigenic determinant or an antigenic determinant which is otherwise expressed exclusively, or at a significantly higher level than by normal cells, by the cells which are sought to be targeted. However, as discussed hereinbefore, depending on the disease condition to be treated, it may not always be possible to identify and target a non-self antigenic determinant.

Reference herein to TCR/CAR receptors which are directed to a "first" antigenic determinant and to a "second" antigenic determinant should be understood as a reference to the fact that the subject receptors are directed to two different epitopic regions. In this regard, however, it should be understood that the receptors may be directed to epitopes on two entirely different cell surface molecules or the receptors may be directed to two different regions/epitopes of the same cell surface molecule. In embodiments where reference is made to a TCR together with multiple CARs, or where reference is made to a TCR with one or more CARs and one or more antigen-binding receptors, it should be understood that each receptor is directed to an antigenic determinant, and the antigenic determinants are preferably different from one another, i.e., the antigenic determinants corresponding to different epitopic regions of the same or different molecules.

Accordingly in one embodiment there is provided a genetically modified mammalian stem cell, or T cell differentiated therefrom, which cell expresses at least one homozygous HLA haplotype, is capable of differentiating to a T cell expressing a TCR directed to a first antigenic determinant, and comprises at least one (i.e., one or more) nucleic acid molecule encoding a chimeric antigen receptor, wherein said receptor comprises an antigen recognition moiety directed to a second antigenic determinant, which antigen recognition moiety is operably linked to a T cell activation moiety, and optionally further comprises a nucleic acid encoding an antigen-binding receptor directed to a third antigenic determinant, and wherein said antigenic determinants are selected from tumour antigens, microorganism antigens or autoreactive immune cell antigens.

In one embodiment, said stem cell is an iPSC. In another embodiment, the stem cell is an HSC.

In still another embodiment, said stem cell is capable of differentiating to a CD4$^+$ T cell or a CD8$^+$ T cell.

In still another embodiment, said TCR is an $\alpha\beta$ TCR.

In yet still another embodiment, said stem cell such as iPSC derived from a T cell or thymocyte, preferably a CD8$^+$ T cell or thymocyte.

As would be appreciated by the skilled person, the identification of antigens which are exclusive to tumours is a significant area of research, but in respect of which there has been limited progress. Since tumour cells are usually self cells, (as opposed to, for example, tumours arising from transplant tissues), it is the case that the antigens which they express are not only self antigens, but are likely to also be expressed by the non-neoplastic cells of the tissue from which the tumour is derived. This is clearly a less than ideal situation due to the side-effects (in terms of destruction of non-neoplastic tissue) which can arise when an anti-neoplastic treatment regime is targeted to such an antigen, but is unavoidable. Nevertheless, some progress has been made in terms of identifying target tumour antigens which, even if not expressed exclusively by tumour cells, are expressed at lower levels or otherwise less frequently on non-neoplastic cells.

The selection of the antigen binding moiety of the invention will depend on the particular type of cancer to be treated. Tumor antigens are well known in the art and include, for example, MAGE, LMP-2, CD19, CD20, WT1, MART-1 glioma-associated antigen, carcinoembryonic antigen (CEA), β-human chorionic gonadotropin, tumour associated glycoprotein 72 (TAG 72), alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), ELF2M, neutrophil elastase, ephrinB2, CD22, insulin growth factor (IGF)-I, IGF-II, IGF-I receptor and mesothelin. CD47 ("don't eat me" receptor) is also a tumour target because it is often highly expressed in cancer cells, as compared to normal cells, and prevents these cancer cells from being attacked by cells of the immune system including, and in particular, scavenger macrophages.

In one embodiment, the tumor antigen comprises one or more epitopes associated with a malignant tumor. Malignant tumors express a number of proteins that can serve as target antigens for an immune attack. These molecules include but are not limited to tissue-specific antigens such as MART-1, WT-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma, the tumor-specific idiotype immunoglobulin constitutes a truly tumor-specific immunoglobulin antigen that is unique to the individual tumor. B-cell differentiation antigens such as CD 19, CD20 and CD37 are other candidates for target antigens in B-cell lymphoma.

Non-limiting examples of antigens include the following: Differentiation antigens such as MART-1/MelanA (MART-I), gplOO (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include CD47, TSP-180, MAGE-4, MAGE-5, MAGE-6, RAGE, NY-ESO, p1 85erbB2, p180erbB-3, cMet, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27. 29\BCAA, CA 195, CA 242, CA-50, CAM43, CD68\P1, CO-029, FGF-5, G250, Ga733\EpCAM, HTgp-175, M344, MA-50, MG7-Ag, MOV 18, NB/70K, NY-CO-1, RCAS 1, SDCCAG16, TA-90\Mac-2 binding protein\cyclophilin C-associated protein, TAAL6, TAG72, TLP, and TPS.

The cells of the present invention are designed to be directed to multiple, i.e., two or more, antigenic determinants. As detailed herein, the multiple antigenic determinants may be, or include, in some embodiments, multiple epitopes of one molecule, or, in other embodiments, epitopes of multiple entirely distinct molecules. The selection of which multiple antigenic determinants should be targeted and, further, whether they should be targeted by the TCR or the CAR is well within the skill of the person in the art. In one embodiment, the cells of the present invention are designed to clear tumour cells and said TCR/CAR are directed to tumour antigens, in particular TAG 72, MAGE and WT1. In another embodiment, said cells are designed to clear autoreactive immune cells and said TCR/CAR are directed to idiotypic T cell or B cell receptors.

Accordingly, in one embodiment there is provided a genetically modified mammalian stem cell, or T cell differentiated therefrom, which cell is capable of differentiating to a T cell expressing a TCR directed to a first tumour antigenic determinant, and comprises one or more nucleic acid molecules encoding one or more chimeric antigen receptors, wherein each chimeric antigen receptor comprises an antigen recognition moiety directed to a tumour antigenic determinant, which antigen recognition moiety operably linked to a T cell activation moiety and wherein said antigenic determinants are selected from TAG 72, CD47, CD19, WT-1, MAGE and EBVLMP2.

Preferably, said genetically modified cell is directed to TAG72 and WT-1. Still more preferably, said CAR is directed to TAG72 and CD47, and said TCR is directed to WT-1.

In one embodiment, said stem cell is an iPSC. In another embodiment, the stem cell is an HSC.

In still another embodiment, said stem cell is capable of differentiating to a CD4$^+$ T cell or a CD8$^+$ T cell.

In still another embodiment, said TCR is an αβ TCR.

In yet still another embodiment, said stem cell (such as iPSC) is derived from a T cell or thymocyte, preferably a CD8$^+$ T cell or thymocyte.

To the extent that the cells of the present invention, in one embodiment, are directed to treating neoplasias, a wide range of CARs have been developed to target known tumour antigens. A non-limiting summary exemplifying some of these CARs, together with the structure of the receptor, is provided in Table 5, below:

TABLE 5

| Target antigen | Associated malignancy | Receptor type |
| --- | --- | --- |
| α-Folate receptor | Ovarian cancer | ScFv-FcεRIγCAIX |
| CAIX | Renal cell carcinoma | ScFv-FcεRIγ |
| CAIX | Renal cell carcinoma | ScFv-FcεRIγ |
| CD19 | B-cell malignancies | ScFv-CD3ζ (EBV) |
| CD19 | B-cell malignancies, CLL | ScFv-CD3ζ |
| CD19 | B-ALL | ScFv-CD28-CD3ζ |
| CD19 | ALL | CD3ζ(EBV) |
| CD19 | ALL post-HSCT | ScFv-CD28-CD3ζ |
| CD19 | Leukemia, lymphoma, CLL | ScFv-CD28-CD3ζ vs. CD3ζ |
| CD19 | B-cell malignancies | ScFv-CD28-CD3ζ |
| CD19 | B-cell malignancies post-HSCT | ScFv-CD28-CD3ζ |
| CD19 | Refractory Follicular Lymphoma | ScFv-CD3ζ |
| CD19 | B-NHL | ScFv-CD3ζ |
| CD19 | B-lineage lymphoid malignancies post-UCBT | ScFv-CD28-CD3ζ |
| CD19 | CLL, B-NHL | ScFv-CD28-CD3ζ |
| CD19 | B-cell malignancies, CLL, B-NHL | ScFv-CD28-CD3ζ |
| CD19 | ALL, lymphoma | ScFv-41BB-CD3ζ vs CD3ζ |
| CD19 | ALL | ScFv-41BB-CD3ζ |
| CD19 | B-cell malignancies | ScFv-CD3ζ (Influenza MP-1) |
| CD19 | B-cell malignancies | ScFv-CD3ζ (VZV) |
| CD20 | Lymphomas | ScFv-CD28-CD3ζ |
| CD20 | B-cell malignancies | ScFv-CD4-CD3ζ |
| CD20 | B-cell lymphomas | ScFv-CD3ζ |
| CD20 | Mantle cell lymphoma | ScFv-CD3ζ |
| CD20 | Mantle cell lymphoma, indolent B-NHL | CD3 ζ/CD137/CD28 |
| CD20 | indolent B cell lymphomas | ScFv-CD28-CD3ζ |
| CD20 | Indolent B cell lymphomas | ScFv-CD28-41BB-CD3ζ |
| CD22 | B-cell malignancies | ScFV-CD4-CD3ζ |
| CD30 | Lymphomas | ScFv-FcεRIγ |
| CD30 | Hodgkin lymphoma | ScFv-CD3ζ (EBV) |
| CD33 | AML | ScFv-CD28-CD3ζ |
| CD33 | AML | ScFv-41BB-CD3ζ |
| CD44v7/8 | Cervical carcinoma | ScFv-CD8-CD3ζ |
| CEA | Breast cancer | ScFv-CD28-CD3ζ |
| CEA | Colorectal cancer | ScFv-CD3ζ |
| CEA | Colorectal cancer | ScFv-FcεRIγ |
| CEA | Colorectal cancer | ScFv-CD3ζ |
| CEA | Colorectal cancer | ScFv-CD28-CD3ζ |
| CEA | Colorectal cancer | ScFv-CD28-CD3ζ |
| EGP-2 | Multiple malignancies | scFv-CD3ζ |
| EGP-2 | Multiple malignancies | scFv-FcεRIγ |
| EGP-40 | Colorectal cancer | scFv-FcεRIγ |
| erb-B2 | Colorectal cancer | CD28/4-1BB-CD3ζ |
| erb-B2 | Breast and others | ScFv-CD28-CD3ζ |
| erb-B2 | Breast and others | ScFv-CD28-CD3ζ (Influenza) |
| erb-B2 | Breast and others | ScFv-CD28mut-CD3ζ |
| erb-B2 | Prostate cancer | ScFv-FcεRIγ |
| erb-B 2, 3, 4 | Breast and others | Heregulin-CD3ζ |
| erb-B 2, 3, 4 | Breast and others | ScFv-CD3ζ |

TABLE 5-continued

| Target antigen | Associated malignancy | Receptor type |
|---|---|---|
| FBP | Ovarian cancer | ScFv-FcεRIγ |
| FBP | Ovarian cancer | ScFv-FcεRIγ (alloantigen) |
| Fetal acetylcholine receptor | Rhabdomyosarcoma | ScFv-CD3ζ |
| GD2 | Neuroblastoma | ScFv-CD28 |
| GD2 | Neuroblastoma | ScFv-CD3ζ |
| GD2 | Neuroblastoma | ScFv-CD3ζ |
| GD2 | Neuroblastoma | ScFv-CD28-OX40-CD3ζ |
| GD2 | Neuroblastoma | ScFv-CD3ζ (VZV) |
| GD3 | Melanoma | ScFv-CD3ζ |
| GD3 | Melanoma | ScFv-CD3ζ |
| Her2/neu | Medulloblastoma | ScFv-CD3ζ |
| Her2/neu | Lung malignancy | ScFv-CD28-CD3ζ |
| Her2/neu | Advanced osteosarcoma | ScFv-CD28-CD3ζ |
| Her2/neu | Glioblastoma | ScFv-CD28-CD3ζ |
| IL-13R-a2 | Glioma | IL-13-CD28-4-1BB-CD3ζ |
| IL-13R-a2 | Glioblastoma | IL-13-CD3ζ |
| IL-13R-a2 | Medulloblastoma | IL-13-CD3ζ |
| KDR | Tumor neovasculature | ScFv-FcεRIγ |
| k-light chain | B-cell malignancies | ScFv-CD3ζ |
| k-light chain | (B-NHL, CLL) | ScFv-CD28-CD3ζ vs CD3ζ |
| LeY | Carcinomas | ScFv-FcεRIγ |
| LeY | Epithelial derived tumors | ScFv-CD28-CD3ζ |
| L1 cell adhesion molecule | Neuroblastoma | ScFv-CD3ζ |
| MAGE-A1 | Melanoma | ScFV-CD4-FcεRIγ |
| MAGE-A1 | Melanoma | ScFV-CD28-FcεRIγ |
| Mesothelin | Various tumors | ScFv-CD28-CD3ζ |
| Mesothelin | Various tumors | ScFv-41BB-CD3ζ |
| Mesothelin | Various tumors | ScFv-CD28-41BB-CD3ζ |
| Murine CMV infected cells | Murine CMV | Ly49H-CD3ζ |
| MUC1 | Breast, Ovary | ScFV-CD28-OX40-CD3ζ |
| NKG2D ligands | Various tumors | NKG2D-CD3ζ |
| Oncofetal antigen (h5T4) | Various tumors | ScFV-CD3ζ (vaccination) |
| PSCA | Prostate carcinoma | ScFv-b2c-CD3ζ |
| PSMA | Prostate/tumor vasculature | ScFv-CD3ζ |
| PSMA | Prostate/tumor vasculature | ScFv-CD28-CD3ζ |
| PSMA | Prostate/tumor vasculature | ScFv-CD3ζ |
| TAA targeted by mAb IgE | Various tumors | FceRI-CD28-CD3ζ (+ a-TAA IgE mAb) |
| TAG-72 | Adenocarcinomas | scFv-CD3ζ |
| VEGF-R2 | Tumor neovasculature | scFv-CD3ζ |

In some embodiments, a CAR comprises an antigen recognition domain which is comprised of an scFv directed to CD19 or TAG-72, and a hinge (Stalk) region and a transmembrane region both of which are derived from CD28 or CD8, and a cytoplasmic endodomain which is also derived from CD28 or CD8 and comprises a T cell activation moiety. The CAR can include a reporter protein (such as EGFP) as a C-terminal polypeptide extension, joined together by a P2A self-cleaving polypeptide to release EGFP after translation. See, e.g., FIGS. 11 and 14.

In a related aspect, it has been further determined that the cells of the present invention are rendered particularly effective if they are engineered to express a non-signalling antigen-binding receptor, for example, a CD47 binding molecule which is unable to effect signal transduction. The expression of a CD47 binding molecule on the cell surface anchors the cell of the present invention to the neoplastic cell to which it is directed, thereby facilitating improved interaction of the TCR and the CAR with their respective ligands. In terms of the treatment of solid tumours, in particular, the increased stability and binding affinity of the interaction of the subject cell enables improved functional outcomes, in terms of neoplastic cell killing, relative to a cell which does not express the subject CD47 binding molecule.

Accordingly, in a related aspect of the present invention there is provided a genetically modified mammalian stem cell, or T cell differentiated therefrom, which cell is capable of differentiating to a T cell expressing a TCR directed to a first antigenic determinant, and comprises (i) a nucleic acid molecule encoding a chimeric antigen receptor, wherein said receptor comprises an antigen recognition moiety directed to a second antigenic determinant, which antigen recognition moiety is operably linked to a T cell activation moiety and (ii) a nucleic acid molecule encoding a non-signalling antigen-binding receptor, such as a non-signalling CD47 binding receptor. In some embodiments, the genetically modified mammalian stem cell expresses at least one homozygous HLA haplotype.

Without limiting the present invention to any one theory or mode of action, CD47 (also known as integrin associated protein) is a transmembrane protein that in humans is encoded by the CD47 gene. CD47 belongs to the immunoglobulin superfamily. CD47 is involved in a range of cellular processes, including apoptosis, proliferation, adhesion, and migration. Furthermore, it plays a key role in immune and angiogenic responses. CD47 is ubiquitously expressed in human cells and has been found to be overexpressed in many different tumor cells.

CD47 is a 50 kDa membrane receptor that comprises an extracellular N-terminal IgV domain, five transmembrane domains, and a short C-terminal intracellular tail. There are four alternatively spliced isoforms of CD47 that differ only in the length of their cytoplasmic tail. Form 2 is the most widely expressed form that is found in all circulating and immune cells. The second most abundant isoform is form 4, which is predominantly expressed in the brain and in the peripheral nervous system. Only keratinocytes express significant amounts of form 1. These isoforms are highly conserved between mouse and man, suggesting an important role for the cytoplasmic domains in CD47 function.

CD47 is a receptor for thrombospondin-1 (TSP-1), a secreted glycoprotein that plays a role in vascular development and angiogenesis. Binding of TSP-1 to CD47 influences several fundamental cellular functions including cell migration and adhesion, cell proliferation or apoptosis, and plays a role in the regulation of angiogenesis and inflammation. CD47 also interacts with signal-regulatory protein alpha (SIRPα), an inhibitory transmembrane receptor present on myeloid cells. The CD47/SIRPα interaction leads to bidirectional signalling, resulting in different cell-to-cell responses including inhibition of phagocytosis (facilitating cancer cell escape), stimulation of cell-cell fusion, and T-cell activation. Still further, CD47 interacts with several membrane integrins, most commonly integrin avb3. These interactions result in CD47/integrin complexes that affect a range of cell functions including adhesion, spreading and migration.

However, although CD47 is ubiquitously expressed, it has been determined that the increased level of expression of CD47 on neoplastic cells is sufficient to facilitate improved responsiveness to, and clearing of, said neoplastic cells by molecules targeting CD47, prior to any substantive adverse impact on non-neoplastic cells.

Reference to a "binding receptor" directed to CD47 should be understood as a reference to any receptor which interacts with CD47. This may take the form of a CD47-binding receptor such as a surface-displayed antibody fragment, for example, and preferably lacking a signalling function.

Accordingly to this embodiment, there is provided a genetically modified mammalian stem cell, or T cell differentiated therefrom, which cell is capable of differentiating to a T cell expressing a TCR directed to a first antigenic determinant, and comprises (i) a nucleic acid molecule encoding a chimeric antigen receptor, wherein said receptor comprises an antigen recognition moiety directed to a second antigenic determinant, which antigen recognition moiety is operably linked to a T cell activation moiety and (ii) a nucleic acid molecule encoding a non-signalling antigen-binding receptor, wherein said receptor comprises an antigen recognition moiety directed to CD47. In some embodiments, the genetically modified mammalian stem cell expresses at least one homozygous HLA haplotype.

As detailed hereinbefore, the subject CD47 binding receptor is a non-signalling receptor. By "non-signalling" is meant that subsequently to binding of the subject receptor to CD47 on a target cell, there is no signal transmitted which would effect a change to the functionality of the cell of the present invention. Rather, the purpose of the CD47 binding receptor is to provide improved anchoring of the subject cell to a target cell, thereby improving the effectiveness of binding of the TCR and the CAR which is directed to the target antigen moiety, such as a tumour antigen moiety.

For example, in one design of a non-signalling antigen-binding receptor, the extracellular domain of the receptor comprises an antigen recognition moiety with binding specificity to CD47, a hinge (stalk) domain, a transmembrane domain, and an intracellular domain which completely lacks a cytoplasmic signalling function. Such non-signalling CD47 binding receptor can be used simply for attachment, not for signalling, so it can drive the docking of T-cells to cancer cells via CD47 binding and without the unwanted activation and kill if engaging to normal CD47-expressing cells.

In some embodiments, the antigen recognition moiety of a non-signalling CD47-binding receptor includes antibody-like domains such as scFv, Fv, Fab etc and any CD47 targeted V-domain, including single human and mammalian V-domains and their equivalent (VhH or vNAR) domains, or may include "alternative protein-based targeting scaffolds" that are well known in the field including, but not restricted to, darpins, anticalins, knottins, ImmE7s, affibodies, Fn3 fibronectin domains etc. The antigen recognition moiety may also include one or more of the V-like domains of SIRPa (the natural ligand of CD47). In one embodiment, the antigen recognition moiety may include one natural V-like domain of SIRPα. In another embodiment, the antigen recognition moiety may include all three of the natural V-like domain of SIRPα. In other embodiments, a molecule suitable for use to provide an antigen recognition moiety in a non-signalling CD47 binding receptor is Hu5F9-G4 scFv molecule (described in U.S. patent application Ser. No. 14/656,431). Hu5F9 has been designed with 3 different versions of VH (1,2,3) and 3 different versions of VL (11,12,13), shown in FIGS. 12A, 12B of U.S. patent application Ser. No. 14/656,431, published as US 20150183874 A1. Liu et al (PLOS One (2015) September 21; 10(9): e0137345) describes Hu5F9-G4 where the selected V-domains were heavy VH-2 comprising 4 unique residue changes in the framework (that differentiate VH-2 from VH-1,3) and light VL-12 comprising 2 unique residue changes in the framework (that differentiate VL-12 from VL-11,13).

In some embodiments, the hinge region of a non-signalling CD47-binding receptor can be the natural SIRPα hinge sequence, or the CD8 or CD28 hinges as typically used in CARs, or alternative hinges well known in the field such as CD4 domains or Mucin peptide hinges. The hinge region can be designed to include one or more Cysteine (Cys) residues in order to allow for dimerization of the receptors. CD28 is a natural dimeric structure linked via a single Cys in the stalk region. Thus, where the stalk region of CD28 is used as the hinge of non-signalling CD47-binding receptor, introduction of an additional Cys may not be necessary, but may provide additional stabilization for dimers.

It will be understood by those skilled in the art that the introduction of nucleic acids encoding a CAR and a non-signalling antigen-binding receptor (such as a non-signalling CD47-binding receptor) into a cell (e.g., a T cell or an iPSC) can be achieved using two separate transfection vectors, or a single bicistronic vector, or a single gene encoding an internal cleavage signal to separate the CAR from the antigen-binding receptor. In one embodiment the internal cleavage signal is P2A, a peptide sequence that directs self-cleavage to separate CAR from the antigen-binding receptor. In a specific embodiment, a non-signalling CD47 binding receptor is expressed as a C-terminal extension of a CAR and separated by a P2A self-cleaving peptide to separate the CAR and the CD47-binding receptor after translation.

Means for modifying the stem cell of the present invention, such that it also expresses a non-signalling CD47 binding molecule, have been described in significant detail hereinbefore in terms of effecting the expression of a chimeric antigen receptor directed to a tumour antigen moiety. The transfection and other methods of achieving receptor expression which are described herein would be understood by the skilled person to be equally applicable in the context of the subject CD47 binding molecule.

In one embodiment, said stem cell is an iPSC. In another embodiment, said stem cell is an HSC.

In another embodiment, said stem cell is capable of differentiating to a CD4+ T cell or a CD8+ T cell.

In still another embodiment, said TCR is an αβ TCR.

In yet still another embodiment, said stem cell such as iPSC is derived from a T cell or thymocyte, preferably a CD8+ T cell or thymocyte, and in some embodiments, a CD8+ T cell or thymocyte with an endogenous TCR directed to a tumour antigen.

In still yet another embodiment, said stem cell is directed to TAG 72 and WT 1. Still more preferably, said CAR is directed to TAG 72 and said TCR is directed to WT 1.

In a further aspect there is provided a method of making a genetically modified mammalian stem cell. The various means for making a genetically modified mammalian stem cell, particularly an iPSC have been described hereinabove.

In a further aspect there is provided a T cell that expresses a TCR directed to a first antigenic determinant, and a chimeric antigen receptor, wherein said receptor comprises an antigen recognition moiety directed to a second antigenic determinant, which antigen recognition moiety is operably linked to a T cell activation moiety. In some embodiments, the T cell expresses at least one homozygous HLA haplotype.

In one embodiment, the T cell expresses multiple chimeric antigen receptors, wherein each chimeric antigen receptor comprises an antigen recognition moiety directed to an antigenic determinant, which antigen recognition moiety is operably linked to a T cell activation moiety.

In one embodiment, the multiple antigenic determinants which the multiple chimeric antigen receptors are directed to are each distinct from said first antigenic determinant to which the TCR expressed on the subject T cell is directed. In another embodiment, the multiple antigenic determinants which the multiple chimeric antigen receptors are directed to, are distinct one from another, and are also distinct from said first antigenic determinant to which the TCR expressed on the subject T cell is directed.

In one embodiment, the multiple CARs are encoded by one contiguous nucleic acid fragment. For example, the multiple CARs are encoded by multiple nucleic acids placed in one vector, which is transfected into a cell to ultimately generate the subject T cell. In a specific embodiment, the multiple CAR encoding nucleic acids can be linked to each other within one expression unit and reading frame (for example, by utilizing a self-cleaving peptide such as P2A), such that one single polypeptide comprising multiple CAR polypeptide sequences is initially produced and subsequently processed to provide multiple CARs. In another embodiment, the multiple CAR-encoding nucleic acids are placed in separate vectors, which are used in transfection to generate the subject T cell.

In another embodiment, the T cell, which expresses one or more CARs, further expresses at least one (i.e., one or more) antigen-binding receptor which comprises an antigen recognition moiety directed to a third antigenic determinant.

In one embodiment, the antigen-binding receptor is a non-signalling antigen-binding receptor; namely, the receptor is anchored to the cell surface of the subject T cell and binds to the third antigenic determinant, but does not transduce signal into the cytoplasmic part of the T cell that would affect the function of the T cell (hence also referred to as a non-T cell signalling antigen-binding receptor). In one embodiment, the antigen-binding receptor comprises an antigen recognition moiety directed to a third antigenic determinant, operably linked to a transmembrane domain, but lacks a T cell activation moiety.

In a specific embodiment, the antigen-binding receptor is a non-signalling antigen-binding receptor directed to CD47. For example, the antigen-binding receptor is a non-signalling CD47-binding molecule.

In some embodiments, the T cell provided herein is CD4+. In other embodiments, the T cell is CD8+.

In some embodiments, the T cell provided herein expresses an αβ TCR. In other embodiments, the T cell provided herein expresses a γδ TCR.

In some embodiments, the multiple antigenic determinants to which the subject T cell is directed, i.e., the first antigenic determinant to which the TCR is directed, the antigenic determinant(s) to which the chimeric antigen receptor(s) is(are) directed, and the antigenic determinant(s) to which the antigen-binding receptor(s) is(are) directed if such antigen-binding receptor(s) is(are) present, can be selected from tumour antigens, microorganism antigens, or autoreactive immune cell antigens. In certain embodiments, the antigenic determinants are selected from tumour antigens. In specific embodiments, the antigenic determinant to which the TCR is directed, is selected from TCR recognized peptides such as WT-1 or EbvLMP2. In other specific embodiments, the antigenic determinants to which a chimeric antigen receptor and an antigen-binding receptor are directed, can be selected from for example, TAG-72, CD19, MAGE, or CD47.

In some embodiments, the subject T cell, which expresses a TCR directed to a first antigenic determinant, and expresses a chimeric antigen receptor which comprises an antigen recognition moiety directed to a second antigenic determinant, operably linked to a T cell activation moiety, is derived from an iPSC or an HSC.

In one embodiment, the iPSC or HSC from which the subject T cell is derived, is a genetically modified iPSC or HSC which is capable of differentiating into a T cell which expresses a TCR directed to said first antigenic determinant, and comprises one or more nucleic acid(s) encoding one or more chimeric antigen receptor, and optionally comprises one or more nucleic acid encoding an antigen-binding receptor(s). In another embodiment, the iPSC or HSC from which the subject T cell is derived, is capable of differentiating into a T cell which expresses a TCR directed to said first antigenic determinant; and one or more nucleic acid(s) encoding one or more chimeric antigen receptor, and optionally one or more nucleic acid encoding an antigen-binding receptor(s), are introduced after the iPSC or HSC has differentiated into a T cell. In some embodiments, the iPSC or HSC from which the subject T cell is derived, expresses at least one HLA haplotype, and the T cell derived from such iPSC or HSC also expresses said at least one HLA haplotype.

In one embodiment, the iPSC from which the subject T cell is derived, is itself derived from a T cell or thymocyte. In one embodiment, the iPSC is derived from a CD8+ T cell or thymocyte. In one embodiment, the iPSC is derived from a T cell or thymocyte, which expresses a TCR directed to the first antigenic determinant, i.e., the same antigenic determinant to which the TCR of the subject T cell derived from the iPSC is directed.

The value of the cells of the present invention is predicated on directing the differentiation of the subject stem cell to a CD4+ or CD8+ T cell. In this regard, reference to "directing" the differentiation of a stem cell to a T cell should be understood to mean that a cell culture system is applied which induces commitment of a stem cell to the T cell lineage and differentiation along that lineage to a mature T cell. Means for effecting the directed differentiation of a stem cell along the T cell lineage are well known to those of skill in the art. For example, and as exemplified herein, the introduction of Notch-dependent signalling into the culture system is known to effect the directed differentiation of stem cells along the T cell lineage. Still further, if this signalling is provided to stem cells in the context of their co-culture over the OP-9 feeder cell layer, particularly efficient differentiation is achieved. Examples of Notch ligands which are suitable for use include, but are not limited to, Delta-like 1, and Delta-4. In this regard, OP-9 cells have been engineered to express Delta-like 1 (OP9-DL1), thereby providing a highly convenient means of generating T cells from stem cells. In another example, and as exemplified herein, the subject stem cells are first cultured in feeder-free conditions to generate mesoderm, followed by co-culture on the OP9-DL1 cell line. A particularly preferred method of achieving the directed differentiation to $CD8^+$ T cells is exemplified herein.

In another aspect there is provided a method for making a T cell that expresses a TCR directed to a first antigenic determinant, and expresses one or more CARs, and optionally one or more antigen-binding receptors. In some embodiments, the T cell also expresses at least one homozygous HLA haplotype.

In one embodiment, the method comprises obtaining a genetically modified stem cell (such as a genetically modified iPSC or HSC) which is capable of differentiating into a T cell which expresses a TCR directed to a first antigenic determinant, and comprises one or more nucleic acid(s) encoding one or more chimeric antigen receptor each directed to an antigenic determinant (preferably distinct from the first antigenic determinant), and optionally further comprises one or more nucleic acid encoding one or more antigen-binding receptor(s) each directed to an antigenic determinant (preferably distinct from the first antigenic determinant); and differentiating such genetically modified stem cell into a T cell. In some embodiments, the genetically modified stem cell also expresses at least one homozygous HLA haplotype.

In another embodiment, the method comprises obtaining a stem cell (such as an iPSC or HSC) which is capable of differentiating into a T cell which expresses a TCR directed to a first antigenic determinant; differentiating the stem cell into a T cell; introducing into the T cell one or more nucleic acid(s) encoding one or more chimeric antigen receptor, each directed to an antigenic determinant (preferably distinct from the first antigenic determinant), and optionally also one or more nucleic acid encoding one or more antigen-binding receptor(s) each directed to an antigenic determinant (preferably distinct from the first antigenic determinant). In some embodiments, the genetically modified stem cell (such as an iPSC or HSC) also expresses at least one homozygous HLA haplotype.

Irrespective of whether a CAR-encoding nucleic acid is introduced into a stem cell before differentiation into a T cell, or introduced into a T cell after differentiation from a stem cell, the stem cell (such as an iPSC) can be itself derived from a T cell or thymocyte. Such T cell and thymocyte can have a TCR specific for a nominal antigen, e.g., a tumour antigen. In one embodiment, the stem cell is an iPSC. In one embodiment, the iPSC is derived from a CD8+ T cell or thymocyte. In another embodiment, the iPSC is derived from a T cell or thymocyte expressing a TCR directed to the same antigenic determinant to which the TCR expressed on the T cell derived from the iPSC is directed.

Reference to "mammal" should be understood to include reference to a mammal such as but not limited to human, primate, livestock animal (e.g., sheep, cow, horse, donkey, pig), companion animal (e.g., dog, coat), laboratory test animal (e.g., mouse, rabbit, rat, guinea pig, hamster), captive wild animal (e.g., fox, deer). Preferably the mammal is a human or primate. Most preferably the mammal is a human.

The development of the present invention has now facilitated the development of means for treating disease conditions characterised by the presence of an unwanted cellular population such as a neoplastic population of cells, virally infected cells, autoreactive immune cells or infection with microorganisms such as antibiotic resistant bacteria. More specifically, the cells of the present invention provide a means of clearing these cells in a more targeted fashion than current highly non-specific methods such as chemotherapy to treat a neoplastic condition, anti-inflammatory therapy to treat the symptoms of autoimmune disease or immunosuppression to manage autoimmunity. In this regard, reference to a disease condition "characterised by the presence of an unwanted cellular population" should be understood as a reference to any condition, a symptom or cause of which is the presence or functioning of a population of cells which can be targeted by virtue of an expressed cell surface antigen and the elimination of some or all of which cells would be beneficial to the patient. Treatment of the subject condition is achieved by administering T cells differentiated from the stem cells of the present invention, the dual TCR/CAR of which T cells are directed to two or more antigenic determinants expressed by the cells which are sought to be cleared.

It should be understood that the "cells" which are sought to be cleared by the T cells of the present invention may be any cell, whether self or non-self. For example, to the extent that the T cells of the present invention are designed to treat a disease condition such as a neoplasia, viral infection or autoimmune disease, the target population of cells which are sought to be cleared are self cells. However, to the extent that the condition which is sought to be treated is, for example, infection by a microorganism, such as antibiotic resistant bacteria or a parasite, the "cell" to be cleared is a foreign cell. In this regard, the cell may be in suspension (such as leukaemic cells which are present in the circulation) or they may be part of a mass (such as a tumour or tissue). To the extent that the condition being treated is a microorganism infection, the cells may correspond to a unicellular microorganism (such as many bacteria) or they may be part of a multicellular organism. The T cells of the present invention are useful for targeting any type of cell which presents in any type of formation.

Accordingly, another aspect of the present invention is directed to a method of treating a condition characterised by the presence of an unwanted population of cells in a mammal, said method comprising administering to said mammal an effective number of stem cells or T cells differentiated therefrom, as hereinbefore defined.

In one embodiment, said condition is a neoplastic condition, a microorganism infection (such as HIV, STD or antibiotic resistant bacteria), or an autoimmune condition.

In another embodiment, said stem cell is an iPSC or an HSC.

In still another embodiment, said stem cell is capable of differentiating to a $CD4^+$ T cell or a $CD8^+$ T cell.

In still another embodiment, said TCR is an $\alpha\beta$ TCR.

In yet still another embodiment, said stem cell such as iPSC is derived from a T cell or thymocyte.

In still another embodiment, the cell further comprises a nucleic acid molecule encoding a non-signalling antigen-binding receptor, wherein said receptor comprises an antigen recognition moiety directed to CD47.

According to these embodiments, in one particular aspect there is provided a method of treating a neoplastic condition, said method comprising administering to said mammal an effective number of stem cells, or T cells differentiated therefrom, as hereinbefore defined wherein said TCR is directed to a first tumour antigenic determinant and said CAR is directed to one or more additional tumour antigenic determinant(s).

In one embodiment, said first tumour antigenic determinant is WT1.

In another embodiment, said second tumour antigenic determinant is TAG72.

In another embodiment, the cell further comprises a nucleic acid molecule encoding a non-signalling antigen-binding receptor, wherein said receptor comprises an antigen recognition moiety directed to CD47.

In another embodiment the genetically modified stem cell also expresses at least one homozygous HLA haplotype.

Reference to a "neoplastic condition" should be understood as a reference to a condition characterised by the presence or development of encapsulated or unencapsulated growths or aggregates of neoplastic cells. Reference to a "neoplastic cell" should be understood as a reference to a cell exhibiting abnormal growth. The term "growth" should be understood in its broadest sense and includes reference to enlargement of neoplastic cell size as well as proliferation.

The phrase "abnormal growth" in this context is intended as a reference to cell growth which, relative to normal cell growth, exhibits one or more of an increase in individual cell size and nuclear/cytoplasmic ratio, an increase in the rate of cell division, an increase in the number of cell divisions, a decrease in the length of the period of cell division, an increase in the frequency of periods of cell division or uncontrolled proliferation and evasion of apoptosis. Without limiting the present invention in any way, the common medical meaning of the term "neoplasia" refers to "new cell growth" that results as a loss of responsiveness to normal growth controls, eg. to neoplastic cell growth. Neoplasias include "tumours" which may be benign, pre-malignant or malignant. The term "neoplasm" should be understood as a reference to a lesion, tumour or other encapsulated or unencapsulated mass or other form of growth or cellular aggregate which comprises neoplastic cells.

The term "neoplasm", in the context of the present invention should be understood to include reference to all types of cancerous growths or oncogenic processes, metastatic tissues or malignantly transformed cells, tissues or organs irrespective of histopathologic type or state of invasiveness.

The term "carcinoma" is recognised by those skilled in the art and refers to malignancies of epithelial or endocrine tissues including respiratory system carcinomas, gastrointestinal system carcinomas, genitourinary system carcinomas, testicular carcinomas, breast carcinomas, prostate carcinomas, endocrine system carcinomas and melanomas. The term also includes carcinosarcomas, e.g. which include malignant tumours composed of carcinomatous and sarcomatous tissues. An "adenocarcinoma" refers to a carcinoma derived from glandular tissue or in which the tumour cells form recognisable glandular structures.

The neoplastic cells comprising the neoplasm may be any cell type, derived from any tissue, such as an epithelial or non-epithelial cell. Reference to the terms "malignant neoplasm" and "cancer" and "carcinoma" herein should be understood as interchangeable.

The term "neoplasm" should be understood as a reference to a lesion, tumour or other encapsulated or unencapsulated mass or other form of growth or cellular aggregate which comprises neoplastic cells. The neoplastic cells comprising the neoplasm may be any cell type, derived from any tissue, such as an epithelial or non-epithelial cell. Examples of neoplasms and neoplastic cells encompassed by the present invention include, but are not limited to central nervous system tumours, retinoblastoma, neuroblastoma, paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural or peritoneal tumours, neuroendocrine tumours and carcinoid tumours.

In one particular embodiment, said neoplastic condition is a leukaemia or lymphoma.

In another embodiment, said neoplastic condition is metastatic.

The subject undergoing treatment or prophylaxis may be any human or animal in need of therapeutic or prophylactic treatment. In this regard, reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

The present invention should therefore be understood to encompass reducing or otherwise ameliorating a condition in a mammal. This should be understood as a reference to the reduction or amelioration of any one or more symptoms of disease. Although it is always most desirable to achieve the cure of a disease, there is nevertheless significant clinical value in slowing the progression of a disease. For example, in the context of a viral infection such as HIV or STD, even if complete cure cannot be achieved, a reduction in the extent of viral load and spread may provide a means of controlling the infection such that the severe immunodeficiency of HIV, for example, which is ultimately fatal is not experienced and a relatively normal life span can be achieved without the severe side effects that are characteristic of the current anti-viral drug cocktails which patients are required to take. In the specific context of neoplastic conditions, the T cells of the present invention, when administered to a patient, down-regulate the growth of a neoplasm. Reference to "growth" of a cell or neoplasm should be understood as a reference to the proliferation, differentiation and/or maintenance of viability of the subject cell, while "down-regulating the growth" of a cell or neoplasm is a reference to the process of cellular senescence or to reducing, preventing or inhibiting the proliferation, differentiation and/or maintenance of viability of the subject cell. In a preferred embodiment the subject growth is proliferation and the subject down-regulation is $CD8^+$ T cell mediated killing. In this regard, the killing may be evidenced either by a reduction in the size of the tumour mass or by the inhibition of further growth of the tumour or by a slowing in the growth of the tumour. In this regard, and without limiting the present invention to any one theory or mode of action, the neoplastic cells may be killed by any suitable mechanism such as direct lysis or apoptosis induction or some other mechanism which can be facilitated by $CD4^+$ or $CD8^+$ T cells, or T cells lacking these CD4 and CD8 markers. The present invention should therefore be understood to encompass reducing or otherwise ameliorating a neoplastic condition in a mammal. This should be understood as a reference to the prevention, reduction or amelioration of any one or more symptoms of a neoplastic condition. Symptoms can include, but are not limited to, pain at the site of tumour growth or impaired metabolic or physiological bodily functions due to the neoplastic condition. It should be understood that the method of the present invention may either reduce the severity of any one or more symptoms or eliminate the existence of any one or more symptoms. The method of the present invention also extends to preventing the onset of any one or more symptoms.

Accordingly, the method of the present invention is useful both in terms of therapy and palliation. To this end, reference to "treatment" should be understood to encompass both therapy and palliative care. As would be understood by the person of skill in the art, although it is always the most desirable outcome that a neoplastic condition is cured, there is nevertheless significant benefit in being able to slow down or halt the progression of the neoplasm, even if it is not fully cured. Without limiting the present invention in any way, there are some neoplastic conditions which, provided they are sufficiently down-regulated in terms of cell division, will not be fatal to a patient and with which the patient can still have a reasonable quality of life. Still further, it should be understood that the present method provides a useful alternative to existing treatment regimes. For example, in some situations the therapeutic outcome of the present method may be equivalent to chemotherapy or radiation but the benefit to the patient is a treatment regime which induces either fewer side effects or a shortened period of side effects and will therefore be tolerated by the patient much better. As detailed above, it should also be understood that the term "treatment" does not necessarily imply that a subject is treated until total recovery. Accordingly, as detailed above, treatment includes reducing the severity of an existing condition or amelioration of the symptoms of a particular condition or palliation. In this regard, where the treatment of the present invention is applied at the time that a primary tumour is being treated it may effectively function as a prophylactic to prevent the onset of metastatic cancer. For example, for certain types of solid tumours, it may still be most desirable to surgically excise the tumour. However, there is always a risk that the entirety of the tumour may not be successfully removed or that there may be escape of some neoplastic cells. In this case, by applying the method of the present invention to lyse any such neoplastic cells, the method is effectively being applied as a prophylactic to prevent metastatic spread.

In accordance with this aspect of the invention, the subject cells are preferably autologous cells which are isolated and genetically modified ex vivo and transplanted back into the individual from which they were originally harvested. However, it should be understood that the present invention nevertheless extends to the use of cells derived from any other suitable source where the subject cells exhibit a similar histocompatability profile as the individual who is the subject of treatment, so that the transferred cells can perform their function of removing unwanted cells, before being subjected to immune rejection by the host. Accordingly, such cells are effectively autologous in that they would not result in the histocompatability problems which are normally associated with the transplanting of cells exhibiting a foreign MHC profile. Such cells should be understood as falling within the definition of being histocompatible. For example, under certain circumstances it may be desirable, necessary or of practical significance that the subject cells are isolated from a genetically identical twin, or from an embryo generated using gametes derived from the subject individual or cloned from the subject individual (in this case the cells are likely to correspond to stem cells which have undergone directed differentiation to an appropriate somatic cell type). The cells may also have been engineered to exhibit the desired major histocompatability profile. The use of such cells overcomes the difficulties which are inherently encountered in the context of tissue and organ transplants.

However, where it is not possible or feasible to isolate or generate autologous or histocompatible cells, it may be necessary to utilise allogeneic cells. "Allogeneic" cells are those which are isolated from the same species as the subject being treated but which exhibit a different MHC profile. Although the use of such cells in the context of therapeutics could result in graft vs host problems, or graft rejection by the host, this problem can nevertheless be minimised by use of cells which exhibit an MHC profile exhibiting similarity to that of the subject being treated, such as a cell population which has been isolated/generated from a relative such as a sibling, parent or child or which has otherwise been generated in accordance with the methods exemplified herein.

It would be appreciated that in a preferred embodiment the cells which are used are autologous. However, due to the circumstances of a given situation, it may not always be possible to generate an autologous stem cell population. This may be due to issues such as the urgency of commencing treatment or the availability of facilities to effect transformation and directed differentiation. In this case, and as detailed hereinbefore, it may be desirable or necessary to use syngeneic or allogeneic cells, such as cells which have been previously transfected and are available as frozen stock in a cell bank. Such cells, although allogeneic, may have been selected for transformation based on the expression of an MHC haplotype which exhibits less immunogenicity than some haplotypes which are known to be highly immunogenic or which has otherwise been generated in accordance with the methods exemplified herein.

Reference to an "effective number" means that number of cells necessary to at least partly attain the desired effect, or to delay the onset of, inhibit the progression of, or halt altogether the onset or progression of the particular condition being treated. Such amounts will depend, of course, on the particular condition being treated, the severity of the condition and individual patient parameters including age, physical conditions, size, weight, physiological status, concurrent treatment, medical history and parameters related to the disorder in issue. One skilled in the art would be able to determine the number of cells of the present invention that would constitute an effective dose, and the optimal mode of administration thereof without undue experimentation, this latter issue being further discussed hereinafter. These factors are well known to those of ordinary skill in the art and can be addressed with no more than routine experimentation. It is preferred generally that a maximal cell number be used, that is, the highest safe number according to sound medical judgement. It will be understood by those of ordinary skill in the art, however, that a lower cell number may be administered for medical reasons, psychological reasons or for any other reasons.

As hereinbefore discussed, it should also be understood that although the method of the present invention is predicated on the introduction of genetically modified cells to an individual suffering a condition as herein defined, it may not necessarily be the case that every cell of the population introduced to the individual will have acquired or will maintain the subject modification and differentiation. For example, where a transfected and expanded cell population is administered in total (i.e. the successfully modified or differentiated cells are not enriched for), there may exist a proportion of cells which have not acquired or retained the genetic modification and/or the desired T cell differentiation. The present invention is therefore achieved provided that the relevant portion of the cells thereby introduced constitute the "effective number" as defined above. However, in a particularly preferred embodiment the population of cells which have undergone differentiation will be subjected to the identification of successfully modified and differentiated cells, their selective isolation.

In the context of this aspect of the present invention, the subject cells require introduction into the subject individual. To this end, the cells may be introduced by any suitable method. For example, cell suspensions may be introduced by direct injection or inside a blood clot whereby the cells are immobilised in the clot thereby facilitating transplantation. The cells may also be introduced by surgical implantation. This may be necessary, for example, where the cells exist in the form of a tissue graft. The site of transplant may be any suitable site, for example, subcutaneously. Without limiting the present invention to any one theory or mode of action, where cells are administered as an encapsulated cell suspension, the cells will coalesce into a mass. It should also be understood that the cells may continue to divide following transplantation. In this regard, the introduction of a suicide gene, as hereinbefore described, provides a convenient means of controlling ongoing division.

The cells which are administered to the patient can be administered as single or multiple doses by any suitable route. Preferably, and where possible, a single administration is utilised. Administration via injection can be directed to various regions of a tissue or organ, depending on the type of treatment required.

In accordance with the method of the present invention, other proteinaceous or non-proteinaceous molecules may be co-administered with the introduction of the transfected cells. By "co-administered" is meant simultaneous administration in the same formulation or in different formulations via the same or different routes or sequential administration via the same or different routes. By "sequential" administration is meant a time difference of from seconds, minutes, hours or days between the transplantation of these cells and the administration of the proteinaceous or non-proteinaceous molecules. For example, depending on the nature of the condition being treated, it may be necessary to maintain the patient on a course of medication to alleviate the symptoms of the condition until such time as the transplanted cells become integrated and fully functional (for example, the administration of anti-viral drugs in the case of an HIV patient). Alternatively, at the time that the condition is treated, it may be necessary to commence the long term use of medication to prevent re-occurrence of the condition. For example, where the subject damage was caused by an autoimmune condition, the ongoing use of a low level of immunosuppressive drugs may be required once the autoreactive cells have been destroyed.

It should also be understood that the method of the present invention can either be performed in isolation to treat the condition in issue or it can be performed together with one or more additional techniques designed to facilitate or augment the subject treatment. These additional techniques may take the form of the co-administration of other proteinaceous or non-proteinaceous molecules or surgery, as detailed hereinbefore.

Yet another aspect of the present invention is directed to the use of stem cells or T cells differentiated therefrom, as hereinbefore defined in the manufacture of a medicament for the treatment of a condition characterised by the presence of an unwanted population of cells in a mammal.

In another embodiment, said stem cell is an iPSC or an HSC.

In still another embodiment, said stem cell is capable of differentiating to a $CD4^+$ T cell or a $CD8^+$ T cell.

In still another embodiment, said TCR is an $\alpha\beta$ TCR.

In yet still another embodiment, said stem cell such as iPSC is derived from a T cell or thymocyte, preferably a $CD8^+$ T cell or thymocyte.

In still another embodiment, the cell further comprises a nucleic acid molecule encoding a non-signalling antigen-binding receptor, wherein said receptor comprises an antigen recognition moiety directed to CD47.

References made herein to "a cell" should be understood as referring to an isolated cell, or an isolated or substantially purified population of cells. In reference to a cell population, by "substantially pure" it is meant that a relevant cell type accounts for at least 70%, 75%, 80%, 85%, 90%, 95%, 98%, 99% or greater percentage of all the cells in the cell population. For example, a cell population is substantially pure for a relevant T cell if such T cell accounts for at least 70%, 75%, 80%, 85%, 90%, 95%, 98%, 99% or greater percentage of all the cells in the cell population.

The present invention is further described by reference to the following non-limiting examples.

EXAMPLES

The present description is further illustrated by the following Examples which demonstrate the development of certain embodiments of the present invention, including dual anti-cancer specific T cells, derived from iPSC cells or HSCs. These examples should not be construed as limiting in any way.

Example 1: Enrichment of Cancer Peptide Antigen-Specific T Cells from Blood WT-1 Specific TCR T-Cell Stimulation and Expansion WT-1 specific T cells are very rare in normal human blood, but can be expanded and enriched in order to be detected. In this context, peripheral blood mononuclear cells (PBMCs) were isolated using Ficoll-Hypaque density gradient centrifugation. Freshly isolated PBMCs were resuspended in tissue culture medium supplemented with human AB serum, L-glutamine and CD28 monoclonal antibody added to act as a co-stimulant of the T cells when WT-1 is present; anti-CD28 alone doesn't activate T cells. PBMCs were then stimulated with Wilm's Tumor 1 (WT-1) peptides overnight at 0.6 nmol/ml for each of the four WT-1 peptides: WT-1$_{37}$ (VLDFAPPGA, SEQ ID NO: 22), WT-1$_{126}$ (RMFPNAPYL, SEQ ID NO: 23), WT-1$_{187}$ (SLGEQQYSV, SEQ ID NO: 24), and WT-1$_{235}$ (CMTWNQMNL, SEQ ID NO: 25), which represent the main HLA Class I binding motifs. Data presented in the examples of this application used WT-1 peptide 1-37 as representative of this family of WT-1 peptides. WT-1 specific T cells can be identified with HLA-WT-1 specific tetramers or by the early induction of the surface molecule CD137 on stimulated but not resting T cells. CD 137 is a member of the tumor necrosis factor (TNF) receptor family. It is also known as 4-1BB. After 24-36 hours, CD137 positive cells (that is WT-1 stimulated T cells) were magnetically separated using a magnetic cell separator. CD137 positive (WT-1 specific TCR) cells were cultured in T cell expansion media consisting of X-Vivo-15 base medium supplemented with human AB-serum, recombinant interleukin 7, interleukin 15 and interleukin 21. The corresponding CD 137 negative cells were further subjected to CD3 magnetic separation. CD3 negative cells (predominantly B cells) were subjected to mitomycin C treatment and used as WT-1 peptide-loaded antigen presenting feeder cells to the induced CD137 positive population, while the remaining CD3 positive cells (non-WT-1 specific) were grown in culture to act as a control T cell type for the down-stream functional assays. Media with the recombinant cytokines were replenished every second day.

For flow cytometry analysis, cells were resuspended in FACs Buffer: 30 μl per 10$^6$ cells. 10 μl of FcR blocking reagent was added to cells for 5 mins at room temperature. 10 μl of HLA-A02 WT-1 tetramer was added and cells incubated for 20 mins at 4° C. protected from light. 50 μl of "T-Cell Activation" Cocktail was added and cells incubated for 20 mins at 4° C. protected from light. 100 μl of FACs Buffer was added plus 2 μl of Aqua Amine and cells incubated for 5 mins, and subsequently centrifuged at 150×g for 5 mins. The supernatant was aspirated or decanted and the pellet resuspended in 100 μl of BD Cytofix/Cytoperm solution per sample and cells incubated for 20 mins at 4° C. Cells were washed in BD/Perm wash. IFN-γ antibody was diluted ¹⁄₁₀₀ in BD/Perm wash solution and incubated with cells for 30 minutes in the dark at 4° C. Cells were washed in BD/Perm wash and resuspended in FACs buffer prior to flow cytometric analysis. FACS data acquisition was done on a Miltenyi Quant cytometer.

T cells with a TCR specific for WT-1 peptide are normally very low in frequency (e.g., Schmeid et al (2015)) showed they are as few 1 per 10$^{-6}$ of CD8+ cells (range 3×10$^{-7}$ to 3×10$^{-6}$ cells). Following the stimulation protocol described above, WT-1 TCR specific T cells increased ~100 fold to ~3.0% (WT-1 patient #1 1.5%; WT-1 patient #2 4.0%; FIG. 1).

Functional Analysis of WT-1 TCR T-Cells

The in vitro expanded T cells were additionally stimulated with autologous antigen presenting cells (B cells transformed with EBV) and primed with the range of WT-1 peptides: WT-1$_{37}$ (VLDFAPPGA), WT-1$_{126}$ (RMFPNAPYL), WT-1$_{187}$ (SLGEQQYSV), and WT-1$_{235}$ (CMTWNQMNL). The T cells were examined by flow cytometry for interferon gamma (IFNγ) production using the fluorescent bead assay. Cells were double labelled for WT-1 peptide specificity via binding to a WT-1 peptide-HLA tetramer (see FIG. 2).

The WT-1 stimulated T cells clearly expressed (80-90%) interferon gamma (IFNγ) (FIG. 2), a well recognised measure of T cell function (e.g., Ghanekar et al (2001)). To potentially increase the level of CD8 T cell activation (targeting WT-1 T cells), use was made of the LAG3 inhibitor IMP 321. LAG3 is normally a "check point blockade", inhibiting the stimulatory function of dendritic cells (DC) and the response to DC's as antigen presenting cells, by CD8 T cells. When added to the WT-1 specific T cell activation assay, there was no effect of IMP 321 at 24 hours, but after 4 days there was a doubling of the rare CD8+WT-1 specific TCR T cells (FIG. 2H).

Example 2: Generation of iPSC from Human Blood T-Cells

For derivation of iPSC from human blood T cells, there are a number of approaches with varying levels of faithful retention of the original T cell properties. iPSC have been produced from a broad repertoire of peripheral blood T lymphocyte pool (T-iPSC) from a normal healthy human. The T-cells were pre-activated, for example, with the mitogen PHA or anti CD3 and anti CD28 antibodies. Using dual retroviral vector cassettes each containing two of the Yamanaka reprogramming factors (Oct4, Sox 2, KLF, cMyc), multiple T-iPSC clones were generated which were validated at the cellular and molecular level, including flow cytometry and qRT-PCR for a range of markers including Nanog, Oct3/4, SSEA 3,4, TRA-1-60 and TRA-1-81. Their pluripotency was confirmed by teratoma formation after injection into NOD-SCID-IL common gamma chain−/− (NSGMice). Confirmation of T cell origin was confirmed by showing that the TCR genes were rearranged.

Figure 3:
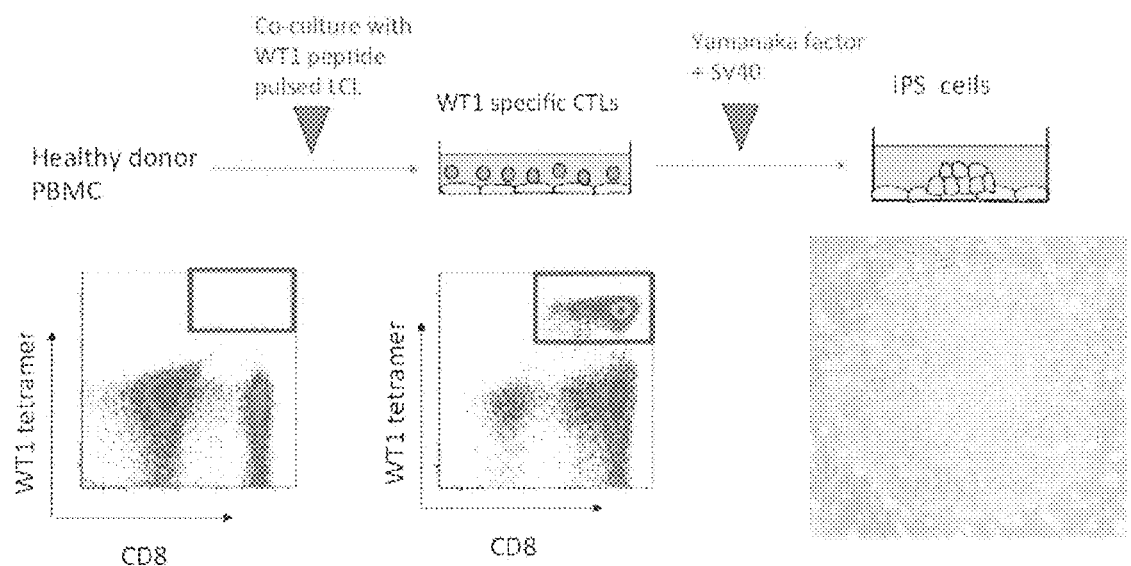
FIG. 3. Production of iPSC from cancer specific (eg WT-1) TCR T cells. Cancer antigen specific T cells are extremely rare in normal blood; they are revealed by stimulation in vitro with WT-1 peptide bound to autologous B cells acting as antigen presenting cells (formed into lymphoblast cells lines (LCL) using EBV), in the presence of cytokines. Cancer antigen specific T cells are shown as double labelled with CD8 (for cytotoxic T cells) and tetramer for HLA-WT-1 binding to the TCR of these CD8+ cells. These cells were then converted into iPSC using the Yamanaka reprogramming factors. The rearranged TCR genes specific for WT-1 were embedded in the TCR locus of the iPSCs.
Figure 4:
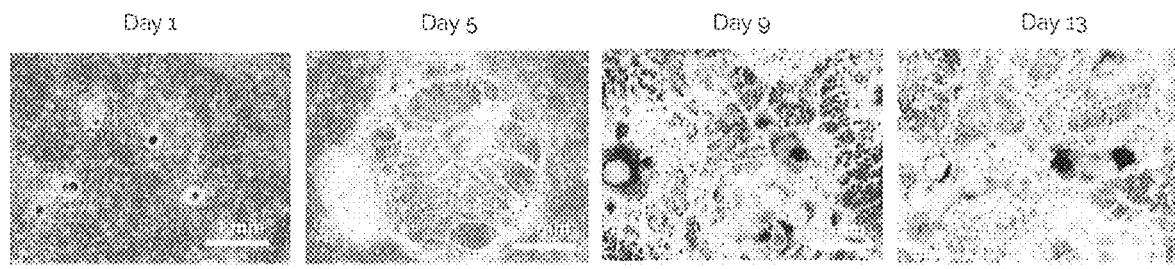
FIG. 4. Morphological progression of iPSC colonies to haemopoietic lineage and lymphoid progenitors after culture for 1, 5, 9 and 13 days on OP9 support cells. Note large numbers of single haemopoietic-like cells by day 13.

The production of iPSC from WT-1 specific blood T cells is summarised in FIG. 3.

Example 3: Induction of Human T Cells from iPSC

This Example shows generation of genuine T cells from iPSC. These T cells were shown to express the key features of typical T cells as normally produced by the thymus. They were shown to express the mainstream T cell αβTCR and CD8 with both β and α chains.

T cells have been induced from iPSC derived from whole adult blood T cells or pre-selected CD8+ T cells, or antigen specific T cells (e.g., those specific for WT-1) (T-iPSC), or adult fibroblasts. There are two basic stages specialisation to haemopoiesis (haemopoietic stem cells or "HSC") and partially lymphoid lineage, by culture on OP9 cells; transfer of these cultured cells to OP cell line genetically modified to express Notch signalling molecule Delta-like Ligand 1 (OP9-DL-L1) for the subsequent induction of T cell differentiation.

Phase 1—Preparatlon of OP9 Support Cells and iPSC Colonies

Day −8: Mitomycin treated Mouse embryonic fibroblast feeder layers were plated onto 0.1% gelatin coated TC plates at 0.3×10$^6$ (14,250 cells/cm$^2$) in 3 mL of MEF media (DMEM+15% FCS+1% pen/strep L-glutamine), and incubated overnight. OP9 cells were pre-prepared by plating onto 0.1% gelatin coated 10 cm TC plates at 0.25×10$^6$ cells in 11 mL OP9 media (αMEM+20% FCS+1% pen/strep).

Day −7: iPS cells were thawed and plated onto the MEF cells, and incubated at 37° C. 5% CO$_2$ for 7 days.

Phase 2—Conversion of iPSCs to Haemopoietic Cells

Day 0: Start of haemopoietic specialisation. The iPS colonies were dissociated and plated onto OP9 for HSC differentiation. The colony suspension was added dropwise for even distribution onto the OP9 plate. Fresh differentiation medium was added on days 1, 5 and 9.

Day 13 Harvest Induced HSC Precursors for T-Cell Differentiation

Figure 5:
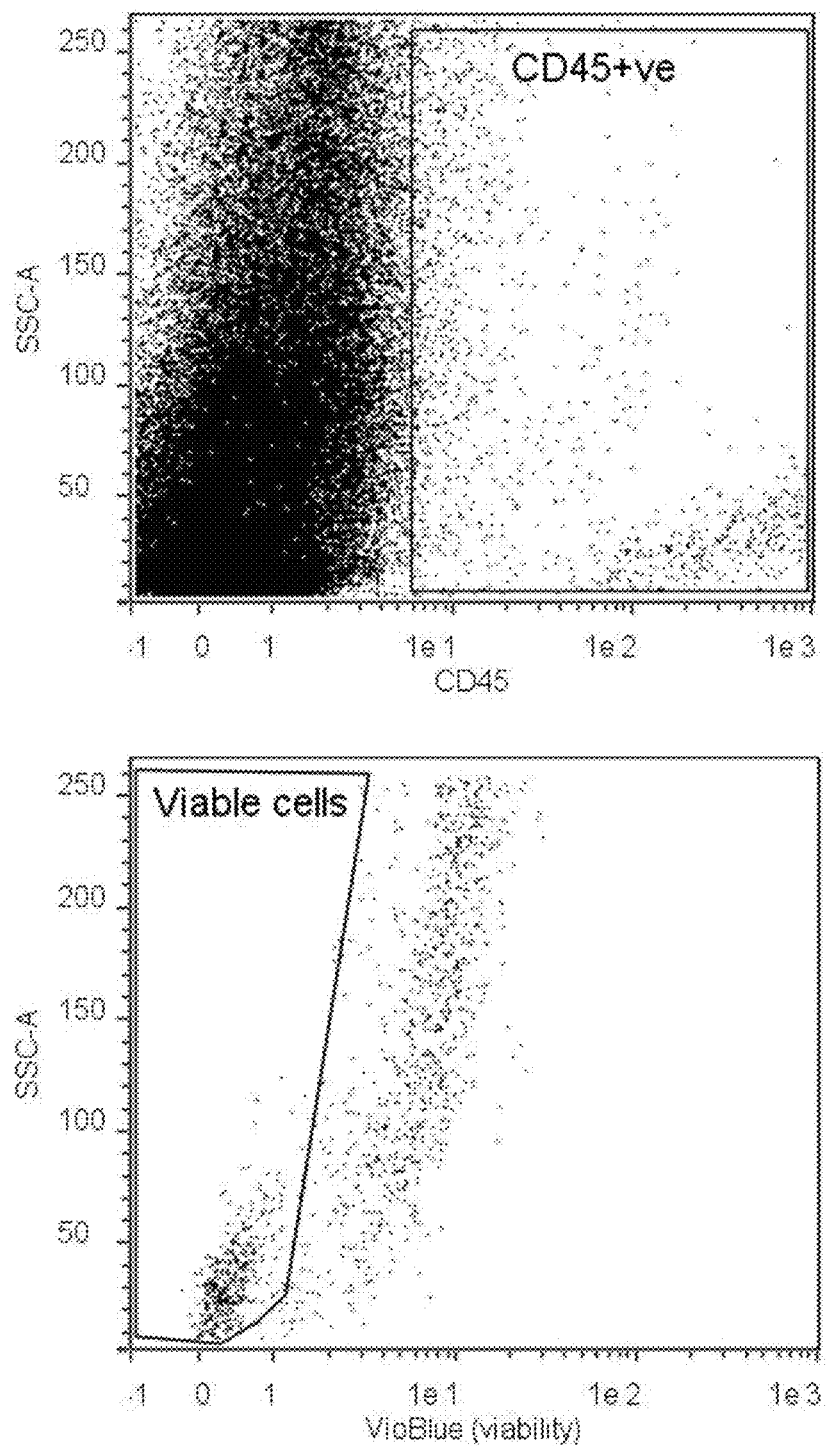
FIG. 5. Flow cytometric analysis of iPSC-derived cells after culture for 13 days on OP9 cells, clearly shows evidence of haemopietic specialisation with the presence of haemopoietic stem cells (HSC) (CD34+CD43+).

Cells cultured on the OP9 cell line were gently removed by Collagenase (working solution 100 g/mL collagenase/HBSS; 37° C. for 1:15 hrs) and the colonies further disrupted intosingle cells by trypsin/EDTA 0.05% at 37° C. for 30 mins. The cells were gently washed and examined by phase Contrast microscopy (FIG. 4) and by flow cytometry (FIG. 5). The haemopoietic nature of the cells was confirmed by flow cytometry (FIG. 5).

Phase 3—Induction of iPSC-Derived HSC to T Cells

Day 13: Induction of T Cell Differentiation: Transfer of Day 13 OP9 Conditioned (Haemopoiesis Induced) Cells to OP9DL-L1 Cells.

In a preferred embodiment, to enhance the efficiency of contact with the OP9DL-L1 cells, the OP9 conditioned cells were purified for $CD34^+CD43^+$ (HSC) and then plated onto the OP9 DLL-1 cells for the first stage of T cell differentiation. A critical component of the process disclosed herein was to collect the cells which initially grew underneath the OP9 DL-L1 cells.

Cells collected from the OP9 cultures were resuspended in T cell differentiation culture medium (OP9 media, SCF 5 ng/mL, Flt3 5 ng/mL, IL-7 5 ng/mL & Vitamin C 100 μM) and the suspension was added dropwise to the OP9 DLL-1 cells and incubated at 37° C. Cells were harvested after 2, 9, 16, 23 and 30 days culture on the OP9 DL-L1 and subjected to flow cytometry analysis (FIG. 6 and FIG. 7).

Figure 7:
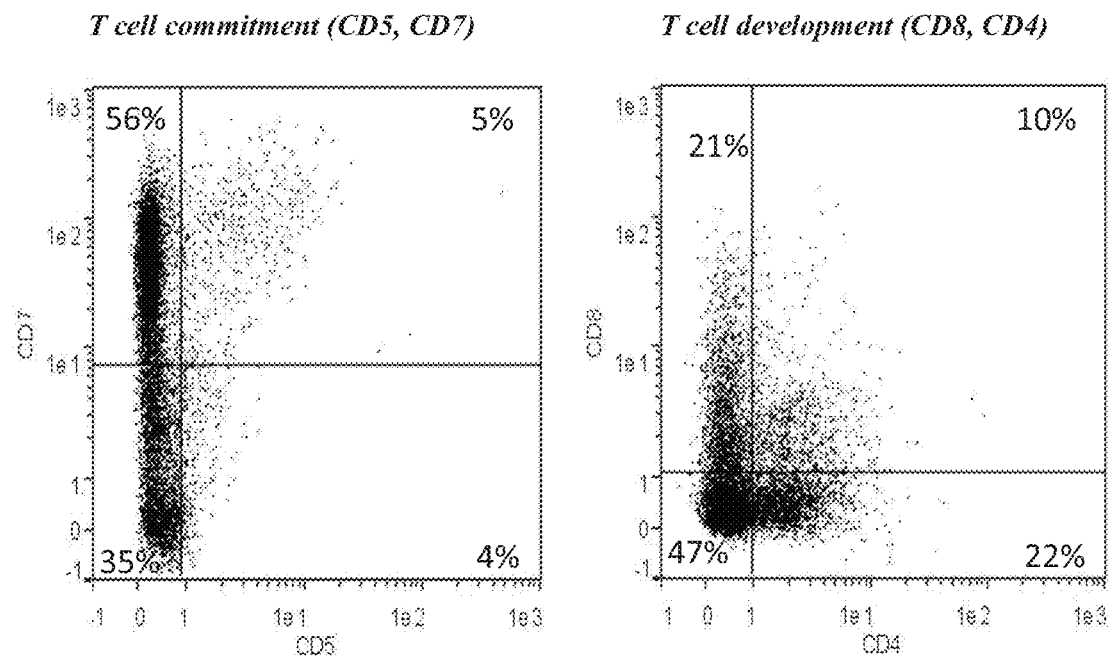
FIG. 7. Flow cytometry for T cell development of iPSC-derived cells after 13 days culture on OP9 cells followed by 9 days culture on OP9 DL-L1 cells. There is clear evidence of commitment to the T cell lineage with expression of CD5 and CD7 and the first stages of thymocyte development with immature (i.e., lacking CD3; data not shown) CD4+, CD8+ "single positive" cells and CD4+CD8+"double positive" cells.

When these cultures were examined for T cell development there was clear evidence of expression of the early markers CD7 and CD9 and the next markers of T cell development with CD4 and CD8 expression (FIG. 7). Even at this early stage there was already ~10% of the cells expressing both CD4+ and CD8+; these CD4+CD8+ cells are characteristic of T cells which develop normally in the thymus cortex (Heng et al (2010)).

Flow cytometry showed progressive development of T cells from the initial expression of CD5, CD7+ then CD8+. Most importantly the induced T cells expressed the phenotype of "optimal, thymus produced" CD8 T cells. They expressed the CD8β chain in addition to the CD8α chain (other reported T cell induction systems do not induce the optimal, signalling CD8β chain; e.g., Themeli et al (2013)). As indications of function they also expressed CD3 with the αβTCR. Furthermore, these cells were present as early as Day 16 of culture on OP9 DL-L1 cells compared to day 30 in other reported systems.

Phase 4 Development of Mature T Cells

Figure 8:
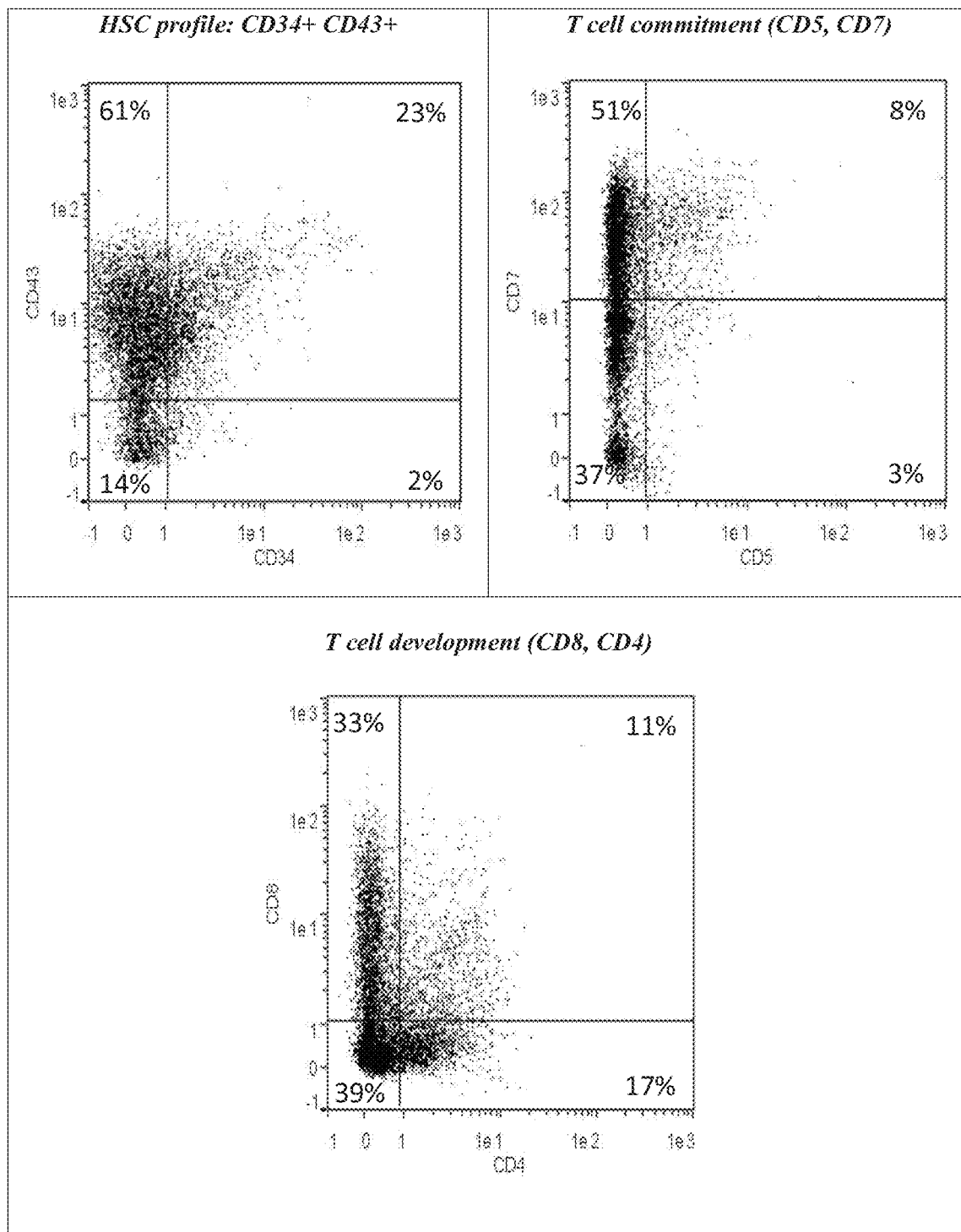
FIG. 8. Flow cytometry for HSC and T cell differentiation in iPSC-derived cells after 13 days culture on OP9 cells followed by 16 days culture on OP9 DL-L1 cells. Immature T cells expressing CD4 and/or CD8 were still clearly present and there was further reduction of HSC from ~60% to ~25%. Most importantly mature CD8+ cells were present and expressed CD3, αβ TCR and the CD8 β chain (in addition to CD8α—not shown)
Figure 8:
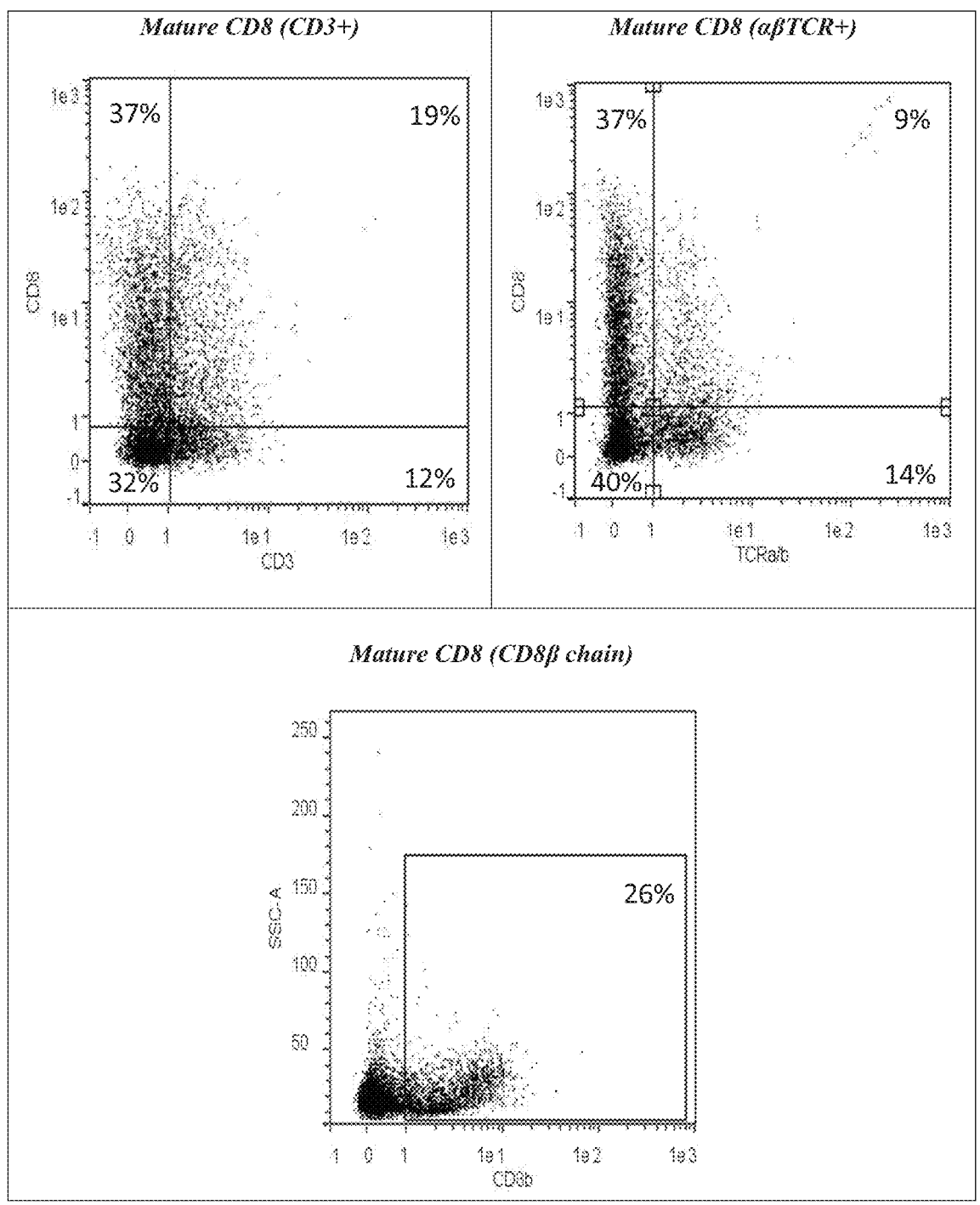

After a further 7 days (a total of 13 days on OP9 cells followed by 16 days on OP DL-L1 cells), these developing T cells made a critical transition to expression of the T cell receptor complex with CD8+ T cells clearly positive for CD3 and the αβTCR; in addition, these cells expressed the important CD8β—these are the desired cells for CAR-T. There was a corresponding further reduction in CD34+ CD43+ HSC (FIG. 8).

This induction system has thus successfully produced mature CD8 T cells from iPSC after 13 days culture on OP9 cells followed by 16 days on OP9DL-L1 cells.

Figure 9:
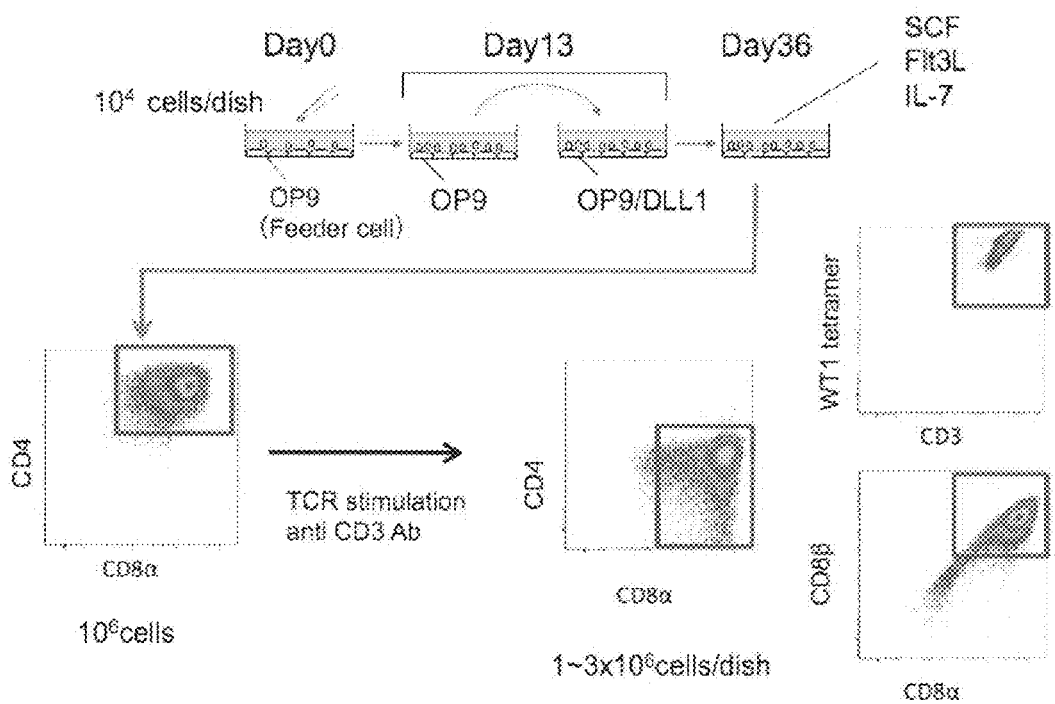
FIG. 9. Schematic representation of the induction of WT-1 specific TCR, CD8αβ T cells from iPSC derived from in vitro expanded WT-1 specific TCR T cells. The treatment of the CD4+CD8+ cells with (low levels) anti CD3 antibody mimic the signalling that occurs within the thymus during positive selection; this increased CD8+ T cells expressing both the CD8α and CD8β chains.
Figure 10:
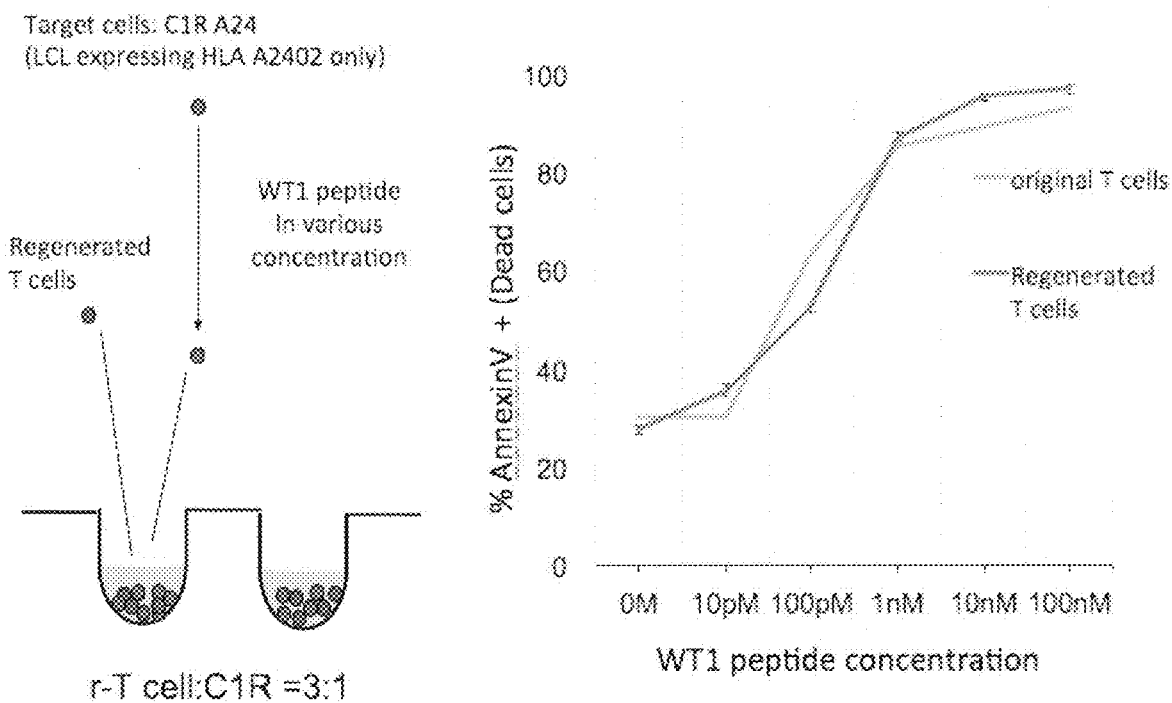
FIG. 10. WT-1 specific TCR, CD8αβ T cells induced from iPSC derived from in vitro expanded WT-1 specific TCR T cells, retained full function (e.g., cytotoxicity to WT-1 expressing targets) equivalent to the original T cells. The effector:target ratio was 3:1; graded concentrations of WT-1 peptides were tested.

Using the process described above, T cells expressing a TCR specific for WT-1 were produced from iPSC which were themselves derived from WT-1 TCR CD8+ T cells (FIG. 9). These iPSC derived WT-1 T cells had a cytotoxic function equivalent to the original T cells from which the iPSC were derived (FIG. 10).

Example 4: Development of CAR Constructs

A component of Chimeric Antigen Receptor (CAR)-T cells is the antigen recognition component of the CAR mediated by the scFv ectodomain, represented by a single-chain Fv (scFv) anchored by a CD8 or CD28 hinge and including a transmembrane (TM) region and the signal transduction of the CAR via the cytoplasmic endodomain-represented by CD28, 4-1BB and the CD3 zeta (CD3) chain. There are also two suitable viral delivery systems—retrovirus and lentivirus. Exemplary CAR and CD47-binding receptor constructs are shown in FIG. 11.

Example 5: Chimeric Antigen Receptor Vector Cloning Strategies

Figure 12:
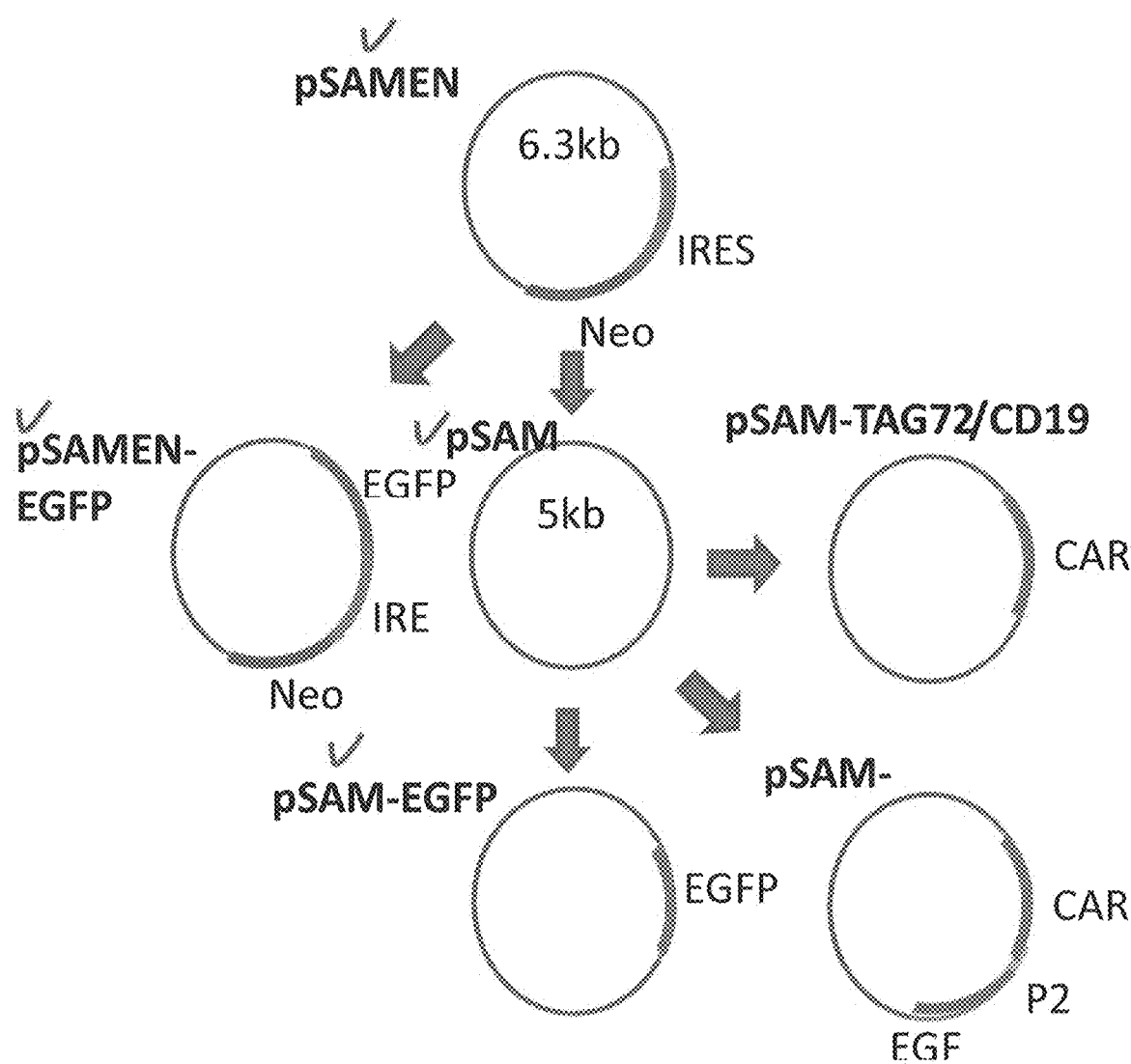
FIG. 12. Retrovirus Transformation scheme. Schematic of the processes undertaken for generating CAR containing retroviral constructs. The CAR construct is cloned into the pSAMEN plasmid vector and is linked to the fluorescent reporter EGFP by a P2A self-cleaving polypeptide to separate the CAR and reporter. When transduction of the cell is successful, the P2A is expressed and cleaved, and the EGFP is identified by flow cytometry and immunofluorescence microscopy.

Exemplary chimeric antigen receptor vector cloning strategies are illustrated in FIGS. 12-13. FIG. 14 shows our $2^{nd}$ generation CAR and the strategy for a non-signalling anti-CD47 construct. Exemplary sequences of chimeric antigen receptors, non-signalling antigen-binding receptors, and the various domains thereof, are provided in SEQ ID NOS: 1-20.

Example 6: Chimeric Antigen Receptor Transduction of T Cells

Lentivirus Production 293T cells were plated onto poly-L-lysine (Sigma) coated 175 cm² flasks. Two hours prior to transfection, medium was replaced with DMEM supplemented with 10% FCS. The lentiviral transfer vector DNA, together with packaging and envelope plasmid DNA were combined and mixed with Lipofectamine2000. The solution was briefly vortexed and incubated at room temperature for 30 min. Following this, the solution was mixed again and then added dropwise to the cells. Flasks were returned to the incubator. Six hours later, fresh growth medium added. Viral supernatant was collected after 48 hrs and cleared by centrifugation at 1500 rpm for 5 min at 4° C. then passed through a 0.45 μm pore PVDF Millex-HV filter (Millipore). Concentration of lentivirus using ultracentrifugation was performed with a Sorval Discovery 100 SE centrifuge using an AH-629 rotor. 30 mL of filtered virus supernatant was added to 36 mL polyallomer conical tubes (Beckman). Centrifugation was performed for 90 min at 20,000 g. Supernatant was completely removed and virus pellets resuspended in 300 μL PBS and stored at −80° C. until use.

Generation of CAR-T Cells

FIG. 11 and SEQ ID NOS: 1-6 show a panel of Chimeric Antigen Receptor (CAR) and CD47-binding receptor constructs that have been developed—with scFv specific for either TAG 72 or CD19 (as a positive control). These constructs use either human CD8 or CD28 as hinge region and CD28, CD3ζ chain or 4-1BB cytoplasmic activation signalling domains. CAR and CD47-binding receptor constructs are cloned into lentiviral vectors as described in the previous paragraph.

Optimal lentiviral transduction of T cells involves their activation at the TCR and co-stimulatory receptors. Accordingly, on day 0, fresh PBMC were collected by apheresis from healthy donors, were enriched for activated T cells with the use of anti-CD3 and anti-CD28 antibodies bound to paramagnetic beads (Dynabeads ClinExVivo CD3/CD28, Invitrogen, Camarillo, Calif., USA) at a ratio of 3:1 (beads: cells). The cells and beads were co-incubated for 1 h at room temperature, andCD3+ cell enrichment was performed with the use of magnet (Invitrogen). Cells in the CD3+ fraction were resuspended in initiation media at a concentration of $1 \times 10^6$ cells/ml in T cell expansion medium with 100 IU/ml IL-2. On day 1, RetroNectin was used to coat cell culture dishes at a concentration of 2 mg/cm2 in a solution of 10 mg/mL in PBS overnight at 4° C. On day 2, the RetroNectin solution was aspirated and the same volume of blocking solution, consisting of 0.5% human serum albumin in PBS, was added to each bag and incubated at room temperature for 30 min. The blocking solution was aspirated, and each bag washed with PBS. Lentiviral supernatant was rapidly thawed and added to each dish with T cell expansion medium with 300 IU/ml IL-2. The cultures were placed back into the incubator and left for at least 24 h. On day 4, the transduction was stopped; cells were resuspended in fresh T-cell expansion medium at a concentration of $0.5-1 \times 10^6$ cells/mL. The cultures were maintained until day 14 and fed every other day with fresh expansion media to maintain cell concentration at $1 \times 10^6$ cells/mL.

Figure 15:
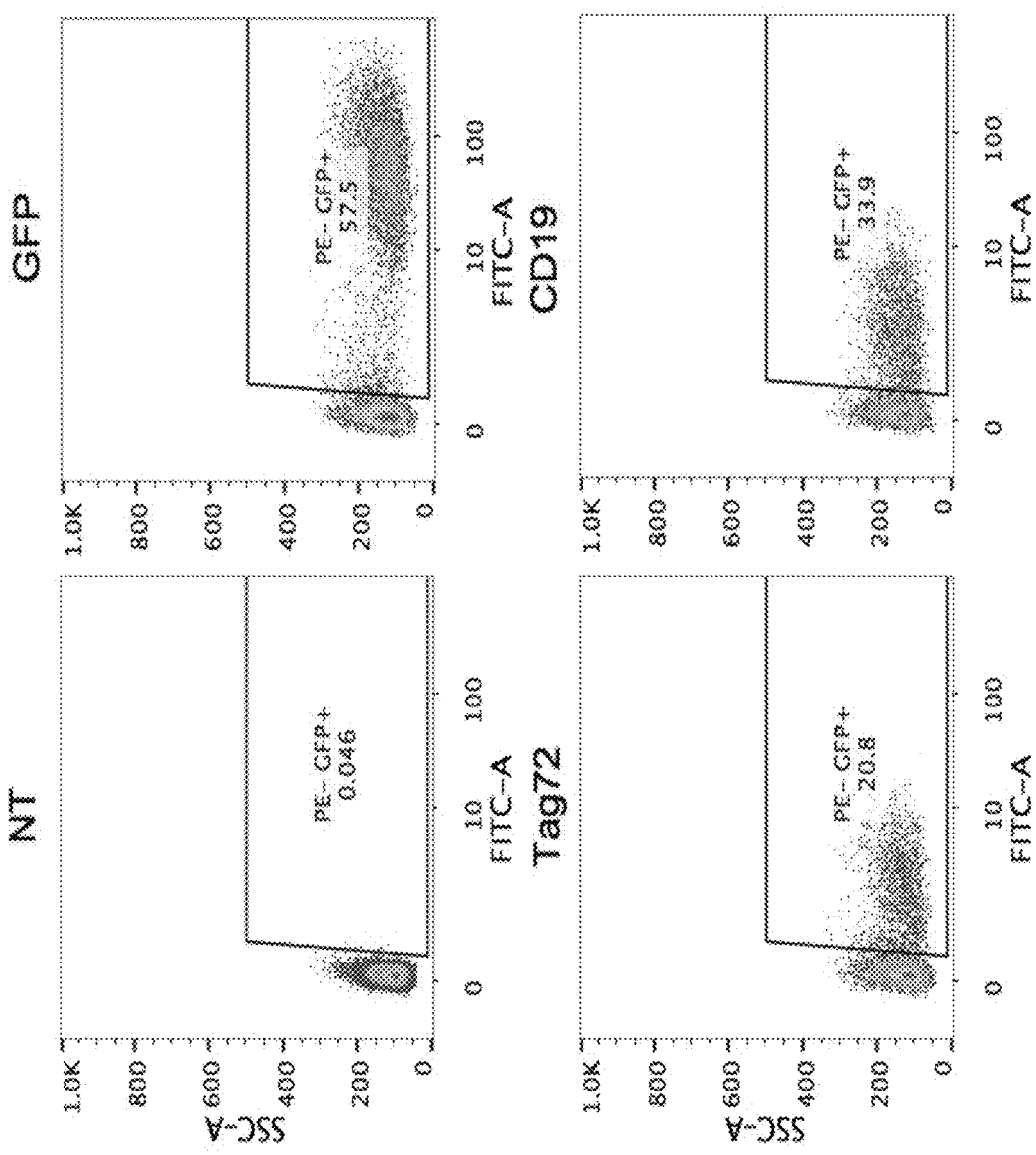
FIG. 15. Flow cytometry analysis of CAR transduced human PBMC derived CD3+ T cells demonstrating successful transduction with the TAG72 Lentivirus CAR construct (20.8% positive compared to <0.1% in the controls) and CD19 lentivirus CAR construct (33.9% positive).
Figure 16:
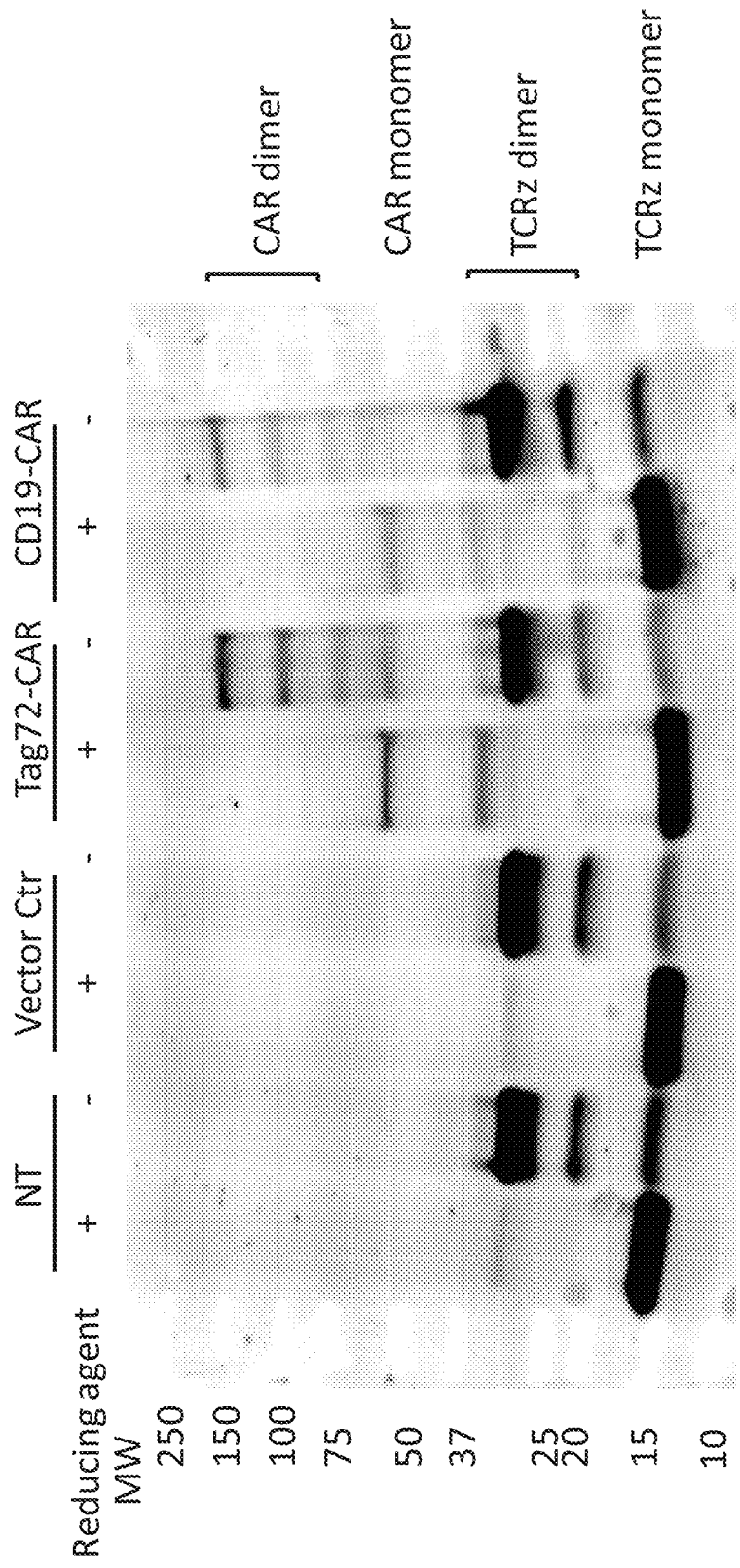
FIG. 16. Western blot analysis confirming protein expression in TAG 27 and CD 19 CAR-transfected T cells.

Initially blood derived human T cells were subjected to CAR transduction, the success of which was measured by flow cytometry, depicting the eGFP+ cells (FIG. 15). This was also confirmed by Western Blot analysis (FIG. 16).

Assessing the Functionality of the CAR-T Cells

The TAG-72 CAR-T cells (created from normal PBMC) were examined for their ability to kill TAG72 expressing target cancer cells in vitro. The real time cell monitoring system (xCELLigence) was employed to determine the killing efficiency of CAR-T cells in vitro. $10,000-2 \times 10^6$ target cells/100 µL (for example the TAG72+ ovarian cancer cell line CaOV4) were deposited into RTCA plates. In some instances, tethering of target cells by anti-hCD40 or by human fibronectin pre-coating of the plate may be required. Target cells are maintained at 37° C., 5% $CO_2$ for 3-12 h to allow for cellular attachment. Following attachment of target cells, CAR-T effector cells were added at variable effector:target ratios (ranging from 1:1 to 10:1). In some experiments, CAR-T effector cells were isolated based of GFP expression of CAR-T cells via FACS prior to use. Co-cultures were maintained in optimal growth conditions for at least 12 h. Cellular impedance was monitored throughout; a decrease in impedance is indicative of cell detachment and ultimately cell death.

Figure 17:
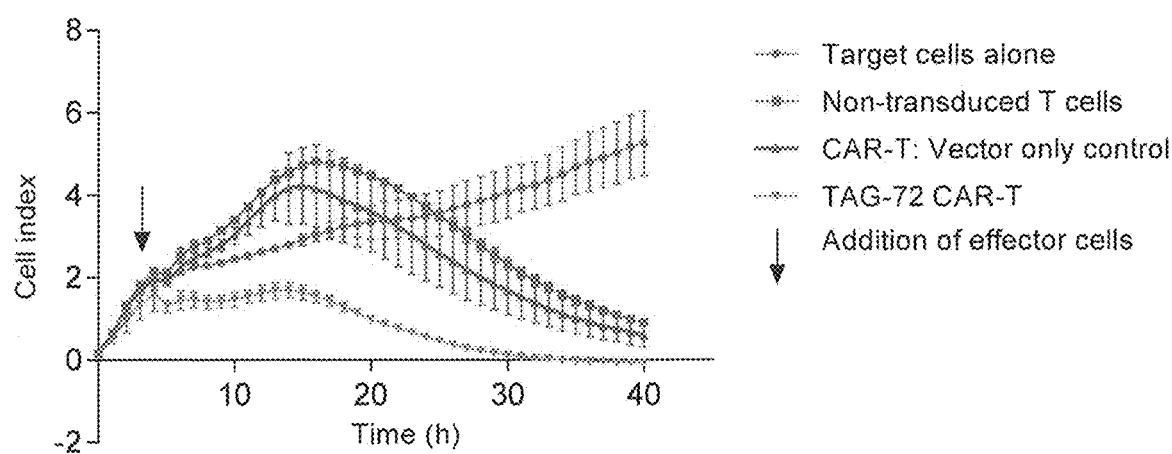
FIG. 17. TAG-72 CAR-T mediated killing of ovarian cancer (TAG72+) target cells. Effector:target ratio (E:T)=1:1. TAG-72 CAR-T effector cells (GFP positive cells) developed from CD3 activated normal blood T cells, were isolated as >95% pure via FACS and subsequently stimulated for enhance cytolytic activity for 72 h in the presence of immobilised αCD3/αCD28 and IL-2 before use. Change in cell impedance (represented here as the arbitrary unit Cell Index) was monitored over 40 h and compared to stimulated non-transduced $CD3^{+ve}$ cells isolated from PBMCs and stimulated vector only CAR-T cells. TAG72 CAR-T cells showed the highest killing however CD3/CD28 activated non-CAR-T cells also showed killing, albeit to a much lesser degree.
Figure 18:
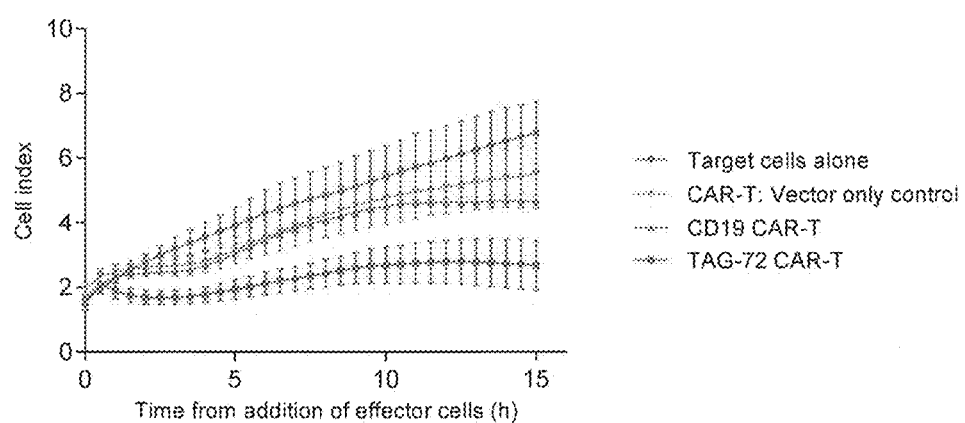
FIG. 18. Determining the specificity of TAG-72 CAR-T killing. TAG-72 and CD19 CAR-T respectively were isolated via FACS and immediately added to TAG-$72^{hi}$/CD$19^{low}$ target cells without in vitro stimulation (E:T=5:1). Change in cell impedance (represented here as the arbitrary unit Cell Index) was monitored over 15 h. TAG-72 CAR-T cells showed strong killing of the cell line. CD19 CAR-T cells were the same as non-CAR T cell controls.

FIG. 17 shows results from this experiment monitored over 40 hours. The ovarian cancer cell line CaOV4 grew consistently over this time period (blue line). In contrast, cultures supplemented with TAG-72 specific CAR T cells showed an initial growth phase that was significantly less than that of target cells alone, followed by gradual elimination of the target cells over time (purple line). To overcome the non-specific killing due to CD3/CD28 activation, the TAG 72 CAR-T cells were isolated by flow cytometry and compared to CD19 CAR-T cells and non-CAR-T cells-without prior CD3/CD28 activation (FIG. 21). The data shown in FIG. 21 indicate strong antigen specificity of TAG-72 CAR-T cells in the first 24 hours of culture with TAG-72 expressing cancer cells, since negative controls of vector only transfected T cells and non-transfected T cells showed no killing of the cancer cells in this time frame.

The above studies were performed on polyclonal T cells derived from peripheral blood. To demonstrate CAR-transduction of mono-specific T cells expressing a TCR specific for a nominal cancer peptide antigen, WT-1 TCR specific T cells derived from iPSC formed from WT-1 specific TCR, were transduced by TAG 72 CAR lentivirus. FIG. 22A shows successful CAR transduction of these WT-1 specific TCR CD8+ T cells themselves derived from iPSC produced from WT-1 specific T cells. The CAR contained the specificity for TAG 72. Most importantly, FIG. 22B shows the successful transduction of WT-1 specific TCR CD8+ T cells themselves derived from iPSC produced from WT-1 specific T cells, with a CAR construct for both TAG 72 and CD47. This indicates that T cells can be produced with three specificities for cancer: WT-1 (TCR), TAG 72 (CAR) and CD47 (truncated, CD47-binding receptor).

The results demonstrate the development of dual specific CAR-transduced cancer specific TCR (WT-1) derived from iPSCs, which were themselves derived from WT-1 specific TCR T cells from normal adult blood.

Figures 20A, 20B, 20C, 20D, 20E, 20F, 20G, 20H, 20I:
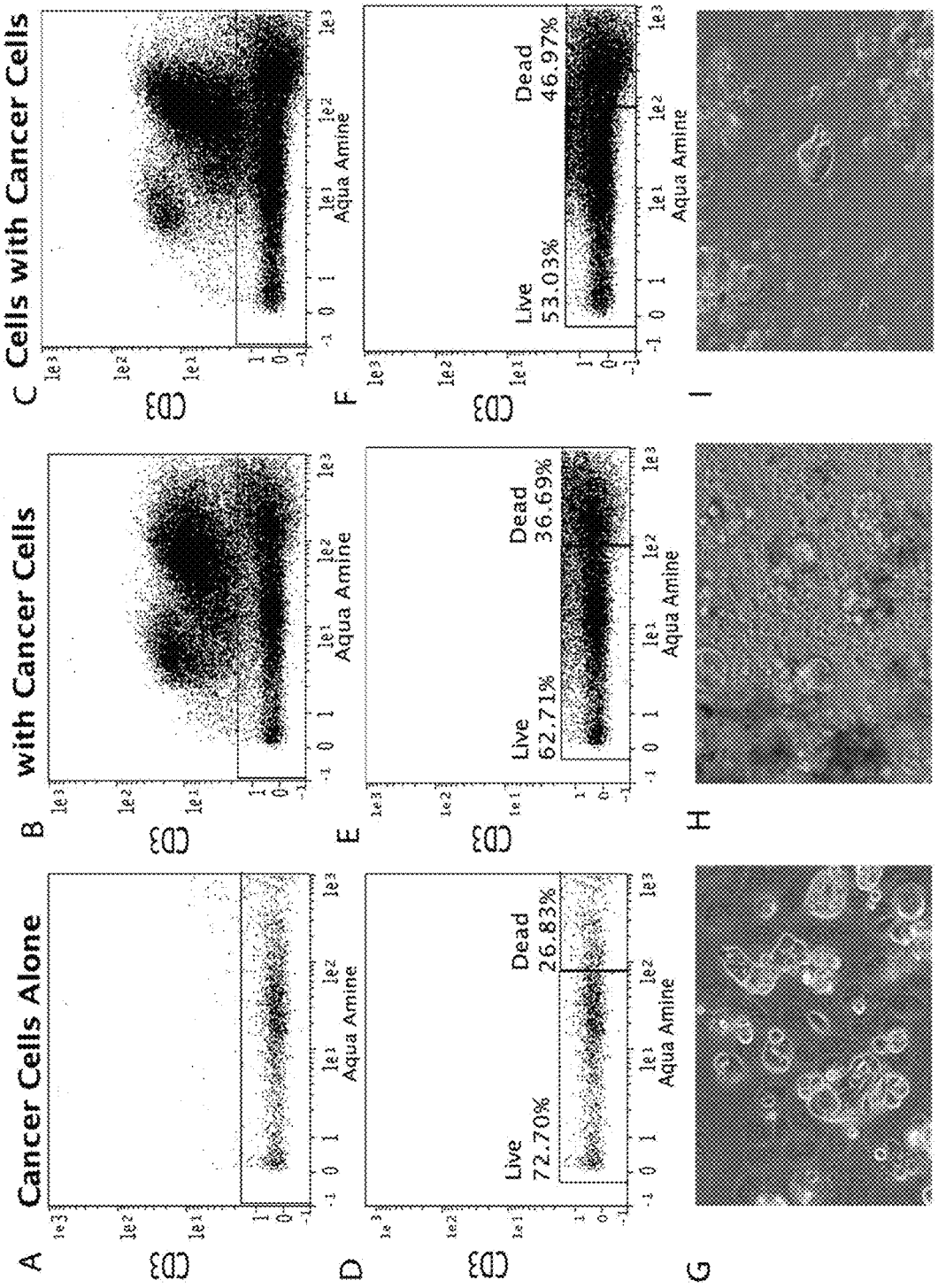
FIG. 20A-20I. Cytotoxic function of WT-1 specific TCR T cells, and dual specific TAG 72 CAR/WT-1 TCR T cells. WT-1 specific TCR T cells and dual specific TAG72 CAR/WT-1 TCR T cells were incubated in monolayer cultures with the ovarian cancer cell line CAOV4 to for 24 hours to assess cytotoxicity. Despite the low effector:target ratio of 2:1 (necessary because of the low numbers of effectors obtained), there was specific killing with WT-1 TCR T cells and this was increased further with transduction with the TAG72 CAR. The technique is based on AquaAmine which stains amines within the cell. When a cell dies or is dying the compromised cell membrane allows the dye to infiltrate the cell and stain the amines more intensely. Cell cytotoxicity is therefore depicted by an increased staining intensity of cellular amines. Note: live cells will still give some (albeit low) positive staining because some amines reside on the cell surface. A, D, G: CAOV4 cancer cells alone. B, E, H: CAOV4 cancer cells incubate with WT-1 TCR T cells. C, F, I: Dual specific TAG 72 CAR/WT-1 TCR T cells incubated with CAOV4 ovarian cancer cells. D,E,F: Aqua amine levels on gated CD3-ve cells (i.e., CAOVA4). Phase contrast images of G: Cancer cells alone, H: non-CAR transfected WT-1 TCR cells with cancer cells, and I: TAG-72 transfected WT-1 TCR T cells and cancer cells. 40× magnification. WT-1 TCR T cells caused approximately 10% killing (above background); TAG72 CAR-T cells caused an additional 10% killing (i.e., approximately 20% above background). Dual anti-cancer killing mechanisms are additive.

FIG. 20 shows that both components of the dual specific T cells (containing the WT-1 TCR and the TAG72 CAR) can contribute to the killing of cancer cells. When corrected for spontaneous cell death, even at low effector—target ratio (here it is 2 effectors to 1 target cell) the WT-1 cells caused approximately 10% cell killing and then addition of the TAG72 CAR by transduction caused an additional 10% killing.

Example 7: Chimeric Antigen Receptor Transduction of iPSC

The production of multi-specific CAR-T cells can be achieved by multiple approaches including CAR transduction of existing blood T cells (FIG. 15) or by transduction of iPSC which are then induced to T cells (expressing cancer specific TCR and the CAR's) (e.g., SEQ ID NOS: 1-6). Multiple iPSC lines have been used to progress with CAR-T transduction. These iPSC could be derived from non-T cells, or from cancer antigen specific T cells (e.g., WT-1) which would retain the TCR gene rearrangements. These iPSC were either derived from adult fibroblasts or from T cells with an endogenous TCR specific for a specific cancer antigen (WT-1 peptide).

Figure 21A:
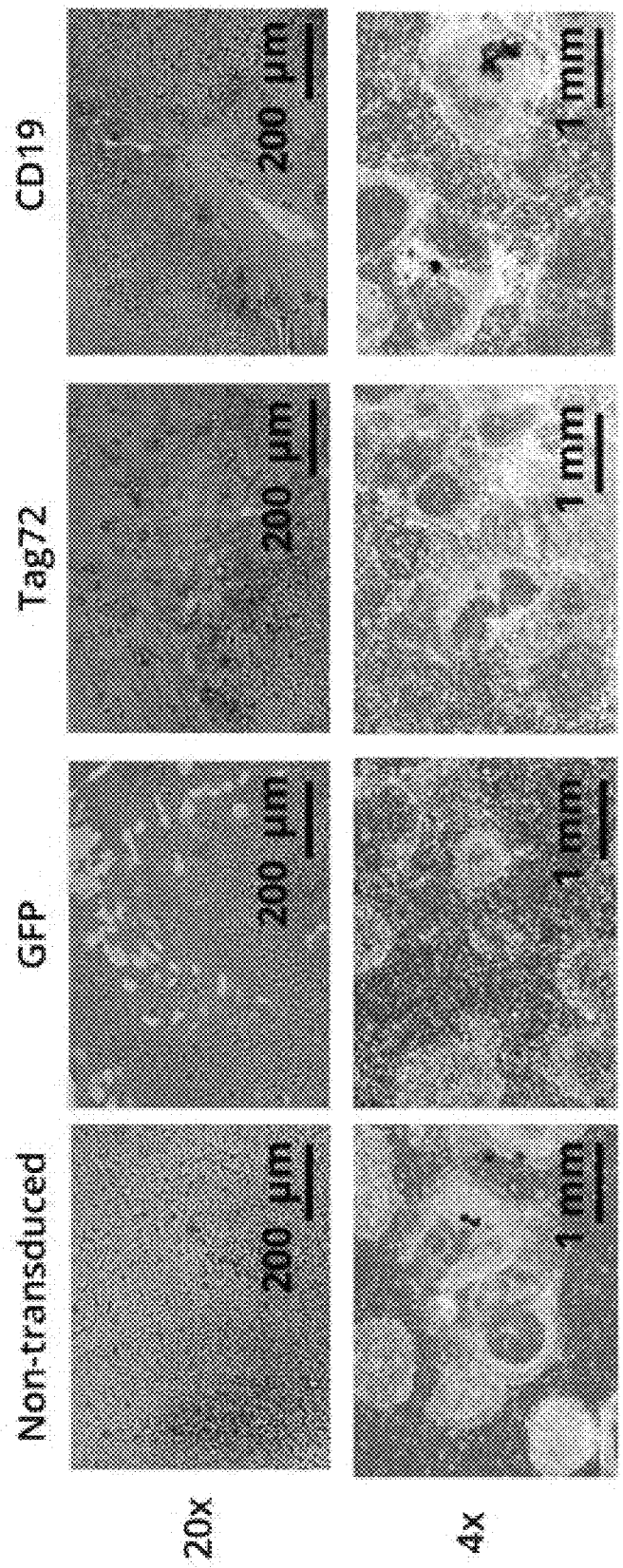
FIGS. 21A-21B. CAR transduction of iPS. Day 5 of growth on MEF feeder layers, 4 days after incubation with CAR lentivirus. CAR+ transduction (green) of TAG72, CD19 and GFP virus were overlayed on bright field images at 20× magnification. Non-transduced controls did not display any GFP signal. Images of iPSC colonies at 4× magnification demonstrate the presence of iPSC colonies on MEF feeder layers. In each system it is noted that some of the iPSC colonies appeared to have begun to spontaneously differentiate. Transduced fibroblast-derived iPSC are depicted in FIG. 21A.
Figure 21B:
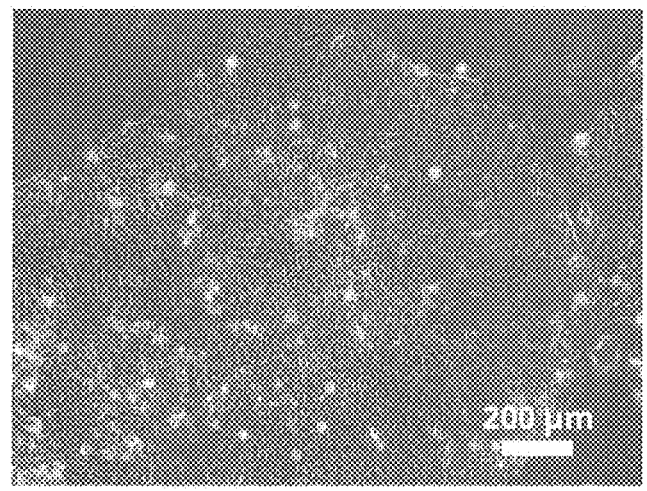
Figure 22:
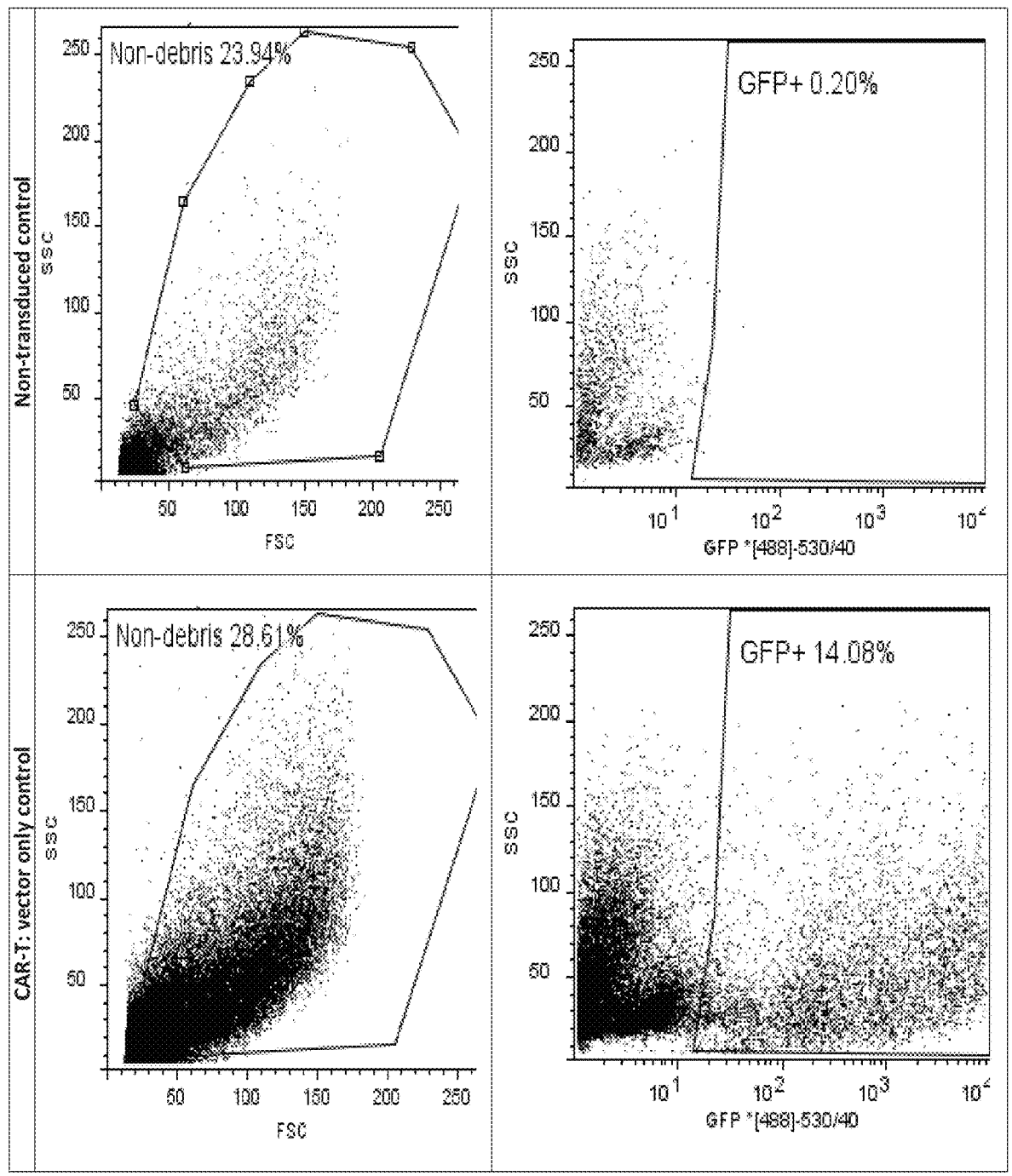
FIG. 22. Flow cytometric analysis of Chimeric Antigen Receptor transduction of iPSC. These iPSC are derived from adult fibroblasts but can be from any origin including non-selected T cells, CD8+ T cells or cancer antigen specific (e.g., WT-1) T cells. There is clearly a population of fluorescent iPSC successfully transduced by TAG 72 or CD19. Overlay of the transduced cells compared to non-transduced controls is shown in FIG. 23.
Figure 22:
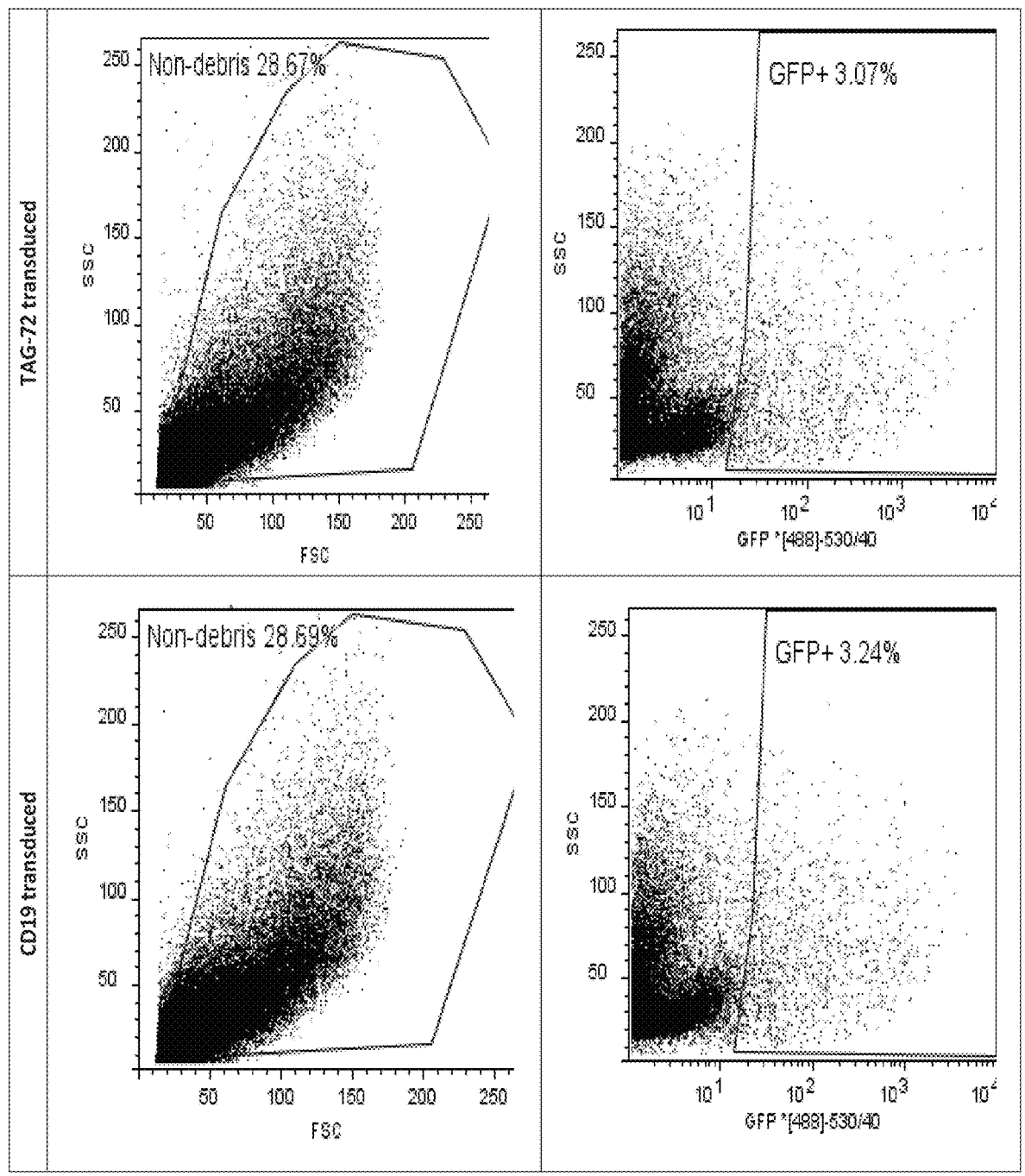
Figure 23:
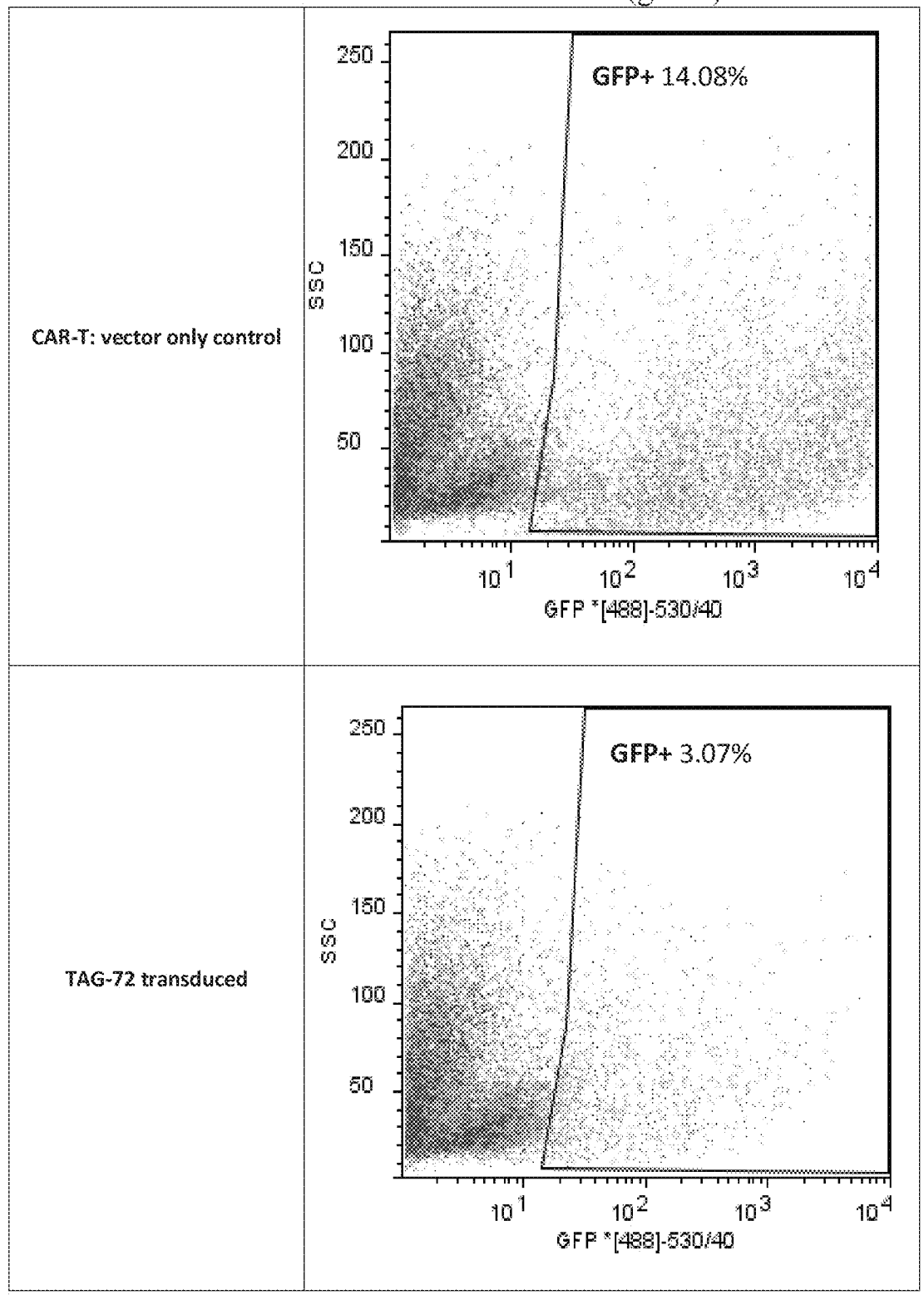
FIG. 23. Overlay of dot plots comparing non-transduced control cells (blue) to transduced iPSC cultures (green). Events within the GFP+ gate demonstrate successful transduction and are presented as percent frequency of non-debris events.
Figure 23:
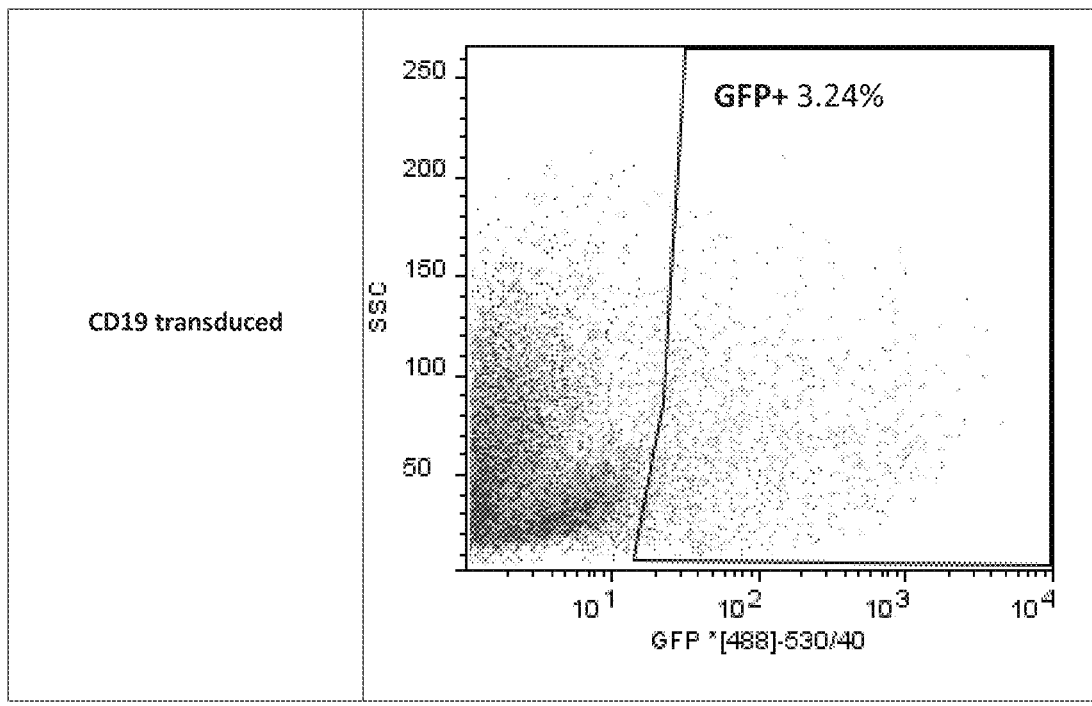

The iPSC were stably transduced with a single cistron, as shown in FIG. 14 in which the CAR ectodomain comprises an scFv specific for TAG72 (or as control CD19). The hinge (Stalk) region and the transmembrane region are derived from CD28 or CD8 and the cytoplasmic endodomain, which comprises T cell signal transduction domains, is derived from CD28 and TCRr chain. The CAR has a C-terminal extension encoding EGFP linked by a P2A self-cleaving polypeptide to separate the CAR and reporter. Following viral integration, the P2A was cleaved and the success of transduction was quantified by measuring the fluorescent of the released EGFP reporter. GFP fluorescence illuminates the success of transduction. It can be used to show transduction in situ (FIG. 21) or to identify and isolate CAR transduced iPSC via flow cytometry (FIG. 22, 23).

These studies clearly show the ability to transduce iPSC with lenti-virus CAR constructs. FIG. 21A shows the successful transduction of iPSC derived from human fibroblasts with a CAR encoding TAG 72 or CD19 (FIG. 21A). FIG. 21B shows the successful transduction of iPSC derived from WT-1 TCR specific T cells, with TAG72. Any T cell derived from this line will thus express dual anti-cancer specificity (WT-1 via TCR; TAG 72 via CAR).

Figure 24:
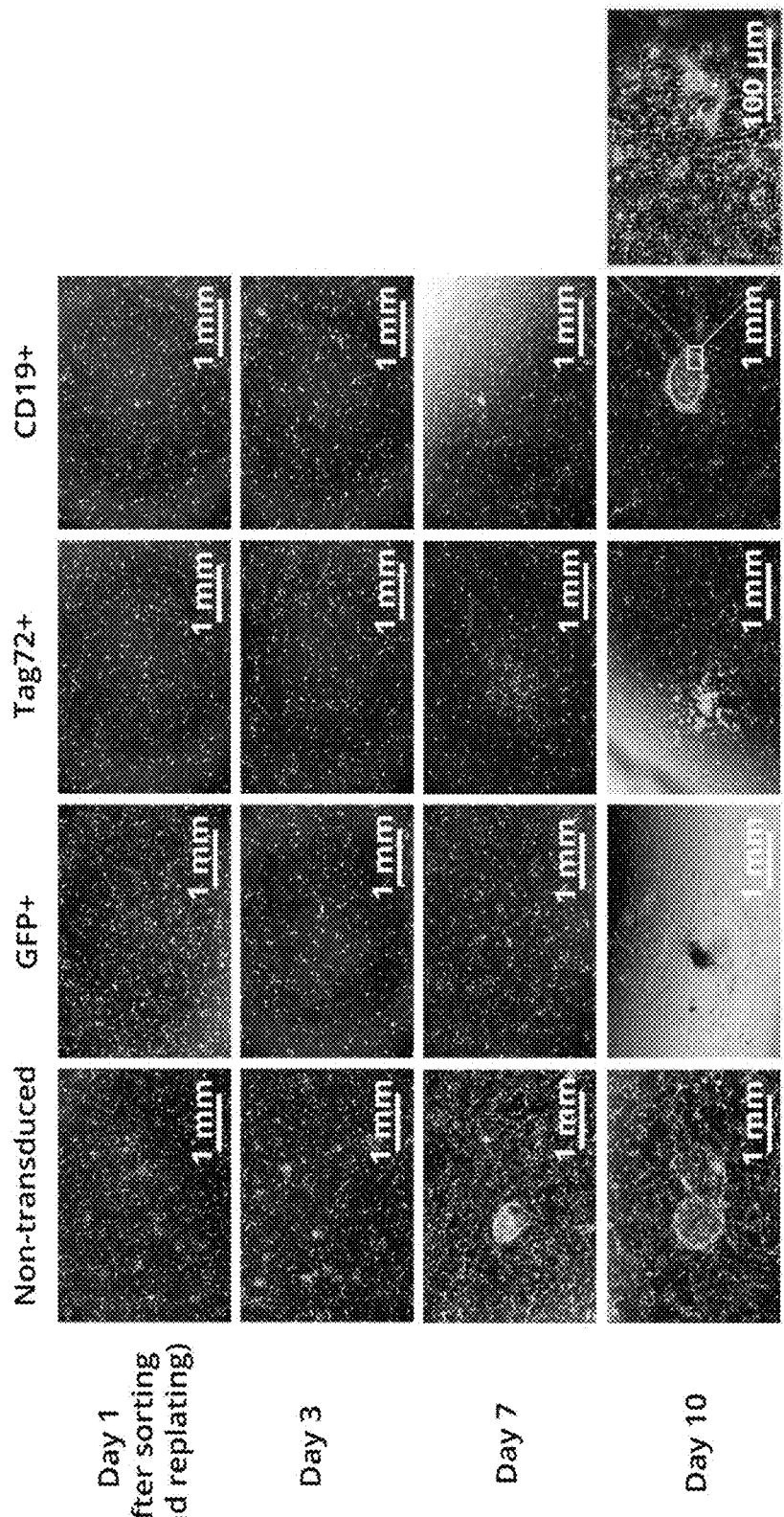
FIG. 24. Reformation of CAR-Transduced iPSC colonies after FACS sorting. CAR-transduced iPSC can be isolated by flow cytometry (GFP positive fluorescence) and replated to form stable colonies.

It is also possible to isolate the transduced iPSC by fluorescent-based cell sorting. The positive cells can be collected and replated to successfully form (CAR transduced) iPSC colonies (FIG. 24).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features

BIBLIOGRAPHY

Balasubramanian S, Babai N, Chaudhuri A, Qiu F, Bhattacharya S, Dave B J, Parameswaran S, Carson S D, Thoreson W B, Sharp J G, et al. (2009) *Non cell-autonomous reprogramming of adult ocular progenitors: generation of pluripotent stem cells without oxogenous transcription factors.* Stem Cells.; 27:3053-3062 [PubMed: 19859985]

Brignone, C., C. Grygar, M. Marcu, K. Schakel, and F. Triebel. 2007. *A soluble form of lymphocyte activation gene-3 (IMP321) induces activation of a large range of human effector cytotoxic cells.* J Immunol 179:4202.

Casucci M, Hawkins R E, Dotti G, Bondanza A. (2015). *Overcoming the toxicity hurdles of genetically targeted T cells.* Cancer Immunol Immunother.; 64(1):123-30

Chuo B K, Mali P, Huang X, Ye Z, Dowey S N, Resar L M, Zou C, Zhang Y A, Tong J, Cheng L. (2011) *Efficient human iPS cell derivation by a non-integrating plasmid from blood cells with unique epigenetic and gene expression signatures.* Cell Res.; 21: 518-529 [PubMed: 21243013]

Corrigan-Curay J, Kiem H P, Baltimore D, O'Reilly M, et al, Kohn D B. (2014). *T-cell immunology: looking forward.* Mol Ther.; 22(9): 1564-74

Curran K J, Pegram H J, Brentjens R J. (2012). *Chimeric antigen receptors for T cell immunotherapy: current understanding and future directions.* J Gene Med.; 14(6): 405-15

Curran K J, Seinstra B A, Nikhamin Y, Yeh R et al Brentjens R J (2015) *Enhancing Antitumor Efficacy of Chimeric Antigen Receptor T Cells Through Constitutive CD40L Expression.* Mol Ther.; January 13. doi: 10. 1038/mt. 2015. 4. [Epub ahead of print]

Davila M L, Riviere I, Wang X, Bartido S, et al Brentjens R. (2014). *Efficacy and toxicity management of 19-28z CAR T cell therapy in B cell acute lymphoblastic leukemia.* Sci Transl Med.; 6(224):224

Dotti G, Gottschalk S, Savoldo B, Brenner M K. (2014). *Design and development of therapies using chimeric antigen receptor-expressing T cells.* Immunol Rev.; 257 (1):107-26

Esteban M A, Wang T, Qin B, Yang J, Qin D, Cai J, Li W, Weng Z, Chen J, Ni S, et al. (2010) *Vitamin C enhances the generation of mouse and human induced pluripotent stem cells.* Cell Stem Cell.; 6:71-79 [PubMed: 20036631]

Fedorov V D, Sadelain M, Kloss C C. (2014). *Novel approaches to enhance the specificity and safety of engineered T cells.* Cancer J; 20(2):160-53.

Fletcher A L, Calder A, Hince M N, Boyd R L, Chidgey A P. (2011). *The contribution of thymic stromal abnormalities to autoimmune disease.* Crit Rev Immunol; 7(12): 954-63

Ghanekar S A, Nomura L E, Suni M A, Picker L J, Maecker H T, Maino V C. (2001). Gamma interferon expression in CD8(+) T cells is a marker for circulating cytotoxic T lymphocytes that recognize an HLA A2-restricted epitope of human cytomegalovirus phosphoprotein pp 65. Clin Diagn Lab Immunol. 8(3):628-31

Gargett, T, Brown M P. (2014). He inducible caspase 9 suicide gene systems as a 'safety switch" to limit on-target, off-tumourtoxicitiesofchimeric antigen receptorT cells. Front. Pharmacol 28:5:235

Ghosh et al., 1991 *Glycobiology* 5: 505-10

Han E Q, Li X L, Wang C R, Li T F, Han S Y. (2013). *Chimeric antigen receptor-engineered T cells for cancer immunotherapy: progress and challenges.* J Hematol Oncol.; 8; 6:47

Heng, T. S. P, Chidgey, A. P., and Boyd, R. L., (2010) Getting back at nature: understanding thymic development and overcoming its atrophy. Curr Opin Pharmacol, 10: 425-433

Huangfu D, Osafune K, Maehr R, Guo W, Eijkelenboom A, Chen S, Melton D A. (2008) *Induction of pluripotent stem cells from primary human fibroblasts with only Oct4 and Sox2.* Nat Biotechnol.; 26:1269-1275 [PubMed: 18849973]

Ichida J K, "Blanchard J, Lam K, Son E Y, Chung J E, Egli D, Loh K M, Carter A C, DiGiorgio F P, Kiszka K, et al. (2009) *A small-molecule inhibitor of TGF-β signalling replaces Sox2 in reprogramming by inducing nanog.* Cell Stem Cell.; 5:491-503 [PubMed: 19818703]

Kaji K, Norrby K, Paca A, Mileikovsky M, Mohseni P, Woltjen K. (2009) *Virus-free induction of pluripotency and subsequent excision of reprogramming factors.* Nature. 458:771-775

Lin T, Ambasudhan R, Yuan X, Li W, Hilcove S, Aburjarour R, Lin X, Hahm H S, Hao E, Hayek, A, Ding S. (2009) *A chemical platform for improved induction of human iPSCs.* Nat Methods; 6:805-808 [PubMed: 19838168]

Liu J et al. (PLOS One (2015) September 21; 10(9): e0137345)

Mali P, Chuo B K, Yen J, Ye Z, Zou J, Dowey S, Brodsky R A, Ohm J E, Yu W, Baylin S B, et al. (2010) *Butyrate greatly enhances derivation of human induced pluripotent stem cells by promoting epigenetic remodeling and the expression of pluripotency-associated genes.* Stem Cells; 28:713-720. [PubMed: 20201064]

Narsihn K H, Jia F, Robbins R C, Kay M A, Longaker M T, Wu J C. (2011) *Generation of adult human induced pluripotent stem cells sing nonviral minicircle DNA vectors.* Nature Protoc.; 6:78-88. [PubMed: 21212777]

Noggle S, Fung H-L, Gore A, Martinez H, Satriani K S, Prosser R, Oum K, Paull D, Druckenmiller S, Freeby M, et al. (2011) *Human oocytes reprogram somatic cells to a pluripotent state.* Nature.; 478:70-75 [PubMed: 21979046]

Pappas D J, Gourraud, R-A, Le Gall C, Laurent J, Trounson A, DeWitt N and Talib S. (2015) *Proceedings: Human Leukocyte Antigen Haplo-Homozygous Induced Pluripotent Stem Cell Haplobank Modeled After the California Population: Evaluating Matching in a Multiethnic and Admixed Population.* Stem Cells Translational Medicine 4:413-418

Perna S K, Savoldo B, Dotti G (2014). *Genetic modification of cytotoxic T lymphocytes to express cytokine receptors.* Methods Mol Biol.; 1139:189-200

"Sambrook et al. (2001, Molecular Cloning: A Laboratory Manual, Cold Spring Harbor Laboratory, New York)

Schmied, S, Gostsick E, Price D A, Abken H, Assenmacher M, Richter A. (2015). Analysis of the functional WT1 specific T-cell repertoire in healthy donors reveals a discrepancy between CD4+ and CD*+ memory formation. Immunology 145: 558-569

Subramanyam D, Lamouille S, Judson R L, Liu Jy, Bucay N, Derynck R, Blelloc R. (2011) *Multiple targets of miR-302 and mi$-372 promote reprogramming of human fibroblasts to induced pluripotent stem cells*. Nature Biotechnol.; 29:443-448. [PubMed: 21490602]

Themeli M, Kloss C C, Ciriello G et al M, Sadelain M (2013) Nat Biotechnol 31(10):928-33

Ui-Tei et al, 2000 FEBS Letters 479: 79-82

Warren L, Manos P D, Ahfeldt, Loh Y H, Li H, Lau F, Ebina W, Mandal P K, Smith Z D, Meissner A, et al. (2010) *Highly efficient reprogramming to pluripotency and directed differentiation of human cells with synthetic modified mRNA*. Cell Stem Cell.; 7:618-630. [PubMed: 20888316]

Woltjen K, Michael I P, Mohseni P, Desai R, Mileikovsky M, Hamalainen R, Cowling R, Wang W, Liu P, Gertsenstein M, et al. (2009) *piggy Bac transposition reprograms fibroblasts to induced pluripotent stem cells*. Nature; 458:766-770. [PubMed: 19252478]

Yoshida Y, Taskahashi K, Okita K, Ichisaka T, Yamanaka S. (2009) *Hypoxia enhances the generation of induced pluripotent stem cells*. Cell Stem Cell; 5:237-241 [PubMed: 19716359]

Zhu S, Li w, Zhou H, Wei W, Ambasudhan R, Lin T, Kim J, Zhang K, King S. (2010) *Reprogramming of human primary somatic cells by OCT4 and chemical compounds*. Cell Stem Cell; 7:651-655 [PubMed:21112560]

U.S. Pat. No. 5,350,674
U.S. Pat. No. 5,585,362
WO 2001/96584
WO 2001/29058
U.S. Pat. No. 6,326,193
U.S. patent application Ser. No. 14/656,431, published as US 20150183874 A1.

What is claimed is:

1. A nucleic acid encoding a chimeric antigen receptor (CAR), which comprises an antigen recognition moiety, and a T cell activation moiety, wherein:
   (i) said antigen recognition moiety is operably linked to the T cell activation moiety;
   (ii) said antigen recognition moiety is an scFv directed to TAG-72; and
   (iii) said nucleic acid comprises the nucleotide sequence of SEQ ID NO: 7 which encodes the scFv directed to TAG-72.

2. The nucleic acid of claim 1, wherein said T cell activation moiety comprises a 4-1BB signaling domain or a TCR zeta signaling domain.

3. The nucleic acid of claim 1, wherein said T cell activation moiety comprises a CD28 signaling domain or a TCR zeta signaling domain.

4. The nucleic acid of claim 1, wherein said CAR comprises a transmembrane domain selected from a CD8 transmembrane domain or a CD28 transmembrane domain.

5. The nucleic acid of claim 1, wherein the antigen recognition moiety in said CAR is linked to said T cell activation moiety through a hinge region and a transmembrane domain.

6. The nucleic acid of claim 5, wherein the hinge region comprises a cysteine that promotes dimerization of the CAR.

7. The nucleic acid of claim 1, wherein said CAR comprises
   (1) a CD8 hinge or a CD28 hinge;
   (2) a CD8 transmembrane domain;
   (3) a 4-1BB signaling domain; and
   (4) a TCR zeta signaling domain.

8. An isolated T cell, wherein said T cell
   (i) expresses a cell receptor (TCR) directed to a first antigenic determinant, and
   (ii) comprises the nucleic acid of claim 1 and expresses the CAR encoded by the nucleic acid of claim 1, wherein the CAR is directed to a second antigenic determinant, and wherein the second antigenic determinant is TAG-72.

9. The isolated T cell of claim 8, wherein the I cell activation moiety in the CAR comprises a 4-1BB signalling domain or a TCR zeta signaling domain.

10. The isolated T cell of claim 8, wherein said T cell activation moiety in the CAR comprises a CD28 signalling domain or a TCR zeta signaling domain.

11. The isolated cell of claim 8, wherein said cell expresses at least one homozygous MLA haplotype.

12. The isolated cell of claim 8, wherein the antigen recognition moiety in said CAR is linked to said T cell activation moiety through a hinge region and a transmembrane domain.

13. The isolated T cell of claim 12, wherein the hinge region comprises a cysteine that promotes dimerization of the CAR.

14. The isolated T cell of claim 8, wherein the T cell expresses a non-signalling antigen-binding receptor which comprises an antigen recognition moiety which is directed to a third antigenic determinant.

15. The isolated T cell of claim 14, wherein the first antigenic determinant, the second antigenic determinant and the third antigenic determinant are all different from each other.

16. The isolated T cell of claim 14, wherein said non-signalling antigen-binding receptor comprises an antigen recognition moiety directed to CD47.

17. The isolated T cell of claim 16, wherein the antigen recognition moiety of said non-signalling antigen-binding receptor is operably linked to a transmembrane region through a hinge region.

18. The isolated T cell of claim 17, wherein the non-signalling antigen-binding receptor does not form dimers.

19. The isolated T cell of claim 8, wherein the first antigenic determinant is WI-1.

20. A method of treating a neoplastic condition in a mammal, said method comprising administering to said mammal an effective number of T cell according to claim 8.

21. The method of claim 20, wherein the first antigenic determinant to which the TCR is directed to is a tumour antigenic determinant.

22. The method of claim 21, wherein said tumour antigenic determinant is WT-1.

\* \* \* \* \*